US011306318B2

(12) United States Patent
Løset et al.

(10) Patent No.: US 11,306,318 B2
(45) Date of Patent: Apr. 19, 2022

(54) VECTOR CONSTRUCT

(71) Applicant: Nextera AS, Oslo (NO)

(72) Inventors: Geir Åge Løset, Drøbak (NO); Terje Frigstad, Skjeberg (NO); Sebastian Berge-Seidl, Oslo (NO); Nicolay Rustad Nilssen, Vollen (NO); Inger Sandlie, Oslo (NO)

(73) Assignee: NEXTERA AS, Oslo (NO)

( * ) Notice: Subject to any disclaimer, the term of this patent is extended or adjusted under 35 U.S.C. 154(b) by 136 days.

(21) Appl. No.: 16/760,111

(22) PCT Filed: Nov. 5, 2018

(86) PCT No.: PCT/EP2018/080210
§ 371 (c)(1),
(2) Date: Apr. 29, 2020

(87) PCT Pub. No.: WO2019/086681
PCT Pub. Date: May 9, 2019

(65) Prior Publication Data
US 2020/0255843 A1 Aug. 13, 2020

(30) Foreign Application Priority Data
Nov. 3, 2017 (GB) .................................... 1718294

(51) Int. Cl.
*C40B 40/08* (2006.01)
*C12N 15/70* (2006.01)
(Continued)

(52) U.S. Cl.
CPC ............ *C12N 15/70* (2013.01); *C07K 14/005* (2013.01); *C12N 7/00* (2013.01); *C12N 15/1037* (2013.01);
(Continued)

(58) Field of Classification Search
None
See application file for complete search history.

(56) References Cited

U.S. PATENT DOCUMENTS

2014/0030697 A1  1/2014  Ploegh et al.

FOREIGN PATENT DOCUMENTS

| WO | 2010/104596 | 9/2010 |
| WO | 2011/036555 | 3/2011 |
| WO | 2014/018689 | 1/2014 |

OTHER PUBLICATIONS

Speck et al. "Efficient phage display of intracellularly folded proteins mediated by the TAT pathway", Protein Engineering Design and Selection, 24(6):473-484, Jun. 1, 2011, DOI: 10.1093/protein/gzr001 (Year: 2011).*

(Continued)

*Primary Examiner* — Christian C Boesen
(74) *Attorney, Agent, or Firm* — Wenderoth, Lind & Ponack, L.L.P.

(57) ABSTRACT

The present invention provides a vector construct comprising the following components: (i) a sequence encoding a signal peptide which directs proteins into the Tat secretory pathway; and (ii) a sequence encoding a fluorophore fused to a sequence encoding a pVIII phage coat protein. Nucleic acid molecules comprising components (i) and (ii) are also provided, together with phage particles comprising such vectors or nucleic acid molecules and expressing a fluorophore-pVIII fusion protein on the surface. Methods for producing such fluorescent phage particles are also provided.

34 Claims, 19 Drawing Sheets

Figure 2:
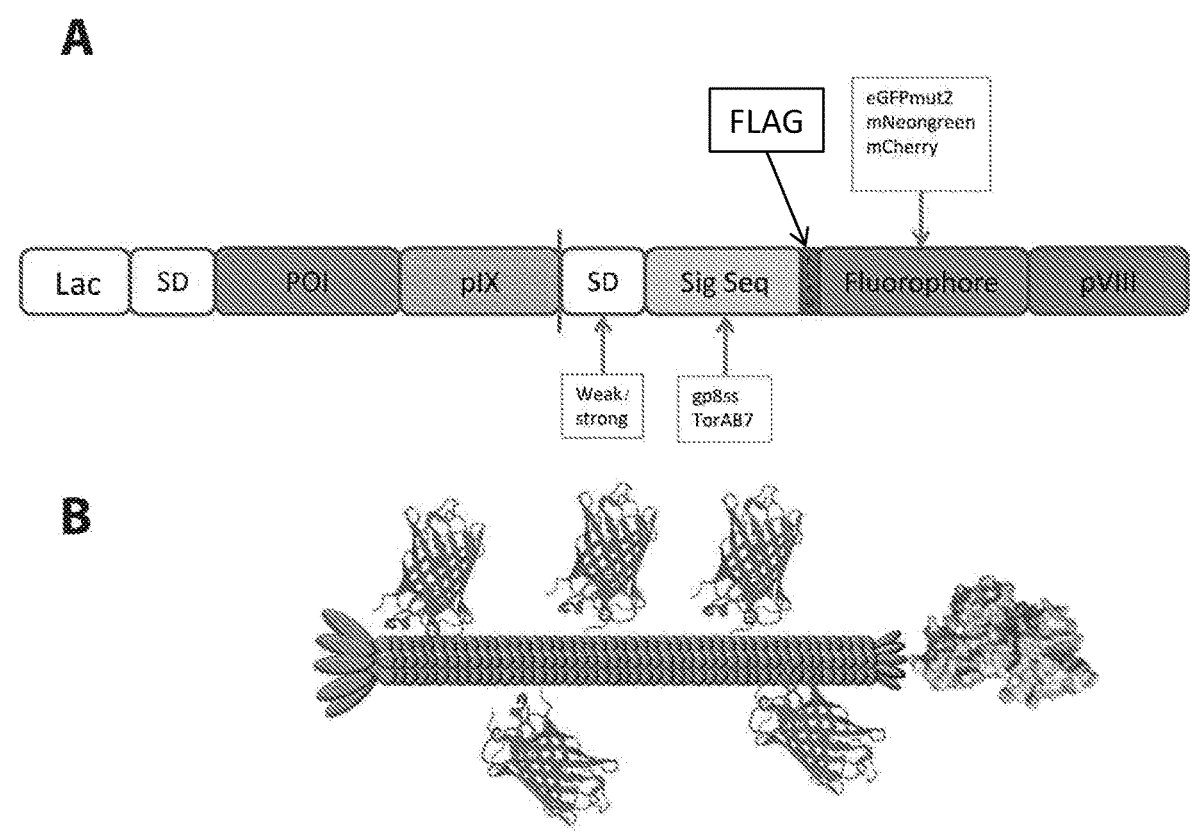

Specification includes a Sequence Listing.

(51) Int. Cl.
    C07K 14/005    (2006.01)
    C12N 7/00      (2006.01)
    C12N 15/10     (2006.01)
(52) U.S. Cl.
    CPC .......... C40B 40/08 (2013.01); C07K 2319/43
                (2013.01); C12N 2795/00022 (2013.01)

(56) References Cited

OTHER PUBLICATIONS

Gagic et al. "Exploring the Secretomes of Microbes and Microbial Communities Using Filamentous Phage Display", Frontiers in Microbiology, 7:429, Apr. 7, 2016, DOI=10.3389/fmicb.2016.00429 (Year: 2016).*

Boder, E. T. and Wittrup, K. D., "Yeast surface display for screening conlbinatorial polypeptide libraries", Nature Biotechnology, 1997, vol. 15, pp. 553-557.

Feldhaus et al., "Flow Cytometric Isolation of Human Antibodies from a Nonimmune *Saccharomyces cerevisiae* Surface Display Library", Nature Biotechnology, 2003, vol. 21, No. 2, pp. 1-25.

DeLisa et al., "Genetic Analysis of the Twin Arginine Translocator Secretion Pathway in Bacteria*", The Journal Of Biological Chemistry, 2002, vol. 277, No. 33, pp. 29825-29831.

Baneyx et al, "Recombinant protein folding and misfolding in *Escherichia coli*" Nature Biotechnology, 2004, vol. 22, No. 11, pp. 1399-1408.

Kumazaki et al., "Structural basis for Sec-independent membrane protein insertion by YidC", Nature, 2014, pp. 1-43.

Bendtsen et al., "Prediction of twin-arginine signal peptides", BMC Bioinformatics, 2005, vol. 6, No. 167, pp. 1-9.

Shaner et al., "Advances in fluorescent protein technology", Journal of Cell Science, 2007, vol. 120, No. 24, pp. 4247-4260.

Shaner et al., "A bright monomeric green fluorescent protein derived from Branchiostoma lanceolatum", Nature Methods, 2013, vol. 10, No. 5, 407-409, plus 29 pages of supplemental content.

Shaner et al., "Improved monomeric red, orange and yellow fluorescent proteins derived from Discosoma sp. red fluorescent protein", Nature Biology, 2004, vol. 22, No. 12, pp. 1567-1572.

Schaefer et al., "Engineering Aggregation Resistance in IgG by Two Independent Mechanisms: Lessons from Comparison of Pichia pastoris and Mammalian Cell Expression", Journal of Molecular Biology, 2012, vol. 417, pp. 309-335.

Dudgeon et al., "General strategy for the generation of human antibody variable domains with increased aggregation resistance", PNAS, 2012, vol. 109, pp. 10879-10884.

Weiss et al., "Mutational analysis of the major coat protein of M13 identifies residues that control protein display", Protein Science, 2000, vol. 9, pp. 647-654.

Hosse et al., "A new generation of protein display scaffolds for molecular recognition", Protein Science, 2006, vol. 15, pp. 14-27.

Smith, G. P., "Filamentous fusion phage: novel expression vectors that display cloned antigens on the virion surface", Science, 1985, vol. 228, pp. 1315-1317.

Løset, G. Ø and Sandlie, I., "Next generation phage display by use of pVII and pIX as display scaffolds", Methods, 2012, vol. 58, pp. 40-46.

Nilssen et al., "DeltaPhage—a novel helper phage for high-valence pIX phagemid display", Nucleic Acids Research, 2012, vol. 40, No. 16, e120, pp. 1-11.

Løset et al., "Expanding the Versatility of Phage Display II: Improved Affinity Selection of Folded Domains on Protein VII and IX of the Filamentous Phage" PL0S ONE, 2011, vol. 6, Issue 2, e17433, pp. 1-10.

Koch et al., "Rapid Titration of Multiple Samples of Filamentous Bacteriophage (M13) on Nitrocellulose Filters" 2000, BioTechniques, 2000, vol. 29, pp. 1196-1198.

Høydahl et al., "Multivalent pIX phage display selects for distinct and improved antibody properties", Scientific Reports, 2016, vol. 6, No. 39066, pp. 1-13.

Løset et al., "Expanding the Versatility of Phage Display I: Efficient Display of Peptide-Tags on Protein VII of the Filamentous Phage", PLoS ONE, 2011, vol. 6, Issue 2, e14702, pp. 1-7.

Gunnarsen et al., "Periplasmic expression of soluble single chain T cell receptors is rescued by the chaperone FkpA", BMC Biotechnology, 2010, vol. 10, No. 8, pp. 1-13.

Manting, E. H. and Driessen, A. J., "*Escherichia coli* translocase: the unravelling of a molecular machine", Molecular Microbiology, 2000, vol. 37, No. 2, pp. 226-238.

Berks et al., "Protein targeting by the bacterial twin-arginine translocation (Tat) pathway", Current Opinion in Microbiology, 2005, vol. 8, pp. 174-181.

Cormack et al., "FACS—optimized mutants of the green fluorescent protein (GFP)", Gene, 1996, vol. 173, pp. 33-38.

Zaccolo et al., "An Approach to Random Mutagenesis of DNA Using Mixtures of Triphosphate Derivatives of Nucleoside Analogues", J. Mol. Biol., 1996, vol. 255, pp. 589-603.

Huppa et al., "TCR-peptide-MHC interactions in situ show accelerated kinetics and increased affinity", Nature, 2010, vol. 463, pp. 963-970.

Straetemans et al., "TCR Gene Transfer: MAGE-C2/HLA-A2 and MAGE-A3/HLA-DP4 Epitopes as Melanoma-Specific Immune Targets", Clinical and Developmental Immunology, 2012, vol. 2012, Article ID 586314, pp. 1-14, 20 total pages.

Holst et al., "Generation of T-cell receptor retrogenic mice", Nature Protocols, 2006, vol. 1, No. 1, pp. 406-417.

Heim et al., "Improved Green Fluorescence", Nature, 1995, vol. 373, 663-664.

Bossi, L., "Context Effects: Translation of UAG Codon by Suppressor tRNA is Affected by the Sequence Following UAG in the Message", J. Mol. Biol., 1983, vol. 164, pp. 73-87.

Bowley et al., "Libraries against libraries for combinatorial selection of replicating antigen-antibody pairs", PNAS, 2009, vol. 106, No. 5, pp. 1380-1385.

Chen et al., "Design and Validation of a Bifunctional Ligand Display System for Receptor Targeting", Chemistry & Biology, 2004, vol. 11, pp. 1081-1091.

De Boer, H. A., and Hui, A. S., "Sequences within Ribosome Binding Site Affecting Messenger RNA Translatability and Method to Direct Ribosomes to Single Messenger RNA Species", Methods in Enzymology, 1990, vol. 185, pp. 103-114.

Goodman et al., "Causes and Effects of N-Terminal Codon Bias in Bacterial Genes", Science, 2013, vol. 342, pp. 475-479.

Thammawong et al., "Twin-arginine signal peptide attributes effective display of CD 147 to filamentous phage", Appl Microbiol. Biotechno., 2006, vol. 69, pp. 697-703.

Velappan et al., "A comprehensive analysis of filamentous phage display vectors for cytoplasmic proteins: an analysis with different fluorescent proteins", Nucleic Acids Research, 2010, vol. 38, No. 4, e22, pp. 1-16.

Hess et al., "M13 Bacteriophage Display Framework That Allows Sortase-Mediated Modification of Surface-Accessible Phage Proteins", Bioconjugate Chemistry, 2012, vol. 23, pp. 1478-1487, 19 total pages.

Speck et al., "Efficient phage display of intracellularly folded proteins mediated by the TAT pathway", Protein Engineering, Design & Selection, 2011, vol. 24, No. 6, pp. 473-484, 17 total pages.

Velappan et al., "A comprehensive analysis of filamentous phage display vectors for cytoplasmic proteins: an analysis with different fluorescent proteins", Nucleic Acids Research, 2009, pp. 1-16.

Wang et al., "On the Mechanism of Targeting of Phage Fusion Protein-Modified Nanocarriers: Only the Binding Peptide Sequence Matters", Molecular Pharmaceutics, 2011, vol. 8, pp. 1720-1728.

Hashiguchi, Shuhei et al., "Beyond antibody using phage display: Molecular targeting with antibody-like molecule", 2010, pp. 710-726, with English abstract.

Kikuchi, Yoshimi, "Bacterial novel protein secretion pathways and their applications: Twin-Arginine Translocation Pathway", 2009, vol. 47, No. 6, pp. 397-403, with English abstract.

\* cited by examiner

FIG. 1
A
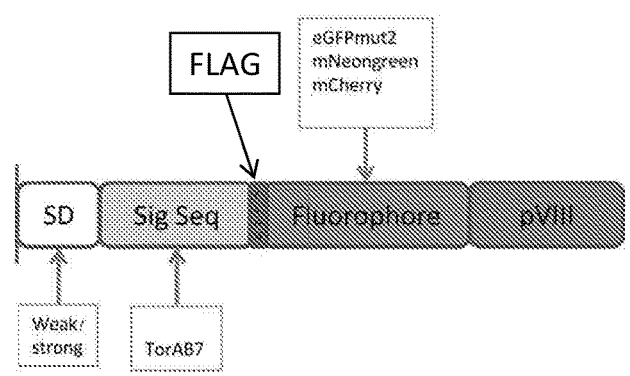
B
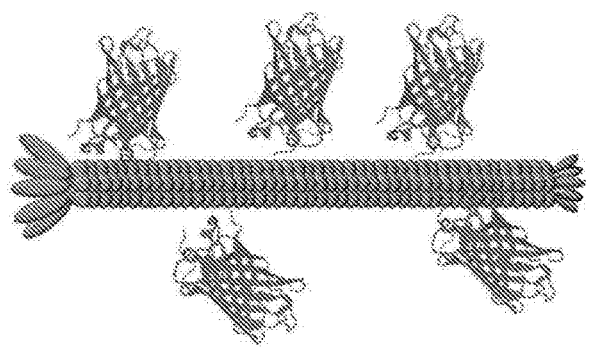

A.
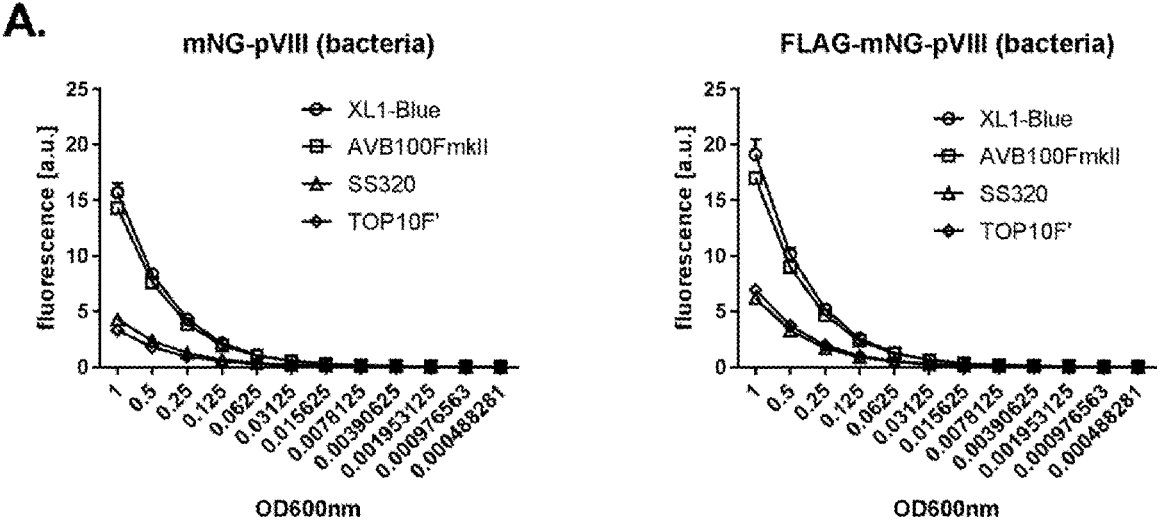
B.
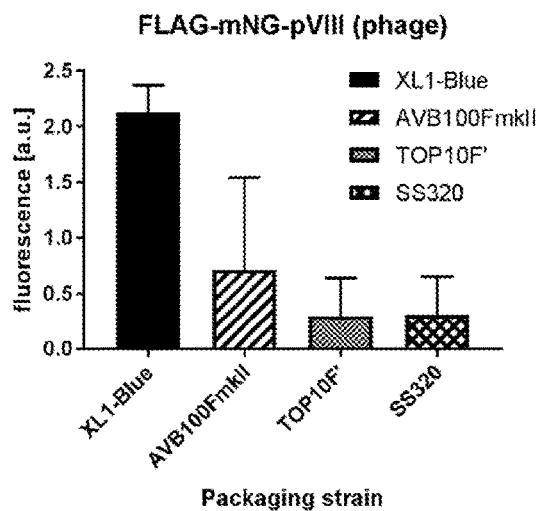
FIG. 5

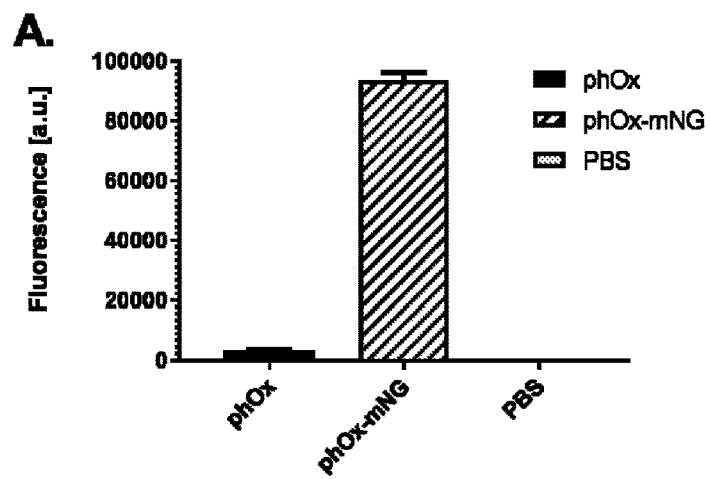
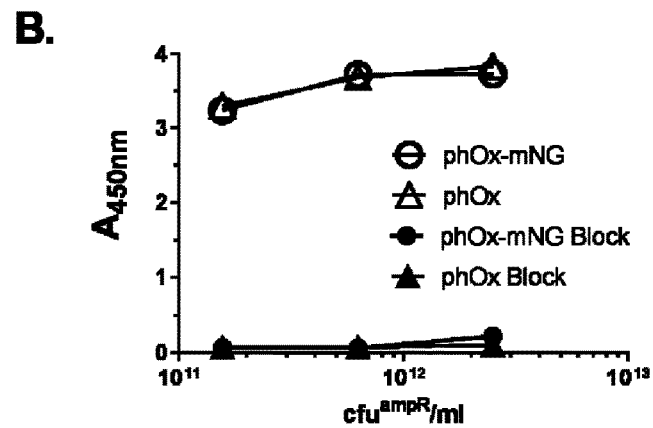
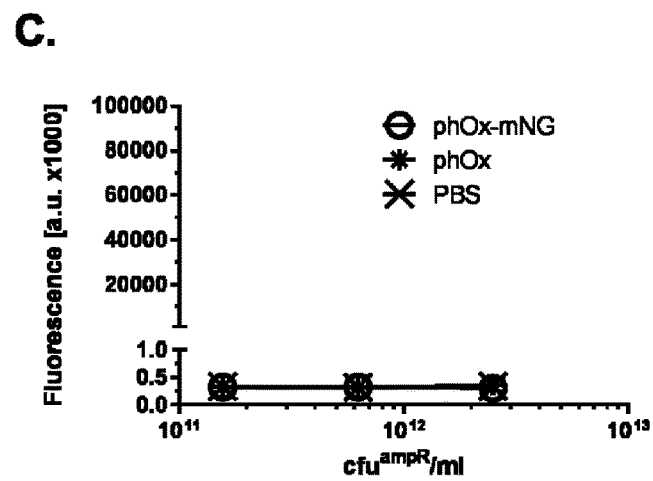
FIG. 6

FIG. 9

```
  1 ATGAACAATAACGATCTCTTTCAGACATCACGTCAGCGTTTTTTGGCACAACTCGGCGGC  60
    ----:----|----:----|----:----|----:----|----:----|----:----|
  1 M  N  N  N  D  L  F  Q  T  S  R  Q  R  F  L  A  Q  L  G  G   20
    |← -----TorAB7 amino acid sequence START------------------

61 TTAACCGTCGCCGGGATGCTGGGGCCGTCATTGTTAACGCCGCGACGTGCGACTGCGGCG 120
    ----:----|----:----|----:----|----:----|----:----|----:----|
 21 L  T  V  A  G  M  L  G  P  S  L  L  T  P  R  R  A  T  A  A   40
    -------------- TorAB7 amino acid sequence END ----- →|

121 GattacaaggatgacgatgacaagGGCGTTTCTAAAGGTGAAGAAGACAACATGGCTTCT 180
    ----:----|----:----|----:----|----:----|----:----|----:----|
 41 D  Y  K  D  D  D  D  K  G  V  S  K  G  E  E  D  N  M  A  S   60
    |←FLAG tag amino acids→|    |← --------- mNeonGreen amino acid 181 CTGCCGGCTACCCACGAACTGCACATCTTCGGTTCTATCAACGGTGTTGACTTCGACATG 240
    ----:----|----:----|----:----|----:----|----:----|----:----|
 61 L  P  A  T  H  E  L  H  I  F  G  S  I  N  G  V  D  F  D  M   80
    sequence START-------------------------------------------

241 GTTGGTCAGGGTACCGGTAACCCGAACGACGGTTACGAAGAACTGAACCTGAAATCTACC 300
    ----:----|----:----|----:----|----:----|----:----|----:----|
 81 V  G  Q  G  T  G  N  P  N  D  G  Y  E  E  L  N  L  K  S  T  100
    ---------------------------------------------------------

301 AAAGGTGACCTGCAGTTCTCTCCGTGGATCTTAGTTCCGCACATCGGTTACGGTTTCCAC 360
    ----:----|----:----|----:----|----:----|----:----|----:----|
101 K  G  D  L  Q  F  S  P  W  I  L  V  P  H  I  G  Y  G  F  H  120
    ---------------------------------------------------------

361 CAGTACCTGCCGTACCCGGACGGTATGTCTCCGTTCCAGGCTGCTATGGTTGACGGTTCT 420
    ----:----|----:----|----:----|----:----|----:----|----:----|
121 Q  Y  L  P  Y  P  D  G  M  S  P  F  Q  A  A  M  V  D  G  S  140
    ---------------------------------------------------------

421 GGTTACCAGGTTCACCGTACCATGCAGTTCGAAGACGGTGCTTCTCTGACCGTTAACTAC 480
    ----:----|----:----|----:----|----:----|----:----|----:----|
141 G  Y  Q  V  H  R  T  M  Q  F  E  D  G  A  S  L  T  V  N  Y  160
    ---------------------------------------------------------

481 CGTTACACCTACGAAGGTTCTCACATCAAAGGTGAAGCTCAGGTTAAAGGTACCGGTTTC 540
    ----:----|----:----|----:----|----:----|----:----|----:----|
161 R  Y  T  Y  E  G  S  H  I  K  G  E  A  Q  V  K  G  T  G  F  180
    ---------------------------------------------------------

541 CCGGCTGACGGTCCGGTTATGACCAACTCTCTGACCGCTGCTGACTGGTGCCGTTCTAAA 600
    ----:----|----:----|----:----|----:----|----:----|----:----|
181 P  A  D  G  P  V  M  T  N  S  L  T  A  A  D  W  C  R  S  K  200
    ---------------------------------------------------------

601 AAAACCTACCCGAACGACAAAACCATCATCTCTACCTTCAAATGGTCTTACACCACCGGT 660
    ----:----|----:----|----:----|----:----|----:----|----:----|
201 K  T  Y  P  N  D  K  T  I  I  S  T  F  K  W  S  Y  T  T  G  220
    ---------------------------------------------------------
```

```
661 AACGGTAAACGTTACCGTTCTACCGCTCGTACCACCTACACCTTCGCTAAACCGATGGCT 720
    ----:----|----:----|----:----|----:----|----:----|----:----|
221 N  G  K  R  Y  R  S  T  A  R  T  T  Y  T  F  A  K  P  M  A  240
    ------------------------------------------------------------

721 GCTAACTACCTGAAAAACCAGCCGATGTACGTTTTCCGTAAAACCGAACTGAAACACTCT 780
    ----:----|----:----|----:----|----:----|----:----|----:----|
241 A  N  Y  L  K  N  Q  P  M  Y  V  F  R  K  T  E  L  K  H  S  260
    ------------------------------------------------------------

781 AAAACCGAACTGAACTTCAAAGAATGGCAGAAAGCTTTCACCGACGTTATGGGTATGGAC 840
    ----:----|----:----|----:----|----:----|----:----|----:----|
261 K  T  E  L  N  F  K  E  W  Q  K  A  F  T  D  V  M  G  M  D  280
    ---------------------------- mNeonGreen amino acid seqeunce 841 GAACTGTACAAAGGCGGTGGCAGCGGCGGTGGCAGCGCTGAGGGTGACGATCCCGCAAAA 900
    ----:----|----:----|----:----|----:----|----:----|----:----|
281 E  L  Y  K  G  G  G  S  G  G  G  S  A  E  G  D  D  P  A  K  300
    END ---- →|  |←Linker amino acids→|  |← --- pVIII amino acid 901 GCGGCCTTTAACTCCCTGCAAGCCTCAGCGACCGAATATATCGGTTATGCGTGGGCGATG 960
    ----:----|----:----|----:----|----:----|----:----|----:----|
301 A  A  F  N  S  L  Q  A  S  A  T  E  Y  I  G  Y  A  W  A  M  320
    sequence START ---------------------------------------------

961 GTTGTTGTCATTGTCGGCGCAACTATCGGTATCAAGCTGTTTAAGAAATTCACCTCGAAA 1020
    ----:----|----:----|----:----|----:----|----:----|----:----|
321 V  V  V  I  V  G  A  T  I  G  I  K  L  F  K  K  F  T  S  K  340
    -------------------------------- pVIII amino acid sequence 1021 GCAAGCTGATAA 1032
     ----:----|--
 341 A  S  *  *                                                  342
     END→|
```

FIG. 9 continued

Figure 12:
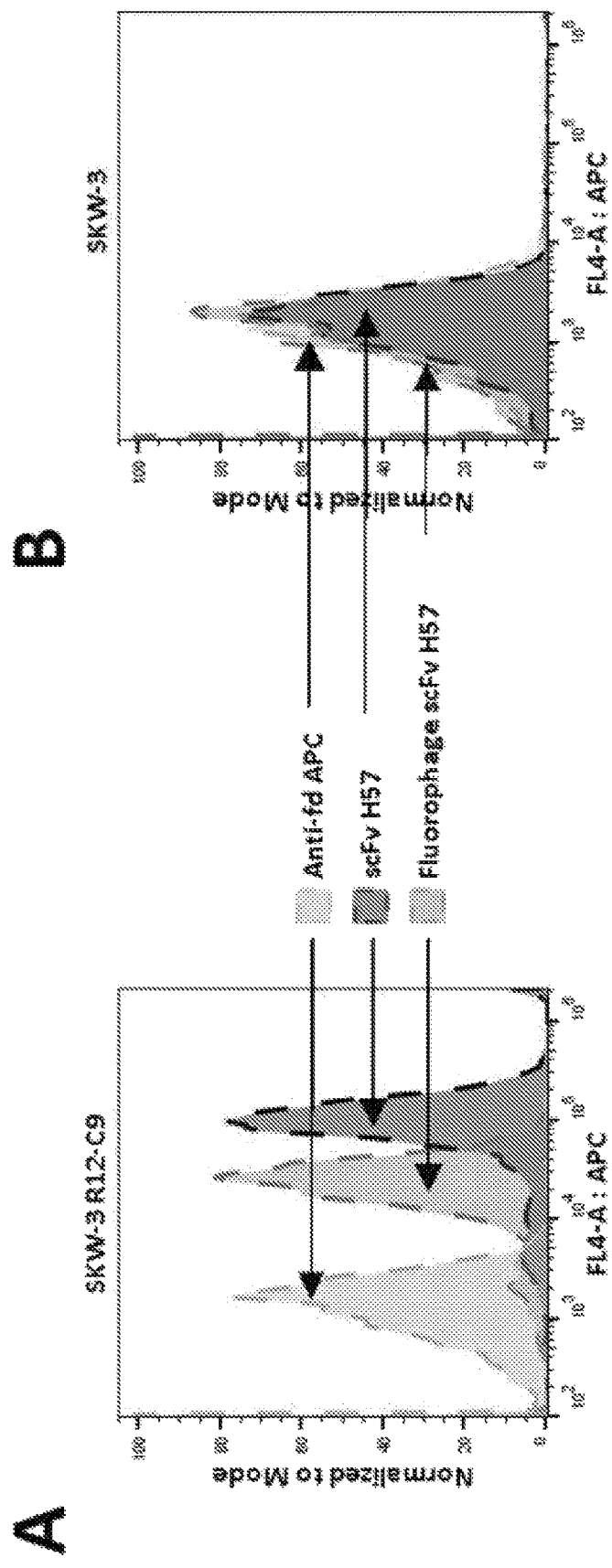

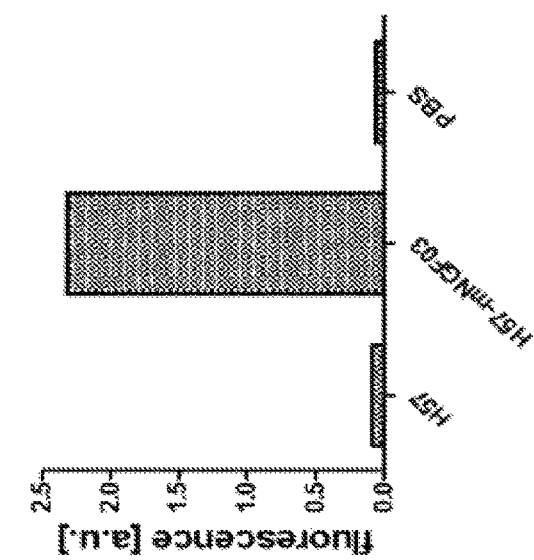
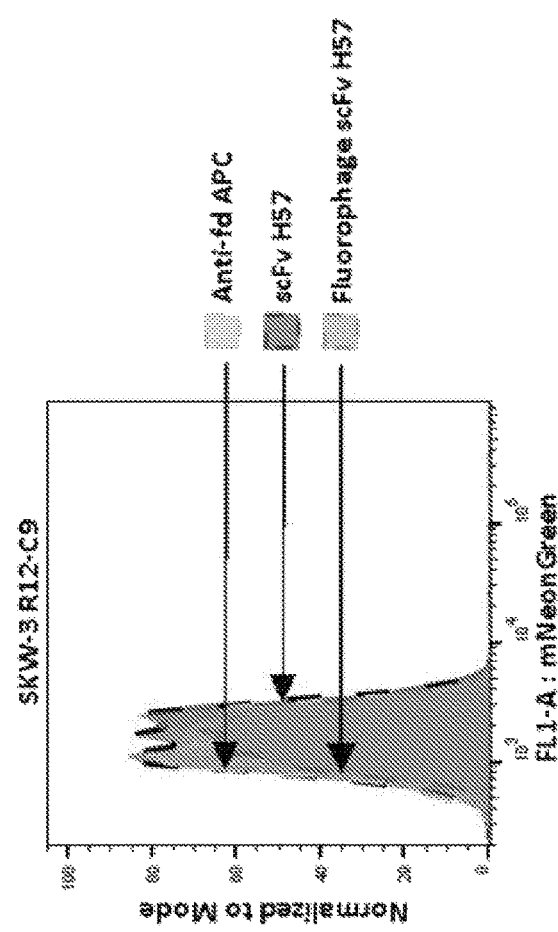
FIG. 12 continued

VECTOR CONSTRUCT

The present invention relates to phage display and in particular fluorescent phage particles and nucleic acid vectors for the production of fluorescent phage particles. More particularly, the present invention relates to vector constructs in which a sequence encoding a fluorophore is fused to a sequence encoding a pVIII phage coat protein.

Over the last three decades, phage display has become a powerful and efficient method for discovery and evolution of novel binding proteins. Though competing combinatorial technologies exist, none show the high degree of versatility combined with the ease of use. Nonetheless, it is still challenging to screen for the desired phenotype following phage panning, and it is not given that the optimal binders are identified. Real time selection, as offered by flow cytometry-compatible cellular combinatorial technologies such as yeast display has a significant advantage, as fluorescently labeled ligand and fluorescence-activated cell sorting (FACS) efficiently separates binders from non-binders in a quantitative manner combined with their retrieval (Boder and Wittrup, 1997, Nat Biotechnol., 15, 553-557 and Feldhaus et al., 2003, Nat Biotechnol., 21, 163-170).

Efficient FACS-based methods have yet to be integrated with phage display for a number of reasons: 1) A phage particle is too small to be detected by size (forward and side scatter) in flow, thus direct fluorescent labeling or indirect visualization such as by labeled anti-phage antibodies is needed, which significantly limits the sensitivity and utility (Bowley et al., 2009, PNAS 106:1380-1385), 2) FACS requires a retrievable physical particle, thus, as a phage particle alone is too small, the target must either be expressed on a cell surface, or immobilized on a solid phase, such as beads, 3) Direct fluorescent labeling of phage by chemical coupling may disrupt target binding when free reactive groups are present at or near the binding site, or introduces sterical hindering of antigen binding, 4) Antibody detection requires additional incubation and washing steps that leads to potential loss of clones and lowers selection efficiency.

Thus, integrating an inherent fluorescent detection module into the phage platform would significantly improve the ability to use FACS-based methods as well as providing a highly useful tool for other types of assays based on detection using fluorescence.

Functional display of fluorescent proteins on the surface of phage particles has been achieved previously. For example, Velappan et al., (Nucleic Acid Research, 38 (4): e22, 2010) have shown that some forms of GFP can be expressed as a fusion with either the pIX or pIII phage coat proteins, although the best constructs did not have a direct genetic fusion between the fluorophore and the phage coat protein but instead used a coiled coil arrangement to join the fluorophore and the phage coat protein in an indirect post-translational manner where each component is encoded and expressed as separate, individual components. In addition, Speck et al., (Protein Engineering, Design & Selection: PEDS, 24, 473-484, 2011) have shown that GFP and some GFP derivatives can be expressed as a direct fusion with a truncated form (C-terminal domain only) of the pIII phage coat protein in a phagemid system.

pVIII is the major coat (capsid) protein on filamentous phage and thus fusion of fluorophores to the pVIII coat protein is potentially advantageous due to its high copy number per phage particle, and being non-interfering with tip display on either of the remaining four capsid proteins. However, reports on classic phage display based fusions of heterologous molecules with the pVIII coat protein are confined to the display of short peptides.

Furthermore, as discussed above, the functional phage display of fluorophores using classic phage display techniques can be problematic. One reason for this is that the fluorophore proteins are quite sensitive and are normally expressed and folded in the cytoplasm in order to be functional, which can present problems in terms of obtaining transfer of expressed fluorophore-phage coat protein fusion proteins to the periplasm and functional fluorophores displayed on the phage surface (DeLisa et al., J. Biol. Chem., 277 (33), 29825-29831, 2002).

Current techniques to address this issue involve the use of fluorescently labelled anti-pVIII antibodies which can in turn be used to fluorescently label the phage particles which can then be detected using standard techniques, e.g. by flow cytometry or fluorescent staining.

More recently, Hess et al., 2012 (Bioconjugate Chemistry, 23:1478-1487), have overcome some of these problems by demonstrating fusion of GFP on a phage pVIII coat protein using a post translational technique wherein a sortase enzyme is used to conjugate GFP molecules to pVIII molecules present on the surface of phage particles.

This has been achieved by using standard phage display techniques to obtain phage particles expressing pVIII coat proteins with a short peptide insertion which can be recognised by the sortase enzyme. This peptide insertion can then be subjected to standard sortase technology in order to post-translationally join the modified pVIII coat protein on the surface of the phage to GFP molecules obtained from standard sources.

Thus, although Hess et al., (supra) provide phage particles in which pVIII proteins are fused to GFP fluorophores, it is not done by classic phage display techniques where there would be a genetic fusion within the phage particle between a nucleic acid sequence encoding the pVIII coat protein and a sequence encoding the fluorophore such that a fusion protein would be produced. This also means that there is no genotype-phenotype link in the Hess system which is disadvantageous for screening technologies where an important feature of the classic phage display approach is that a selected phage particle which displays a protein of interest (e.g. a protein which binds to a target ligand) contains the genetic material coding for this displayed protein of interest which can then be obtained and further analysed or manipulated.

In the present invention, surprisingly and contrary to expectations from the prior art teaching such as that described above, the present inventors have found that fluorescent proteins can be displayed on phage particles as a genetic fusion with the pVIII phage coat protein. This has been achieved by the provision of a vector construct which combines the use of the *E. coli* Tat secretory pathway with a fluorophore-pVIII fusion protein. Such vectors advantageously allow the production of phage particles which display functional and detectable fluorescent proteins. In other words, the phage particles are intrinsically (or inherently) fluorescent.

The inventors have also shown that such vectors can be used to incorporate a second fusion of a protein of interest (POI) with an alternative (non-pVIII) phage coat protein in order to achieve simultaneous surface display of both the fluorescent-pVIII fusion protein and the protein of interest fused to another coat protein. In other words, the inventors have demonstrated herein the generation of vectors and phage particles with both intrinsic fluorescence capability and another capability provided by a POI, e.g. target binding activity. Thus, this fluorescent phage system of vectors and phage produced using the vectors (also termed herein as Fluorophage) can advantageously be used for selection and screening in order to combine the advantages and ease of fluorescent screening with the ability to immediately and readily investigate a selected POI using the phenotype-genotype link from classic phage display. This fluorescent phage system has uses in non-FACS assays, as it by itself is directly compatible with classical microtiter plate-based screening approaches traditionally done as enzyme-linked immunosorbent assays (ELISA), or similar, which could now be simplified and rely on quantitative fluorescent measures instead, e.g. by way of FLISA (Fluorescent Linked Immunosorbent Assay). Other uses are described elsewhere herein.

Further, the inventors have shown that by building on the ability of now having a genetic fusion protein as detection module as an inherent part of the phage display system, one can also use combinatorial molecular evolution to optimize and improve the fusion protein. This was done by randomizing the sequence encoding the fluorophore and parts of pVIII, followed by phenotypic screening in FACS for increased signal in comparison with the mother construct. This allowed for the identification of a new mutant fusion protein that increased the signal obtained beyond what is seen with the mother construct. The effect appears to be due to better accommodation of the heterologous protein to the producing *E. coli* host, such that the net result is an increase in the functional fusion protein pool that translates to both increased fluorescent signal from the producing cell, as well as the phage particles produced by this cell. In addition, the inventors have shown that overexpression of the Tat transporter in *E. coli* host cells can significantly improve the fluorescent signal.

Thus, in one aspect, the present invention provides a vector construct comprising the following components:
  (i) a sequence encoding a signal peptide which directs proteins into the Tat secretory pathway; and
  (ii) a sequence encoding a fluorophore fused to a sequence encoding a pVIII phage coat protein.

The vectors of the invention are expression vectors or expression constructs, i.e. are generally comprised of nucleic acid sequences which enable the expression (protein synthesis) of desired encoded protein components in an appropriate host cell.

As outlined above, this invention is in the field of phage display. Thus, the vectors of the invention can be phage vectors or phagemid vectors (plasmids) the basic construction and components of which will be well known to a person skilled in the art and selected in order to achieve expression of phage proteins and packaging of phage particles in an appropriate host cell such that the heterologous or exogenous proteins fused to the various phage coat proteins are displayed on the surface of the phage particle.

Thus, when the vectors of the invention are used to transform an appropriate host cell such as an appropriate *E. coli* strain, phage particles are produced which contain a number of functional fluorophore molecules fused to the pVIII phage coat protein and displayed on the surface of the phage particle, with the vector sequences or other nucleic acid sequences encoding the various phage components of the phage genome contained within the phage particle. Such a functional fluorophore displayed on the surface of the phage can be detected by conventional techniques such as fluorescent staining (detectable by for example fluorescent microscopy or flow cytometry, or a fluorescence reader or detector, e.g. a plate reader or scanner or a luminometer).

The present invention extends to nucleic acid sequences or nucleic acid molecules which can form part of the vectors of the invention. Thus, another aspect of the invention provides a nucleic acid molecule or nucleic acid sequence comprising the following components:
  (i) a sequence encoding a signal peptide which directs proteins into the Tat secretory pathway; and
  (ii) a sequence encoding a fluorophore fused to a sequence encoding a pVIII phage coat protein.

The present invention further provides phage or phage particles comprising the vectors or nucleic acid molecules of the invention and expressing a fluorophore-pVIII fusion protein on the surface. Such phage or phage particles can be any filamentous phage. Preferred examples are Enterobacteria phage, for example M13, fd and f1 phages.

The vectors of the present invention thus comprise a sequence encoding a signal peptide. This signal peptide (or signal sequence, or leader sequence, or periplasmic leader peptide, or periplasmic leader sequence) can be any appropriate sequence (amino acid sequence) which directs or targets proteins into the Twin-Arginine Translocation (Tat) export or secretory pathway (or translocation pathway), e.g by targeting or directing the protein to the Tat transporter. Such signal peptides are also referred to herein as Tat signal peptides. In the vectors of the invention, this sequence encoding the signal peptide is operably linked to the sequence encoding the fluorophore-pVIII fusion protein (a fluorophore protein fused to a pVIII protein) and thus directs protein (the fluorophore-pVIII fusion protein) into the Tat secretory pathway.

The Tat pathway is one of several translocation or secretory pathways found in bacterial host cells such as *E coli*. In this pathway, the protein is folded in the reducing conditions of the cytoplasm prior to translocation of the fully folded protein across the inner membrane to the periplasm. Upon reaching the periplasm, the signal peptide is then removed by an appropriate signal peptidase. Other known translocation or secretory pathways in Gram-negative bacteria such as *E. coli* which are involved in translocation of proteins from the cytosolic to the periplasmic compartment are the signal recognition particle (SRP)-dependent SEC pathway, the classical secretory (Sec) pathway or the YidC-dependent pathway (Baneyx, 2004, Nat. Biotechnol 22:1399-1408). In contrast to the Tat pathway, SEC pathways transport unfolded proteins across the inner membrane to the periplasm involving a threading mechanism, whereas YidC-mediated transport may also involve at least partially folded transport using the flippase mechanism (Kumazaki et al., 2014, Nature 509:516-520).

Appropriate signal sequences or signal peptides for the Tat pathway would be well known to a person skilled in the art and any of these can be used, or indeed derivatives or variants thereof which display retained or improved ability to direct proteins into the Tat pathway. Indeed, the name of the Tat pathway (Twin-Arginine Translocation) refers to a highly conserved twin-arginine leader motif (S/TRRXFLK, SEQ ID NO:33) which is found in the N-terminal region of proteins destined for transport via the Tat pathway. In this sequence, X can be any amino acid, preferably any polar amino acid. Thus, this would be an exemplary sequence which could form part of the signal peptide in the vectors of the invention.

A preferred example would be the *E. coli* trimethylamine N-oxide reductase (Tor A) signal sequence or a derivative (or variant) thereof which retains or has an improved ability (e.g. a gain of function mutant) in comparison to the starting sequence to export proteins via the Tat pathway. Exemplary and preferred derivatives are for example as described in DeLisa et al. (J. Biol. Chem., 277 (33), 29825-29831, 2002).

The full sequence of the wildtype Tor A leader sequence is as follows (MNNNDLFQA SRRRFLAQLGGLTVAGMLGPSLLTPRRAT, SEQ ID NO:32). This signal peptide sequence or any other signal peptide sequence sharing the feature of TorA to target the protein to which it is a part of to the Tat transporter can be used in the vectors of the present invention (for example as described in the interpro entry IPR006311 or Bendtsen et al., 2005, BMC Bioinformatics 6:167). In the Tor A wild-type leader sequence above, the twin-arginine consensus motif is underlined and signal peptides comprising this sequence can be used in the vectors of the invention providing that targeting to the Tat pathway is retained.

A particularly preferred signal peptide for use in the present invention is the Tor AB7 signal peptide (MNNNDLFQTSRQRFLAQLGGLTVAGMLGPSLLTPR-RAT, SEQ ID NO:2) which has been engineered for improved periplasmic targeting of proteins via the Tat pathway compared to the wild-type TorA signal peptide. The Tor AB7 signal peptide has or comprises the sequence TSR QRFLA (SEQ ID NO:34) wherein the underlined residues are the residues which differ from the wild-type TorA signal sequence, and signal peptides comprising this sequence are particularly preferred providing that targeting to the Tat pathway is retained.

Alternatively, the TorA B6, E2, F1, F11 or H2 mutants as disclosed in Table II of DeLisa et al., supra, may also be used.

Thus, a preferred signal peptide for use in the present invention is the Tor AB6 signal peptide (MNNNDLFQTSRRRLLAQLGGLTVAGMLGPSLLTPR-RAT, SEQ ID NO:35) which has been engineered for improved periplasmic targeting of proteins via the Tat pathway compared to the wild-type TorA signal peptide. The Tor AB6 signal peptide has or comprises the sequence TSRRR LLA, SEQ ID NO:36, wherein the underlined residues are the residues which differ from the wild-type TorA signal sequence, and signal peptides comprising this sequence are particularly preferred providing that targeting to the Tat pathway is retained.

Thus, a preferred signal peptide for use in the present invention is the Tor AE2 signal peptide (MNNNDIFQAS-RRRFLAQPGGLTVAGMLGPSLLTPRRAT, SEQ ID NO:37) which has been engineered for improved periplasmic targeting of proteins via the Tat pathway compared to the wild-type TorA signal peptide. The Tor AE2 signal peptide has or comprises the sequence IFQASRRRFLAQP, SEQ ID NO:38, wherein the underlined residues are the residues which differ from the wild-type TorA signal sequence, and signal peptides comprising this sequence are particularly preferred providing that targeting to the Tat pathway is retained.

Thus, a preferred signal peptide for use in the present invention is the Tor AF1 signal peptide (MNNNELFQAS-RRRFLAQLGGLTVAGMLGPSLLTPRRAT, SEQ ID NO:39) which has been engineered for improved periplasmic targeting of proteins via the Tat pathway compared to the wild-type TorA signal peptide. The Tor AF1 signal peptide has or comprises the sequence ELFQASRRRFLA, SEQ ID NO:40, wherein the underlined residues are the residues which differ from the wild-type TorA signal sequence, and signal peptides comprising this sequence are particularly preferred providing that targeting to the Tat pathway is retained.

Thus, a preferred signal peptide for use in the present invention is the Tor AF11 signal peptide (MNNNDLFQT-TRRRFLAQLGGLTVAGMLGPSLLTPRRAT, SEQ ID NO:41) which has been engineered for improved periplasmic targeting of proteins via the Tat pathway compared to the wild-type TorA signal peptide. The Tor AF11 signal peptide has or comprises the sequence TTRRRFLA, SEQ ID NO:42, wherein the underlined residues are the residues which differ from the wild-type TorA signal sequence, and signal peptides comprising this sequence are particularly preferred providing that targeting to the Tat pathway is retained.

Thus, a preferred signal peptide for use in the present invention is the Tor AH2 signal peptide (MNNNDSFQTSRRRFLAQLGGLTVAGMLGPSLLTPR-RAT, SEQ ID NO:43) which has been engineered for improved periplasmic targeting of proteins via the Tat pathway compared to the wild-type TorA signal peptide. The Tor AH2 signal peptide has or comprises the sequence SFQ TSRRRFLA, SEQ ID NO:44, wherein the underlined residues are the residues which differ from the wild-type TorA signal sequence, and signal peptides comprising this sequence are particularly preferred providing that targeting to the Tat pathway is retained.

In addition, further derivatives or variants from the above signal peptides, in particular the Tor AB7 signal peptide, can be used in the vectors of the invention providing that such derivative or variant sequences display retained or improved ability to direct proteins into the Tat pathway. The ability to direct proteins into the Tat pathway can readily be verified using any convenient technique, for example using *E. coli* tatC and tatAE mutant strains, or for example using the protein reporter assay as described in DeLisa et al., supra.

Appropriate variants might comprise signal peptides which comprise or consist of an amino acid sequence, or a nucleotide sequence encoding an amino acid sequence, with a sequence identity of at least 70%, 75% or 80% to the above-mentioned signal peptide sequences, such as at least 80%, 81%, 82%, 83%, 84%, 85%, 86%, 87%, 88%, 89%, 90%, 91%, 92%, 93%, 94%, 95%, 96%, 97%, 98%, or 99% identity. These variant sequences should retain or have the functional property to act as a signal peptide which can direct proteins into the Tat secretory pathway. Functional truncations or fragments of these sequences (or these homologous sequences) could also be used providing the ability to encode a protein which retains or has the functional property to act as a signal peptide is retained. Other preferred examples of mutated signal peptides are sequences containing up to 6, e.g. up to 5, 4, 3, 2, or 1 altered amino acids in the above signal peptides.

In embodiments outlined elsewhere herein, where the vectors of the invention can encode a second, non-pVIII, phage coat protein fusion, e.g. a second (different) phage coat protein fused to a protein of interest (POI), then in some of these embodiments another type of (i.e. a non-Tat) signal sequence can be used with (can be operably linked to) the non-pVIII phage coat protein fusion, or no signal sequence may be used, e.g. with a POI-pIX fusion a signal sequence need not be used and is sometimes preferably not used. In embodiments where no signal sequence is used, e.g. with a POI-pIX fusion construct, then such pIX fusion proteins will generally be directed into the YidC pathway. In embodiments where a non-Tat signal sequence is used then the non-pVIII phage coat protein fusion will be directed into a non-Tat secretory pathway as determined by the nature of the chosen signal sequence, e.g. into the Sec secretory pathway.

In the vectors of the invention, the sequence encoding the signal peptide (the Tat signal peptide) is linked, e.g. operably linked, to the sequence encoding the fluorophore-pVIII fusion protein, such that it directs the fluorophore-pVIII fusion protein into the Tat secretory pathway.

The term "fusion protein", "fused", etc., is used herein to describe the functional joining of two or more protein components in the same polypeptide sequence or in the same open reading frame (ORF). Such fusion proteins can also be described as genetic fusions as they are encoded by the same nucleic acid sequence (sometimes called a "fusion gene" or "fusion nucleotide sequence"). Although two (or more) protein components (or encoding nucleic acid sequences) can be directly adjacent to each other in such a fusion protein, equally the components can be joined by appropriate peptide spacers or linkers. As is well known in the art, spacers or linkers can be important to allow each of the individual protein components to be expressed in a functional manner, e.g. allowing them to form the appropriate three-dimensional structure to perform or maintain their native function.

Thus, in the fusion proteins encoded by the vectors of the invention, a peptide spacer (or linker) is generally included between the fluorophore and the pVIII part of the fusion protein (sometimes referred to as the pVIII fusion protein) or between the protein of interest (POI) and the second phage coat protein. In other embodiments, such linkers or spacers need not be included, or may only be included in between some of the components. Thus, in the vectors of the present invention, the sequences encoding the fluorophore or the POI can be fused to the sequences encoding pVIII or other phage protein, respectively, with or without a spacer or linker sequence between the components. All these possibilities (i.e. fusion proteins or encoding nucleic acids with or without spacer or linker sequences) are still regarded as direct fusions or direct genetic fusions.

Although this discussion focuses on a linker or spacer between the phage coat proteins and the fluorophore or POI, linker sequences may be included elsewhere in the vectors of the invention as appropriate, e.g. between other components of the vectors as discussed herein, for example between the signal peptide and the fluorophore.

Thus, the term "pVIII fusion protein" refers to a pVIII protein (phage pVIII protein), or fragment thereof, fused to an exogenous peptide or protein, in this case a fluorophore. The terms "pIII fusion protein", "pVI fusion protein", "pVII fusion protein" or "pIX fusion protein" refer to a pIII, pVI, pVII or pIX protein (pIII, pVI, pVII or pIX phage protein) (as appropriate), or fragments thereof, fused to an exogenous peptide, e.g. a protein of interest (POI).

The vectors of the invention thus comprise a sequence (a nucleic acid sequence) encoding a fluorophore fused (genetically fused) to a sequence encoding a pVIII phage coat protein (sometimes referred to herein as fluorophore-pVIII). The fluorophore and the pVIII can be in any appropriate order or spacing in the vector providing that, once expressed and packaged into phage particles, a functional fusion protein between the fluorophore and the pVIII is formed wherein the pVIII component of the fusion protein forms part of the phage coat and the fluorophore is functionally expressed or displayed on the surface of the phage particle. The fluorophore part of the fusion protein is thus positioned in frame with the pVIII part of the fusion protein. This means that the fluorophore and the pVIII are expressed in the same polypeptide sequence, or, put another way, as a direct fusion. In the vectors of the invention it is generally preferred that the fluorophore component of the fusion protein be positioned N-terminally (or at or near the N-terminus) to the pVIII component of the fusion protein.

As the fluorophore is fused to the major phage coat protein, pVIII employing a classical (8+8 wild-type (phagemid) or 88 wild-type (genomic)) complementation expression approach, the final phage particle produced by using the vectors of the invention will have multiple copies of the fluorophore randomly distributed along the length of the phage particle, together with copies of the wild-type pVIII protein. As for example M13 phages have approximately 2700 copies of the major coat protein pVIII on their surface, many copies of the fluorophore can be present. Thus, such functional expression of the fluorophore can conveniently be assessed by monitoring for fluorescence, e.g. detectable fluorescence, by any appropriate and convenient assay. As shown in the Examples, such monitoring for fluorescence can conveniently be carried out either by monitoring for fluorescence in transformed host cells such as *E. coli*, e.g. using fluorescence microscopy, or by analysing samples of phage particles, e.g. liquid samples, for fluorescence using a plate reader or other convenient apparatus. FACS or FLISA analysis can also be used.

As having a genetic fusion between the fluorophore and the pVIII phage coat protein is important for the present invention, conveniently appropriate fluorophores will be biological fluorophores or other fluorophores which can be encoded by a nucleic acid sequence and thereby included in the vectors of the invention. Preferably such a fluorophore will also be intrinsically fluorescent or directly detectable. Fluorophores which can be activated or are bleachable may also be used.

Preferred fluorophores for use in the present invention are biological fluorophores having or comprising a β-barrel structure or architecture.

Such fluorophores would be well-known to a person skilled in the art (see for example the review by Shaner et al., 2007, J. Cell Sci, 120(24): 4247-4260) and include green fluorescent protein (GFP) or derivatives thereof with the same folding topology as GFP (also referred to as GFP derivatives). In other words, such fluorophores for use in the invention include green fluorescent protein (GFP) or fluorophore derivatives thereof having a β-barrel architecture or structure or a GFP-architecture. Such non-GFP fluorophores can conveniently be referred to as GFP-like fluorophores or GFP derivatives or fluorophores with GFP-architecture. Although green fluorescent proteins have now been isolated from multiple organisms, the term GFP traditionally and herein refers to the protein first isolated from the jellyfish *Aequorea victoria*. This wild-type protein has however been subject to various modifications to produce the wide variety of GFP derivatives or GFP-like fluorophores currently described in the literature.

Such fluorophores contain one or more β-barrels as a unit, for example may contain a single β-barrel (a β-barrel monomer) or multiple β-barrels, for example β-barrel homotetramers.

All such fluorophores have or comprise a similar 3-D cylindrical structure in which a large portion of the polypeptide backbone is wound into a β-barrel structure which generally comprises 11 strands of beta sheets that surround a central alpha helix containing the chromophore. The β-barrel structure forms a near-perfect cylinder creating what can be referred to as a "β-can" structure which characterises the GFP-like fluorophore family (GFP-derivatives). Thus, alternatively viewed, fluorophores which contain this "β-can" structure are also preferred for use in the present invention. This β-barrel cylinder is generally approximately 24 to 30 As wide and 40 to 42 As long.

The GFP family of fluorophores (GFP plus GFP variants or derivatives, or GFP-like fluorophores) includes the variants blue (BFP), cyan (CFP), and yellow (YFP), depending on the spectral emission profile, as well as green variants of the original GFP. Enhanced GFP (EGFP), enhanced CFP (ECFP) and enhanced YFP (EYFP) are further examples.

Although the GFP family of fluorophores (GFP plus GFP variants or derivatives, or GFP-like fluorophores or GFP related fluorophores) have some inherently different properties, e.g. emission colour, intensity of fluorescence and other properties such as stability (and indeed can be engineered so as to have such different properties), the presence and retention of the above described β-barrel structure or architecture means that they generally behave in a similar way. Thus, members of the GFP family of fluorophores (or variants thereof, e.g. functional variants with at least 70% sequence identity or other values as described elsewhere herein) are preferred fluorophores for use in the present invention.

The nucleic acid sequences encoding such fluorophores (and their amino acid sequences) are well known and described in the art and can readily be obtained from the literature or standard databases (see for example pfam entry PF01353 or Interpro entry IPR011584).

Some specific examples of appropriate fluorophores, or GFP-like fluorophores (or GFP-variant fluorophores), or β-barrel containing fluorophores, for use in the present invention are mNeonGreen (another green fluorescent protein with extremely bright yellow-green fluorescence, Shaner et al., 2013, Nature Methods, 10(5):407-409), mGFPmut2 (a FACS optimised version of GFP, Cormack et al., 1996, Gene 173:33-38), and mCherry (a red fluorescent protein, Shaner et al., 2004, Nat. Biotechnol., 22, 1567-1572). "m" standing for monomeric. Other examples might be EGFP (or ECFP or EYFP). Preferred fluorophores for use in the present invention are mNeonGreen, or a derivative or variant thereof, and GFP or a derivative or variant thereof, for example mGFPmut2 or some other derivative or variant, e.g. EGFP (Heim et al., 1995, Nature 373:663-664). A more preferred fluorophore for use in the present invention is mNeonGreen or a derivative or variant thereof.

mNeonGreen (Shaner et al., 2013, supra) is a bright monomeric green fluorescent protein derived from *Branchiostoma lanceolatum*. The original native protein from *Branchiostoma lanceolatum* is a tetramer and this has been modified (as described in Shaner et al., 2013, supra) to obtain the monomeric (m) NeonGreen (mNG) which is used in the present invention. The final mutant contains 21 substitutions relative to the tetrameric starter protein and has sharp excitation and emission peaks (at 506 nm and 517 nm). Thus, mNeonGreen can be imaged with essentially no loss of emission photons using standard green fluorescent protein band-pass or long-pass filter sets. The sequence of the synthetic construct for mNeonGreen has the GenBank accession code KC295282.1 and is repeated below for completeness. The nucleic acid sequence is 711 base pairs long (SEQ ID NO:45):

```
  1 atggtgagca agggcgagga ggataacatg gcctctctcc cagcgacaca tgagttacac
 61 atctttggct ccatcaacgg tgtggacttt gacatggtgg gtcagggcac cggcaatcca
121 aatgatggtt atgaggagtt aaacctgaag tccaccaagg gtgacctcca gttctccccc
181 tggattctgg tccctcatat cgggtatggc ttccatcagt acctgcccta ccctgacggg
241 atgtcgcctt tccaggccgc catggtagat ggctccggat accaagtcca tcgcacaatg
301 cagtttgaag atggtgcctc ccttactgtt aactaccgct acacctacga gggaagccac
361 atcaaaggag aggcccaggt gaaggggact ggtttccctg ctgacggtcc tgtgatgacc
421 aactcgctga ccgctgcgga ctggtgcagg tcgaagaaga cttacccccaa cgacaaaacc
481 atcatcagta cctttaagtg gagttacacc actggaaatg gcaagcgcta ccggagcact
541 gcgcggacca cctacacctt tgccaagcca atggcggcta actatctgaa gaaccagccg
601 atgtacgtgt tccgtaagac ggagctcaag cactccaaga ccgagctcaa cttcaaggag
661 tggcaaaagg cctttaccga tgtgatgggc atggacgagc tgtacaagta a
```

The protein identifier for the encoded protein is AGG56535.1, which has the sequence as outlined below (236 amino acids, SEQ ID NO:46):

```
  1 mvskgeednm aslpathelh ifgsingvdf dmvgqgtgnp
    ndgyeelnlk stkgdlqfsp
 61 wilvphigyg fhqylpypdg mspfqaamvd gsgyqvhrtm
    qfedgasltv nyrytyegsh
121 ikgeaqvkgt gfpadgpvmt nsltaadwcr skktypndkt
    iistfkwsyt tgngkryrst
181 arttytfakp maanylknqp myvfrktelk hsktelnfke
    wqkaftdvmg mdelyk
```

In embodiments of the invention where the vector encodes the mNeonGreen fluorophore, the nucleic acid sequence as outlined above can be incorporated into the vectors of the invention. As in the vectors of the invention the sequence encoding the mNeonGreen is encoded as a fusion protein downstream of a signal peptide, then the mNeonGreen nucleotide sequence incorporated in the vectors of the invention conveniently has the initial start codon (atg) and stop codon (taa) removed.

In preferred embodiments of the invention a codon optimised version of this nucleic acid sequence is used which has been optimised for bacterial expression, e.g. in *E coli*. Although any appropriate codon optimised version can be used, a specific sequence for a codon optimised version of mNeonGreen which can be used in the present invention is outlined below. (Again the start and stop codons have been omitted for better incorporation into the vectors).

(SEQ ID NO: 3)
GTTTCTAAAGGTGAAGAAGACAACATGGCTTCTCTGCCGGCTACCCACGA

ACTGCACATCTTCGGTTCTATCAACGGTGTTGACTTCGACATGGTTGGTC

AGGGTACCGGTAACCCGAACGACGGTTACGAAGAACTGAACCTGAAATCT

ACCAAAGGTGACCTGCAGTTCTCTCCGTGGATCTTAGTTCCGCACATCGG

TTACGGTTTCCACCAGTACCTGCCGTACCCGGACGGTATGTCTCCGTTCC

AGGCTGCTATGGTTGACGGTTCTGGTTACCAGGTTCACCGTACCATGCAG

TTCGAAGACGGTGCTTCTCTGACCGTTAACTACCGTTACACCTACGAAGG

TTCTCACATCAAAGGTGAAGCTCAGGTTAAAGGTACCGGTTTCCCGGCTG

ACGGTCCGGTTATGACCAACTCTCTGACCGCTGCTGACTGGTGCCGTTCT

AAAAAAACCTACCCGAACGACAAAACCATCATCTCTACCTTCAAATGGTC

TTACACCACCGGTAACGGTAAACGTTACCGTTCTACCGCTCGTACCACCT

ACACCTTCGCTAAACCGATGGCTGCTAACTACCTGAAAAACCAGCCGATG

TACGTTTTCCGTAAAACCGAACTGAAACACTCTAAAACCGAACTGAACTT

CAAAGAATGGCAGAAAGCTTTCACCGACGTTATGGGTATGGACGAACTGT

ACAAA

These codon optimised versions all encode the same amino acid sequence as AGG56535.1 above. However, because the nucleotide sequence encoding the initial Methionine residue is omitted, the encoded amino acid sequence is:

(SEQ ID NO: 4)
VSKGEEDNM ASLPATHELH IFGSINGVDF DMVGQGTGNP

NDGYEELNLK STKGDLQFSP WILVPHIGYG FHQYLPYPDG

MSPFQAAMVD GSGYQVHRTM QFEDGASLTV NYRYTYEGSH

IKGEAQVKGT GFPADGPVMT NSLTAADWCR SKKTYPNDKT

IISTFKWSYT TGNGKRYRST ARTTYTFAKP MAANYLKNQP

MYVFRKTELK HSKTELNFKE WQKAFTDVMG MDELYK.

As set out above, and as discussed in more detail elsewhere herein, in other embodiments of the invention the vector comprises a sequence encoding a derivative or variant of the mNeonGreen (mNG) fluorophore, e.g. a derivative or variant of SEQ ID NO:4 or 46, or a derivative or variant of SEQ ID NO:45 or 3.

Thus, in other embodiments, the encoded mNG fluorophore comprises or consists of an amino acid sequence with a sequence identity of at least 70%, 75% or 80% to that of SEQ ID NO: 4, such as at least 80%, 81%, 82%, 83%, 84%, 85%, 86%, 87%, 88%, 89%, 90%, 91%, 92%, 93%, 94%, 95%, 96%, 97%, 98%, or 99% identity. These variant mNG sequences should retain or have the functional property to act as a fluorophore. Functional truncations or fragments of SEQ ID NO:4 (or these homologous sequences) or other mNG sequences, could also be used providing the ability to encode a protein which retains or has the functional property to act as a fluorophore is retained.

Equally the nucleic acid molecule encoding the mNG fluorophore may comprise or consist of a nucleotide sequence with a sequence identity of at least 70%, 75% or 80% to that of SEQ ID NO: 45 or 3, such as at least 80%, 81%, 82%, 83%, 84%, 85%, 86%, 87% 88% 89% 90% 91%, 92%, 93% 94% 95% 96% 97% 98% or 99% identity. These variant mNG nucleotide sequences should encode a protein which retains or has the functional property to act as a fluorophore. Functional truncations or fragments of SEQ ID NO:45 or 3 (or these homologous sequences) or other mNG sequences, could also be used providing the ability to encode a protein which retains or has the functional property to act as a fluorophore is retained.

The term "pVIII phage coat protein" or "pVIII protein" or "pVIII phage protein" or "pVIII coat protein", etc., as used herein refers to a pVIII protein originating from or derived from a filamentous phage (wild-type or native sequence), or a pVIII protein with a sequence which corresponds to the sequence of such a pVIII protein. Preferred filamentous phages from which the pVIII protein is derived or the pVIII protein corresponds to are M13, fd, and f1 phages. Any appropriate pVIII protein can be used providing it has the ability to display a fluorophore as a pVIII fusion protein. Preferably the pVIII protein encoded by the vectors of the invention corresponds to the mature (full length) pVIII protein, i.e. lacks the pVIII signal peptide. Preferably, the pVIII proteins encoded by the vectors of the invention comprise or consist of the following amino acid sequence, which corresponds to the wild-type (full length) mature pVIII protein from the M13 filamentous phage without its signal sequence.

(SEQ ID NO: 8)
AEGDDPAKAAFNSLQASATEYIGYAWAMVVVIVGATIGIKLFKKFTSKAS

An exemplary nucleic acid sequence encoding this sequence for inclusion in the vectors is provided elsewhere herein as SEQ ID NO:7.

In other embodiments the encoded pVIII protein comprises or consists of an amino acid sequence with a sequence identity of at least 70%, 75% or 80% to that of SEQ ID NO: 8, such as at least 80%, 81%, 82%, 83%, 84%, 85%, 86%, 87%, 88%, 89%, 90%, 91%, 92%, 93%, 94%, 95%, 96%, 97%, 98%, or 99% identity. As indicated above, these variant pVIII sequences should retain or have the functional ability to display a fluorophore as a pVIII fusion protein. Functional truncations or fragments of SEQ ID NO:8 (or these homologous sequences) or other pVIII sequences, could also be used providing the ability to display a fluorophore as a pVIII fusion protein was retained.

Equally the nucleic acid molecule encoding the pVIII protein comprises or consists of a nucleotide sequence with a sequence identity of at least 70%, 75% or 80% to that of SEQ ID NO: 7, such as at least 80%, 81%, 82%, 83%, 84%, 85%, 86%, 87%, 88%, 89%, 90%, 91%, 92%, 93%, 94%, 95%, 96%, 97%, 98%, or 99% identity. These variant pVIII nucleotide sequences should retain or have the functional ability to encode a fluorophore as a pVIII fusion protein which could be displayed on a phage particle. Functional truncations or fragments of SEQ ID NO:7 (or these homologous sequences) or other pVIII sequences, could also be used providing the ability to encode a fluorophore as a pVIII fusion protein which could be displayed on a phage particle was retained.

Preferred pVIII variants have a valine to isoleucine mutation at, or corresponding to, position 33 of SEQ ID NO:8

(i.e. have an isoleucine residue at, or corresponding to, position 33 of SEQ ID NO:8), or have an ATA isoleucine codon at, or corresponding to, residues 97-99 of SEQ ID NO:7, as described elsewhere herein. A particularly preferred pVIII variant is the pVIII sequence as found in the F03 clone as described elsewhere herein. Preferred pVIII fragments or truncations are functional fragments or truncations which include the residue corresponding to position 33 of SEQ ID NO:8 at the amino acid or nucleotide level.

As described elsewhere herein, in some embodiments the vectors of the invention encode other non-pVIII phage coat proteins such as pIII, pVI, pVII or pIX coat proteins.

The term "pIII phage coat protein" or "pIII protein" or "pIII phage protein" or "pIII coat protein", etc., as used herein refers to a pIII protein originating from or derived from a filamentous phage (wild-type or native sequence), or a pIII protein with a sequence which corresponds to the sequence of such a pIII protein. Preferred filamentous phages from which the pIII protein is derived or the pIII protein corresponds to are M13, fd, and f1 phages. Any appropriate pIII protein can be used providing it has the ability to display a POI as a pIII fusion protein. Preferably the pIII protein encoded by the vectors of the invention corresponds to the mature pIII protein, i.e. lacks the pIII signal peptide. Preferably, the pIII proteins encoded by the vectors of the invention comprise or consist of the following amino acid sequence, which corresponds to the wild-type mature pIII protein from the M13 filamentous phage without its signal sequence (see also (Genbank AY598820.1).

>pIII_1

(SEQ ID NO: 12)
AETVESCLAKPHTENSFTNVWKDDKTLDRYANYEGCLWNATGVVVCTGDE

TQCYGTWVPIGLAIPENEGGGSEGGGSEGGGSEGGGTKPPEYGDTPIPGY

TYINPLDGTYPPGTEQNPANPNPSLEESQPLNTFMFQNNRFRNRQGALTV

YTGTVTQGTDPVKTYYQYTPVSSKAMYDAYWNGKERDCAFHSGENEDPFV

CEYQGQSSDLPQPPVNAGGGSGGGSGGGSEGGGSEGGGSEGGGSEGGGSG

GGSGSGDFDYEKMANANKGAMTENADENALQSDAKGKLDSVATDYGAAID

GFIGDVSGLANGNGATGDFAGSNSQMAQVGDGDNSPLMNNFRQYLPSLPQ

SVECRPFVFGAGKPYEFSIDCDKINLFRGVFAFLLYVATFMYVFSTFANI

LRNKES

An exemplary nucleic acid sequence encoding this amino acid sequence for inclusion in the vectors is provided below as SEQ ID NO:11.

(SEQ ID NO: 11)
GCTGAAACTGTTGAAAGTTGTTTAGCAAAACCCCATACAGAAAATTCATT

TACTAACGTCTGGAAAGAGACAAAACTTTAGATCGTTACGCTAACTATGA

GGGCTGTCTGTGGAATGCTACAGGCGTTGTAGTTTGTACTGGTGACGAAA

CTCAGTGTTACGGTACATGGGTTCCTATTGGGCTTGCTATCCCTGAAATG

AGGGTGGTGGCTCTGAGGGTGGCGGTTCTGAGGGTGGCGGTTCTGAGGGT

GGCGGTACTAAACCTCCTGAGTACGGTGATACACCTATTCCGGGCTATAC

TTATATCAACCCTCTCGACGGCACTTATCCCCCTGGTACTGAGCAAAACC

CCCCATCCTAATCCTTCTCTTGAGGAGTCTCAGCCTCTTAATACTTTCAT

GTTTCAGAATAATAGGTTCCGAAATAGGCAGGGGGCATTAACTGTTTATA

CGGGCACTGTTACTCAAGGCACTGACCCCGTTAAAACTTATTACCAGTAC

ACTCCTGTATCATCAAAAGCCATGTATGACGCTTACTGGAACGGTAAATT

CAGAGACTGCGCTTTCCATTCTGGCTTTAATGAGGATCCATTCGTTTGTG

AATATCAAGGCCAATCGTCTGACCTGCCTCAACCTCCTGTCAATGCTGGC

GGCGGCTCTGGTGGTGGTTCTSGTGGCGGCTCTGAGGGTGGTGGCTCTGA

GGGTGGCGGTTCTGAGGGTGGCGGCTCTGAGGGAGGCGGTTCCGGTGGTG

GCTCTGGTTCCGGTGATTTTATTATGAAAAGATGGCAAACGCTAATAAGG

GGGCTATGACCGAAAATGCCGATGAAAACGCGCTACAGTCTGACGCTAAA

GGCAAACTTGATTCTGTCGCTACTGATTACGGTGCTGCTATCGATGGTTT

CATTGGTGACGTTTCCGGCCTTGCTAATGGTAATGGTGCTACTGGTGATT

TTGCTGGCTCTAATTCCCAAATGGCTCAAGTCGGTGACGGTGATAATTCA

CCTTTAATGAATAATTTCCGTCAATATTTACCTTCCCTCCCTCAATCGGT

TGAATGTCGCCCTTTTGTCTTTGGCGCTGGTAAACCATATGAATTTTCTA

TTGATTGTGACAAAATAAACTTATTCCGTGGTGTCTTTGCGTTTCTTTTA

TATGTTGCCACCTTTATGTATGTATTTTCTACGTTTGCTAACATACTGCG

TAATAAGGAGTCTTAA

In other embodiments the encoded pIII protein comprises or consists of an amino acid sequence with a sequence identity of at least 70%, 75% or 80% to that of SEQ ID NO: 12, such as at least 80%, 81%, 82%, 83%, 84%, 85%, 86%, 87%, 88%, 89%, 90%, 91%, 92%, 93%, 94%, 95%, 96%, 97%, 98%, or 99% identity. These variant pIII sequences should retain or have the functional ability to display a POI as a pIII fusion protein. Functional truncations or fragments of SEQ ID NO:12 (or these homologous sequences) or other pIII sequences, could also be used providing the ability to display a POI as a pIII fusion protein was retained. Examples of appropriate truncated pIII proteins for display, e.g. truncations containing only the C-terminal portion of pIII are well known and described in the art.

The term "pVI phage coat protein" or "pVI protein" or "pVI phage protein" or "pVI coat protein", etc., as used herein refers to a pVI protein originating from or derived from a filamentous phage (wild-type or native sequences), or a pVI protein with a sequence which corresponds to the sequence of such a pVI protein. Preferred filamentous phages from which the pVI protein is derived or the pVI protein corresponds to are M13, fd, and f1 phages. Any appropriate pVI protein can be used providing it has the ability to display a POI as a pVI fusion protein. Preferably, the pVI proteins encoded by the vectors of the invention comprise or consist of the following amino acid sequence, which corresponds to the pVI protein from the VCSM13 helper phage (Genbank AY598820.1).

(SEQ ID NO: 13)
MPVLLGIPLLLRFLGFLLVTLFGYLLTFLKKGFGKIAIAISLFLALIIGL

NSILVGYLSDISAQLPSDFVQGVQLILPSNALPCFYVILSVKAAIFIFDV

KQKIVSYLDWDK

In other embodiments the encoded pVI protein comprises or consists of an amino acid sequence with a sequence identity of at least 70%, 75% or 80% to that of SEQ ID NO:

13, such as at least 80%, 81%, 82%, 83%, 84%, 85%, 86%, 87%, 88%, 89%, 90%, 91%, 92%, 93%, 94%, 95%, 96%, 97%, 98%, or 99% identity. These variant pVI sequences should retain or have the functional ability to display a POI as a pVI fusion protein. Functional truncations or fragments of SEQ ID NO:13 (or these homologous sequences) or other pVI sequences, could also be used providing the ability to display a POI as a pVI fusion protein was retained.

The term "pVII phage coat protein" or "pVII protein" or "pVII phage protein" or "pVII coat protein", etc., as used herein refers to a pVII protein originating from or derived from a filamentous phage (wild-type or native sequences), or a pVII protein with a sequence which corresponds to the sequence of such a pVII protein. Preferred filamentous phages from which the pVII protein is derived or the pVII protein corresponds to are M13, fd, and f1 phages. Any appropriate pVII protein can be used providing it has the ability to display a POI as a pVII fusion protein. Preferably, the pVII proteins encoded by the vectors of the invention comprise or consist of the following amino acid sequence, which corresponds to the wild-type pVII protein from the VCSM13 helper phage (Genbank AY598820.1).

(SEQ ID NO: 14)
MEQVADFDTIYQAMIQISVVLCFALGIIAGGQR

In other embodiments the encoded pVII protein comprises or consists of an amino acid sequence with a sequence identity of at least 70%, 75% or 80% to that of SEQ ID NO: 14 such as at least 80%, 81%, 82%, 83%, 84%, 85%, 86%, 87%, 88%, 89%, 90%, 91%, 92%, 93%, 94%, 95%, 96%, 97%, 98%, or 99% identity. These variant pVII sequences should retain or have the functional ability to display a POI as a pVII fusion protein. Functional truncations or fragments of SEQ ID NO:14 (or these homologous sequences) or other pVII sequences, could also be used providing the ability to display a POI as a pVII fusion protein was retained.

The term "pIX phage coat protein" or "pIX protein" or "pIX phage protein" or "pIX coat protein", etc., as used herein refers to a pIX protein originating from or derived from a filamentous phage (wild-type or native sequences), or a pIX protein with a sequence which corresponds to the sequence of such a pIX protein. Preferred filamentous phages from which the pVII protein is derived or the pIX protein corresponds to are M13, fd, and f1 phages. Any appropriate pIX protein can be used providing it has the ability to display a POI as a pIX fusion protein. Preferably the pIX protein encoded by the vectors of the invention corresponds to the pIX protein. Preferably, the pIX proteins encoded by the vectors of the invention comprise or consist of the following amino acid sequence, which corresponds to the wild-type pIX protein from the VCSM13 helper phage (Genbank AY598820.1).

(SEQ ID NO: 15)
MSVLVYSFASFVLGWCLRSGITYFTRLMETSS

In other embodiments the encoded pIX protein comprises or consists of an amino acid sequence with a sequence identity of at least 70%, 75% or 80% to that of SEQ ID NO: 15, such as at least 80%, 81%, 82%, 83%, 84%, 85%, 86%, 87%, 88%, 89%, 90%, 91%, 92%, 93%, 94%, 95%, 96%, 97%, 98%, or 99% identity. These variant pIX sequences should retain or have the functional ability to display a POI as a pIX fusion protein. Functional truncations or fragments of SEQ ID NO:15 (or these homologous sequences) or other pIX sequences, could also be used providing the ability to display a POI as a pIX fusion protein was retained.

In the present invention, "sequence identity" is a measure of identity between proteins at the amino acid level and a measure of identity between nucleic acids at the nucleotide level. The protein sequence identity may be determined by comparing the amino acid sequence in a given position in each sequence when the sequences are aligned. Similarly, the nucleic acid sequence identity may be determined by comparing the nucleotide sequence in a given position in each sequence when the sequences are aligned. When variant or derivative molecules are referred to herein, for example by percent identity values, e.g. at least 70%, etc., then it should be understood that such variants or derivatives are generally functional variants or derivatives, i.e. display retained or improved function.

Methods to determine the percentage identity of two amino acid sequences or of two nucleic acid sequences are well known and described in the art, and any of these may be used. For example, to determine the percent identity of two amino acid sequences or of two nucleic acid sequences, the sequences are aligned for optimal comparison purposes (e.g., gaps may be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In some embodiments the two sequences are the same length.

One may manually align the sequences and count the number of identical amino acids. Alternatively, alignment of two sequences for the determination of percent identity may be accomplished using a mathematical algorithm. Such an algorithm is incorporated into the NBLAST and XBLAST programs of (Altschul et al. 1990). BLAST nucleotide searches may be performed with the NBLAST program, score=100, wordlength=12, to obtain nucleotide sequences homologous to a nucleic acid molecules of the invention. BLAST protein searches may be performed with the XBLAST program, score=50, wordlength=3 to obtain amino acid sequences homologous to a protein molecule of the invention. To obtain gapped alignments for comparison purposes, Gapped BLAST may be utilised. Alternatively, PSI-Blast may be used to perform an iterated search which detects distant relationships between molecules. When utilising the NBLAST, XBLAST, and Gapped BLAST programs, the default parameters of the respective programs may be used. See http://www.ncbi.nlm.nih.gov. Alternatively, sequence identity may be calculated after the sequences have been aligned e.g. by the BLAST program in the EMBL database (www.ncbi.nlm.gov/cgi-bin/BLAST). Generally, the default settings with respect to e.g. "scoring matrix" and "gap penalty" may be used for alignment. In the context of the present invention, the BLASTN and PSI BLAST default settings may be advantageous. In calculating percent identity, only exact matches are counted.

In preferred embodiments of the invention one or more ribosome (ribosomal) binding sites (RBS) are included in the vector constructs. Such components can also be referred to as a translational initiation region (TIR).

The RBS sequence is located in the vector at an appropriate position for the RBS sequence to function. The role of the RBS is to recruit a ribosome during the initiation of protein translation and thus is conveniently placed at an appropriate distance upstream from the start codon of the protein it is desired to translate, or upstream of the ORF for the protein it is desired to translate. Thus, in the vectors of the present invention, the RBS sequence is conveniently placed upstream of the sequence encoding the signal peptide (in embodiments where a signal peptide is part of the ORF, e.g. for the fluorophore-pVIII fusion protein). In embodiments where no signal peptide is present in the ORF, e.g. in some embodiments where a POI is fused to a second non-pVIII coat protein, then the RBS sequence is conveniently placed at an appropriate distance upstream of the sequence encoding the POI or the coat protein. The appropriate distance would be known or readily determined by a person skilled in the art depending on the RBS chosen. Exemplary distances might be seven or eight nucleotides from the ATG start codon, but this can vary.

The RBS/TIR sequence modulates the translation intensity (level of protein expression) of the sequences located downstream and different types of RBS can produce different levels of protein expression, for example weak or strong expression. Weak or strong RBS/TIR sequences are well known in the art and can readily be selected by a skilled person depending on the level of protein expression desired. As expected, a strong RBS facilitates or induces more translation (strong translation) as compared to a weak RBS. As will be explained in more detail below, in preferred embodiments of the invention, a weak RBS is used, in particular to drive the translation of the fluorophore-pVIII fusion protein.

In particular, in preferred vectors of the invention an RBS is included upstream (or 5' or N-terminal to) to the start codon of the sequence encoding the signal peptide which directs proteins into the Tat secretory pathway. A preferred RBS for use in the present invention is a Shine Dalgarno (SD) sequence or a SD based sequence which can be included in the vector constructs. SD sequences are well known and described in the art and any of these may be used. For example the core SD sequence is GAGG (SEQ ID NO:47) and other consensus sequences are AGGAGG (SEQ ID NO:48) or AGGAGGU (SEQ ID NO:49). Thus, SD sequences comprising these core or consensus sequences can be used.

Weak or strong SD sequences are well known in the art and can readily be selected by a skilled person in order to control the level or amount of protein expression for any given ORF. For example, a strong SD will be able to bind well to a ribosome. Such a strong SD will generally contain the SD core sequence or one of the consensus sequences outlined above exactly, or with very few changes, and/or for example will contain a number of A and/or G residues close by. Alternatively, a strong SD can be obtained by the insertion of other components in conjunction with an SD core or consensus sequence (or a highly related sequence). Such additional components would be well-known to a person skilled in the art, for example a classical or consensus SD sequence can be used in conjunction with an Epsilon sequence (e.g. TTAACTTTA, SEQ ID NO:50). For example, in the present invention a preferred strong SD is the T7g10 TIR (Olins et al., 1988, Gene 73:227-235) which also includes an Epsilon sequence (e.g. TTAACTTTA, SEQ ID NO:50). Thus, in specific examples of the vectors of the invention where a strong SD is used, the upstream region from the ATG start site of the Tat signal peptide may have the sequence <u>TTAACTTTA</u>AGAAGGAGATATACAT, SEQ ID NO:31 (Epsilon sequence underlined and SD consensus sequence in bold). However, other strong SD/TIR sequences could be readily selected by a person skilled in the art.

In contrast, a weak SD sequence will generally contain sequences which are more different to the core or consensus SD sequences outlined herein. A weak SD sequence will still be able to bind to a ribosome but at a lower level or lower efficiency. For example, a weak SD sequence for use in the present invention may contain one or two modifications from the core consensus SD sequences outlined herein. A preferred weak SD sequence for use in the vectors of the present invention comprises or consists of AGGAGA, SEQ ID NO:30 (i.e. contains one nucleotide difference from the consensus sequence AGGAGG, SEQ ID NO:48). This weak SD sequence is preferably placed eight nucleotides from the ATG start site, although this distance can sometimes be varied as discussed above. Thus, in specific examples of the vectors of the invention where a weak SD is used, the upstream region from the ATG start site of the Tat signal peptide may have the sequence AAGGAGACAGTCATA, SEQ ID NO:51 (variant SD sequence shown in bold). However, other weak SD/TIR sequences could be readily selected by a person skilled in the art.

As expected, a strong SD facilitates or induces more translation (strong or high translation) as compared to a weak SD which will facilitate or induce a low amount (or weak or less efficient) translation.

Either a strong or a weak RBS or SD sequence can be used in the vector constructs of the invention. One of the aims of the invention is to increase the fluorescence of a phage particle by increasing the number of fluorophore-pVIII fusion proteins incorporated into the coat (on the surface) of the phage. This would generally favour the use of a strong SD sequence in order to obtain more translation. Thus, it is somewhat surprising that in some embodiments a weak SD (or weak RBS) sequence produces better results, e.g. in terms of better functional display of the fluorophore-pVIII fusion protein, or increased display (e.g. more copies per particle) of the fluorophore-pVIII fusion protein, preferably resulting in an increased fluorescence of phage particles.

Thus, in some embodiments the use of a weak SD (or weak RBS) sequence in the vector construct upstream of the sequence encoding the ORF comprising the Tat signal peptide and the fluorophore-pVIII fusion protein is preferred. In other words, the RBS (or SD) controlling or driving translation of the Tat signal peptide and hence the fluorophore-pVIII fusion protein is a weak SD (or weak RBS). Preferably the use of such a weak SD sequence results in more copies of the intact fluorophore-pVIII fusion protein incorporated in the coat of the phage when compared to a construct where a strong SD (or strong RBS) is used or when a consensus SD sequence, e.g AGGAGG (or other consensus sequences as defined above), is used.

Indeed, vector constructs where the translation efficiency of the fluorophore-pVIII fusion protein is low, weak, reduced, or non-optimal are generally preferred. For example, preferred modifications/variant molecules as described elsewhere herein are those in which translation efficiency or speed, for example and in particular of the fluorophore-pVIII fusion protein, is reduced or significantly reduced, for example compared to the original parent sequence. Preferably such reduced or weak (or decreased) translation efficiency or speed also results in more copies of the fluorophore-pVIII fusion protein on the surface of the phage and/or an increased number of functional fluorophores on the surface of the phage, and thus increased fluorescence.

In preferred embodiments of the invention, although optional, one or more tags, e.g. protein or peptide tags, can be included in the vector constructs. Such tags can conveniently be used for detection and thus, in these embodiments, any detectable tag could be used. The tags can also be used for other purposes such as enrichment of tag-containing fusion proteins, for example before screening of phage fluorescence, e.g. by FACS, takes place. Antigen peptide tags (or epitope tags) such as FLAG, c-myc, HA (haemaglutinin), HIS, HAT or V5 tags are particularly preferred for use in embodiments of the invention when FACS techniques or other fluorescent detection techniques are used, as these tags readily allow labelling by using known and readily available fluorescently labelled antibodies against the specific tag. Other antigen peptide tags known in the art can equally be used.

A FLAG tag is a preferred tag for use in the vectors of the present invention. The FLAG tag is an octapeptide tag and comprises the sequence DYKDDDDK (SEQ ID NO:10). FLAG tag derivatives can also be used, which are well known and standard in the art. In addition, antibodies which can recognise the various FLAG tags and can thus be fluorescently labelled and used for detection of the FLAG tag are also well described in the art, e.g. M1 and M2 antibodies.

Other tags for use in the present invention (either as an alternative or in addition to an antigen peptide tag, and in particular a FLAG tag) are biotin tags which can for example be captured by binding to streptavidin or avidin or avidin-like molecules on a solid phase or can be labeled, e.g. fluorescently labeled, by using a fluorescently labeled form of streptavidin or avidin or avidin-like molecules. Appropriate biotin tags for use in the constructs of the present invention would be well known to a skilled person. Biotin tags for use in the methods of the present invention may comprise biotin molecules per se, e.g. biotin molecules which are attached, e.g. via chemical conjugation, to the expressed fluorophore-pVIII fusion protein on the phage surface. Methods for attaching such biotin tags are well known in the art.

Alternatively, the biotin tags may comprise moieties, e.g. peptides, which can act as substrates for biotinylation reactions and thereby become attached to biotin molecules. Such peptide tags can readily be incorporated into the vectors of the invention. For example, an exemplary biotin tag for use in the present invention is AviTag™ (MSGLNDIFEAQK-IEWHE, SEQ ID NO:52), which is a commercially available tag from Avidity LLC, Aurora, Colo., USA which becomes biotinylated in vitro or in vivo by biotin ligase.

Another example of a preferred biotin tag is Strep-tag, which is also commercially available from IBA GmbH, Gottingen, Germany, and which is capable of binding to the biotin binding pocket of streptavidin. Preferably, the Strep-tag comprises the 8 amino acid sequence Trp-Ser-His-Pro-Gln-Phe-Glu-Lys (WSHPQFEK, SEQ ID NO:53). Any other protein or peptide tags which are capable of binding to streptavidin or avidin could equally be used.

Combinations of one or more of the above tags could be used to label the phage particles so that multiple labels are present.

Preferred tags are protein tags or peptide tags which can readily be incorporated into the vector constructs (e.g. phage display constructs) of the invention, e.g. using standard recombinant and cloning techniques.

The tag sequence can be located in the vector at any appropriate position for the tag to function, e.g. to be expressed and to be detectable. Such tags can thus be internal, N-terminal or C-terminal to the part of the construct which is being tagged and which is to be detected using the tag. In the present invention a tag can conveniently be used to detect expression of the fluorophore-pVIII part of the construct. Thus, the tag can conveniently be placed within the part of the construct (ORF) encoding the fluorophore-pVIII fusion protein, for example within (internal to) or at (or near) the N-terminus, or at (or near) the C-terminus of the fluorophore-pVIII fusion protein.

In the vectors of the present invention, a preferred position for the sequence encoding the protein tag is at or near the N-terminus of the fluorophore in the fluorophore-pVIII fusion. For example, the sequence encoding the protein tag can be located between the signal peptide and the fluorophore.

In preferred embodiments of the invention the protein tag is a FLAG tag (or a derivative thereof), or another negatively charged tag. Without wishing to be bound by theory, it is believed that having a negatively charged tag, preferably located at or near the N-terminus of the fluorophore, for example between the signal peptide and the fluorophore, can result in improved stability and hence folding of the fluorophore-pVIII fusion protein, which is a phenomenon observed with other β-structures (Schaefer, 2012, J. Mol. Biol., 417:309-335 and Dudgeon et al., 2012, PNAS, 109: 10879-10884).

An exemplary structure for a construct of the invention with a fluorophore-pVIII fusion protein is shown in FIG. 1. As described elsewhere herein, the FLAG tag as shown in FIG. 1 (or other tag) is preferred but optional.

In preferred vectors of the invention a sequence encoding a spacer or linker is included between the sequence encoding the fluorophore and the sequence encoding the pVIII phage coat protein. The sequence can aid the folding of the connected proteins, in particular the N-terminal protein (here generally the fluorophore), and the spacer or linker length can be adjusted as appropriate to enable the best or satisfactory functional folding of both components. Appropriate lengths could readily be determined by a person skilled in the art. However exemplary lengths would be between five and 15 amino acids (Weiss et al., 2000, Protein Sci., 9:647-654), e.g. 6 to 10 amino acids. A particular linker used in the present invention is 8 amino acids long. The sequence of the linker is usually less relevant than the length. However the linker used in the exemplified vectors has the sequence GGGSGGGS (SEQ ID NO: 6, encoded for example by SEQ ID NO:5). This linker is thus preferred for some embodiments of the invention, but it will be appreciated that linkers (spacers) with other sequences and lengths can also be used.

Preferred vectors (or nucleic acid molecules) of the invention encode the sequence comprising SEQ ID NO:A or 16 (which comprises mNeonGreen, a linker and the N-terminal 30 amino acids of pVIII) or a sequence with at least 70% identity thereto (other exemplary values for percent identity are described elsewhere herein).

Other preferred vectors (or nucleic acid molecules) of the invention encode the sequence comprising SEQ ID NO:C or 18 (which comprises mNeonGreen, a linker and full length pVIII) or a sequence with at least 70% identity thereto (other exemplary values for percent identity are described elsewhere herein).

Other preferred vectors (or nucleic acid molecules) of the invention encode the sequence comprising SEQ ID NO:E or 20 (which comprises Tor AB7, mNeonGreen, a linker and full length pVIII) or a sequence with at least 70% identity thereto (other exemplary values for percent identity are described elsewhere herein).

Other preferred vectors (or nucleic acid molecules) of the invention encode the sequence comprising SEQ ID NO:G or 22 (which comprises Tor AB7, FLAG tag, mNeonGreen, a linker and full length pVIII) or a sequence with at least 70% identity thereto (other exemplary values for percent identity are described elsewhere herein).

Vectors (or nucleic acid molecules) encoding sequences comprising SEQ ID NO:K or 26 (which comprises Tor AB7, mNG, a linker, and the N-terminal 30 amino acids of pVIII) or SEQ ID NO:M or 28 (which comprises Tor AB7, FLAG tag, mNG, a linker, and the N-terminal 30 amino acids of pVIII), or a sequence with at least 70% identity thereto (other exemplary values for percent identity are described elsewhere herein) are also provided.

Any one of these vector sequences (e.g. sequences encoding SEQ ID NO: A or 16, C or 18, E or 20, G or 22, K or 26 or M or 28, or variants thereof) are examples of sequences which can be used in a parent vector and subjected to further variation or modification as outlined below.

A further exemplary vector sequence for use in the invention is shown in FIG. 9 (SEQ ID NO: 54 and 55).

Preferred pVIII variants, for example in the SEQ ID NOs: C or 18, E or 20, G or 22, 54 or 55, have a valine to isoleucine mutation at, or corresponding to, position 33 of SEQ ID NO:8 (i.e. have an isoleucine residue at, or corresponding to, position 33 of SEQ ID NO:8), or have an ATA isoleucine codon at, or corresponding to, residues 97-99 of SEQ ID NO:7, as described elsewhere herein. A particularly preferred pVIII variant is the pVIII sequence as found in the F03 clone as described elsewhere herein.

The phage display vectors of the invention as described above may also be used to produce further modified or variant vectors that can be used to produce fluorescent phage particles. Such modified (or variant or derivative or mutant) vectors also form part of the invention. Such modifications (or mutations) involve for example the addition, deletion, substitution or insertion of one or more nucleotides in the nucleic acid sequence of a parent vector to form a new vector, wherein said parent vector is one of the vectors of the invention as defined above, and testing the resulting new vector to identify vectors that can be used to produce fluorescent phage particles with improved properties. Such methods can be used to form multiple new vectors (conveniently a library of new vectors) that can all be tested for their ability to produce fluorescent phage particles, preferably improved fluorescent phage particles.

Said modifications, e.g. in the form of addition, deletion, substitution or insertion of one or more nucleotides (and hence encoded amino acids) can take place in any of the functional domains of the vector, namely in one or more (or all) of the signal peptide (preferably Tor A, more preferably Tor AB7), fluorophore (preferably mNeonGreen), linker between the fluorophore and pVIII, pVIII, or the tag (preferably FLAG tag) encoding parts of the vector. Preferably the modifications are located in one or more (or all) of the fluorophore (preferably mNeonGreen), the linker between the fluorophore and pVIII, or the pVIII encoding region. Where the modifications are located in the pVIII encoding region, in some embodiments the mutations are located in the N-terminal half of pVIII, for example within the first 90 nucleotides (or the first 30, e.g. the first 25-28 or 25-30 amino acids of pVIII).

Such modifications or mutations to a parent vector can be carried out in any appropriate manner using techniques well known and documented in the art, for example by carrying out methods of random or directed mutagenesis. Preferably the mutations made are substitutions and these can conveniently and preferably be made using random mutagenesis, in particular when it is desired to generate and screen multiple (e.g. a library of) mutants to select those which show improved properties. Random mutagenesis can be carried out in any appropriate way, e.g., by error-prone PCR or using mutator *E. coli* strains. A preferred and convenient technique is described in the Examples and involves the incorporation of dNTP analogues by PCR to introduce random mutations into the vector (e.g. phagemid) DNA. Commercial kits are available to carry out such random mutagenesis. In embodiments described elsewhere herein, where single, or only a few (for example up to 5), mutations are made, for example the valine to isoleucine (V to I) mutation in the pVIII protein (or corresponding mutation in the encoding nucleotide sequence) as described herein, then directed mutagenesis or other types of mutagenesis where specific residues can be targeted and modified are appropriate.

The new vectors produced by these methods, when transformed into an appropriate host cell, will preferably produce fluorescent phage particles which have improved functional properties, preferably improved fluorescent properties.

The present invention thus further provides variant or mutated vectors which are capable of producing phage particles which exhibit an improvement in the fluorescence intensity (improved brightness) compared to the original, starting, wild-type or parental phage particle (i.e. the phage particle produced by the non-mutated or wild-type parent vector). Such improvements can be provided by a) increasing the number of fluorophores on the surface of a bacteriophage particle, for example by increased incorporation or integration of fluorophore-pVIII fusion proteins into the phage surface/coat as an inherent property of phage particle assembly from the producing *E. coli* host by virtue of the fluorophore being fused to the viral capsid protein (in other words increasing the number or average number of fluorophore-pVIII molecules per particle), or b) increasing the brightness of the individual fluorochrome, e.g. increasing the intrinsic brightness (fluorescence intensity) of the fluorescent moiety in the fusion protein, or c) a combination of both a) and b), i.e. increasing the brightness and the number of the fluorophores. Another option, which could be used alone, or in combination with a) and/or b), would be to improve functional display of the fluorophore, e.g. by improving (e.g. more efficient) folding or increased solubility, as heterologous protein expression in *E. coli* frequently results in a fraction of translated, but non-functional protein products, e.g. insoluble protein products. Thus, improvements can also be provided by increasing the number of functional fluorophores on the phage surface.

In the case of a) it is not necessary for the brightness of the individual fluorophores to be increased. Thus, this result can be achieved with fluorophores showing the same fluorescent intensity as the starting fluorophore molecule, or, indeed, even a reduced fluorescent intensity of individual fluorophore molecules can be tolerated, as a greater number of fluorescent molecules will be displayed on the surface of each individual phage which could compensate for such a reduction.

Any appropriate assay can be used to screen for phage particles containing mutated vectors which have an increased number of fluorophores on the surface of the bacteriophage. For example, some kind of detectable tag (which is detectable on the surface of the phage) can conveniently be used to carry out such screening. Preferably these tags will be independent of the level of fluorescence displayed by the fluorescent moiety so that an indication of the number of fluorescent moieties on the surface of the phage can be assessed. Examples of detectable tags will be well known to a person skilled in the art. For example, a FLAG tag can be used. Detection can conveniently be carried out using an antibody to the tag in question. FACS, e.g. using a fluorescently labelled antibody, e.g. an antibody to the FLAG tag, is particularly preferred as it more readily allows individual particles to be screened by way of monitoring and selecting particles which have shifted in a positive direction on the relevant fluorescence axis. Alternatively to the use of a detectable tag, antibodies specifically recognizing the fluorophore, such as anti-mNeonGreen 32F6 (ChromoTek GmbH), or similar, could be used for FACS. Exemplary methods, for example FACS-based methods, or similar methodology capable to measure a fluorescent signal from the fluorophore in question (e.g. FLISA), are shown in the Examples.

In the case of b) it is not necessary for an increase in the number of fluorophores on the surface of an individual phage particle to be achieved. Thus, this result can be achieved with the same number of fluorophores on the surface of an individual phage particle, or, indeed, even a reduced number of individual fluorophore molecules can be tolerated, as increasing the brightness of the individual fluorochrome, e.g. increasing the intrinsic brightness (fluorescence intensity) of the fluorescent moiety could compensate for such a reduction.

Any appropriate assay can be used to screen for phage particles containing mutated vectors which have an increased brightness of the individual fluorochrome in the fusion protein expressed on the surface of the bacteriophage. For example, FACS or some other kind of fluorescence-based assay can be used to measure the level of fluorescence, e.g. measuring fluorescence levels of phage particles in solution, in combination with another method of quantification of the fluorophore, e.g. use of western blot, or the use of an antibody to the fluorophore, e.g. the anti-NeonGreen nanobody as used in the FACS sorting shown in the Examples. FACS is particularly preferred as it more readily allows individual particles to be screened by way of monitoring and selecting particles which have shifted in a positive direction on the relevant fluorescence axis. Exemplary methods, for example FACS-based methods or FLISA, are shown in the Examples.

Preferably such increases (and indeed other increases, improvements or positive effects as mentioned elsewhere herein) are measurable increases, etc., (as appropriate), more preferably they are significant increases, preferably statistically significant increases, for example with a probability value of ≤0.05, when compared to an appropriate control level or value (e.g. compared to the level of fluorescence obtained with a non-mutated or parent or wild-type vector). Preferred increases in fluorescence intensity might be increases of greater than or at least two-fold or three-fold, e.g. up to 5-fold, 10-fold or 20-fold, more than the parent vector. A convenient comparator or baseline level for a parent vector which can be used to assess such increases or improvements could be a vector comprising sequences encoding SEQ ID NO:E or 20 or SEQ ID NO:G or 22 or SEQ ID NO:C or 18 (or indeed SEQ ID NOs: A or 16, K or 26 or M or 28).

Mutated versions of a vector which can produce fluorescent phage expressing an mNeonGreen-pVIII fusion protein on the surface have been developed which display improved fluorescence properties. Some of these mutated versions show improved brightness of the mNeonGreen fluorescent moiety on an individual basis (as evidenced by a shift up the y-axis on the FACS profiles shown in Example 2). Others of these mutated versions show improved display, i.e. an increased number of fluorophores, on the surface of the bacteriophage (as evidenced by a shift to the right along the x-axis on the FACS profiles shown in Example 2, assessed by measurement of a FLAG tag with a labelled antibody). Others of these mutated versions show both improved brightness of the mNeonGreen fluorescent moiety on an individual basis and an increased number of fluorophores on the surface of the bacteriophage (as evidenced by the presence of clones in the top right quadrant of the FACS profiles shown in Example 2).

As described above, the mutated residues which result in the improved fluorescence of the phage particles can be located in any part of the vector but are preferably in either the mNeonGreen or the pVIII part of the fusion protein (more preferably in the pVIII part), or in the linker between the mNeonGreen and pVIII. Where the mutations are located in the pVIII region, in some embodiments the mutations are located in the N-terminal half of pVIII, for example within the first 90 nucleotides (or the first 30, e.g. the first 25-28 or 25-30 amino acids of pVIII).

As described above, in preferred embodiments of the invention, the encoded amino acid sequence for the mNeonGreen part of the vector is provided by SEQ ID NO:4 (and an exemplary nucleotide sequence is provided by SEQ ID NO:3). Thus, in embodiments where at least some of the mutated residues which result in the retained or improved fluorescence of the phage particles are located in the mNeonGreen part of the vector, such variant mNeonGreen components may comprise SEQ ID NO:3 or SEQ ID NO:4, or a sequence with at least 70% identity thereto at either the nucleotide or amino acid level (e.g. at least 75%, 80%, 85%, 87%, 88%, 90%, 91%, 92%, 93%, 94%, 95%, 96%, 97%, 98% or 99% identity). Put alternatively such variant components may comprise a mutation level of up to 30%, 25%, 20%, 15%, 13%, 12%, 10%, 9%, 8%, 7%, 6%, 5%, 4%, 3%, 2% or 1% in SEQ ID NO:3 or SEQ ID NO:4 at either the nucleotide or amino acid level, respectively, preferably at the amino acid level. Preferred variant mNeonGreen components may comprise a mutation level of up to 15%, preferably up to 13% or 10%, more preferably up to 5% or 4%.

Other preferred examples of mutated mNeonGreen sequences are sequences containing up to 30, e.g. up to 25, 20, 15, 12, or 10, e.g. 1, or up to 2, 3, 4, 5, 6, 7, 8, 9 or 10 altered amino acids in the mNeonGreen sequence, e.g. SEQ ID NO:4.

As described above, in preferred embodiments of the invention the encoded amino acid sequence for the pVIII part of the vector is provided by SEQ ID NO:8 (and an exemplary nucleotide sequence is provided by SEQ ID NO:7). Thus, in embodiments where at least some of the mutated residues which result in the retained or improved fluorescence of the phage particles are located in the pVIII part of the vector, such variant pVIII components may comprise SEQ ID NO:7 or SEQ ID NO:8, or a sequence with at least 70% identity thereto at either the nucleotide or amino acid level (e.g. at least 75%, 80%, 85%, 87%, 88%, 90%, 91%, 92%, 93%, 94%, 95%, 96%, 97%, 98% or 99% identity). Put alternatively such variant components may comprise a mutation level of up to 30%, 25%, 20%, 15%, 13%, 12%, 10%, 9%, 8%, 7%, 6%, 5%, 4%, 3%, 2% or 1% in SEQ ID NO:7 or SEQ ID NO:8 at either the nucleotide or amino acid level, respectively, preferably at the amino acid level. Preferred variant pVIII components may comprise a mutation level of up to 15%, preferably up to 13% or 10%, more preferably up to 5% or 4%.

Other preferred examples of mutated pVIII sequences are sequences containing up to 10, e.g. up to 9, 8, 7, 6, 5, 4, 3, 2 or 1 altered amino acids in the pVIII sequence, e.g. SEQ ID NO:8.

As described elsewhere herein, although other mutated residues may be present, preferred mutated vector sequences contain a valine to isoleucine substitution at residue (or position) 33 of SEQ ID NO:8, or a residue corresponding thereto (i.e. have an isoleucine residue at, or corresponding to, position 33 of SEQ ID NO:8). More preferably, the codon encoding the isoleucine is ATA. For example, a valine codon GTC can be substituted with the isoleucine codon ATA. Thus, in the above discussed embodiments where variant vectors may comprise SEQ ID NO:8, or a sequence with at least 70% identity to SEQ ID NO:8, or a mutation level of up to 15%, or a certain number, e.g. up to 35, altered amino acids in SEQ ID NO:8, in preferred embodiments this isoleucine residue or codon is present.

As also described above, in some embodiments of the invention the mutated residues are present in the N-terminal half of the pVIII protein, for example in the encoded amino acid sequence for the pVIII part of the vector as provided by SEQ ID NO:J or 25 which contains the first 30 amino acids of pVIII (with an exemplary nucleotide sequence as provided by SEQ ID NO:I or 24, the first 90 nucleotides of pVIII). Thus, in embodiments where at least some of the mutated residues which result in the retained or improved fluorescence of the phage particles are located in the pVIII part of the vector, such variant pVIII components may comprise SEQ ID NO:I or 24 or SEQ ID NO:J or 25, or a sequence with at least 70% identity thereto at either the nucleotide or amino acid level (e.g. at least 75%, 80%, 85%, 87%, 88%, 90%, 91%, 92%, 93%, 94%, 95%, 96%, 97%, 98% or 99% identity). Put alternatively such variant components may comprise a mutation level of up to 30%, 25%, 20%, 15%, 13%, 12%, 10%, 9%, 8%, 7%, 6%, 5%, 4%, 3%, 2% or 1% in SEQ ID NO:I or 24 or SEQ ID NO:J or 25 at either the nucleotide or amino acid level, respectively, preferably at the amino acid level. Preferred variant pVIII components may comprise a mutation level of up to 15%, preferably up to 13% or 10%, more preferably up to 5% or 4%.

Other preferred examples of mutated pVIII sequences are sequences containing up to 5, e.g. up to 4, 3, 2 or 1 altered amino acids in the pVIII sequence, e.g. SEQ ID NO:J or 25.

As described above, in preferred embodiments of the invention the encoded amino acid sequence for the linker part of the vector (here we are referring to the linker between the fluorophore and the pVIII components) is provided by SEQ ID NO:6 (and an exemplary nucleotide sequence is provided by SEQ ID NO:5). Thus, in embodiments where at least some of the mutated residues which result in the retained or improved fluorescence of the phage particles are located in this linker part of the vector, such variant linker components may comprise SEQ ID NO:5 or SEQ ID NO:6, or a sequence with at least 70% identity thereto at either the nucleotide or amino acid level (e.g. at least 75%, 80%, 85%, 87%, 88%, 90%, 91%, 92%, 93%, 94%, 95%, 96%, 97%, 98% or 99% identity). Put alternatively such variant components may comprise a mutation level of up to 30%, 25%, 20%, 15%, 13%, 12%, 10%, 9%, 8%, 7%, 6%, 5%, 4%, 3%, 2% or 1% in SEQ ID NO:5 or SEQ ID NO:6 at either the nucleotide or amino acid level, respectively, preferably at the amino acid level.

Preferred variant linker components may comprise a mutation level of up to 15%, preferably up to 13% or 10%, more preferably up to 5% or 4%.

Other preferred examples of mutated linker sequences are sequences containing 1, 2 or 3 altered amino acids in the linker sequence, e.g. SEQ ID NO:6. In other embodiments no mutations are present in the linker sequence, e.g. SEQ ID NO:6.

As described above, in some embodiments of the invention the encoded amino acid sequence for the TorAB7 part of the vector is provided by SEQ ID NO:2 (and an exemplary nucleotide sequence is provided by SEQ ID NO:1). Thus, in embodiments where at least some of the mutated residues which result in the retained or improved fluorescence of the phage particles are located in the TorAB7 part of the vector, such variant TorAB7 components may comprise SEQ ID NO:2 or SEQ ID NO:1, or a sequence with at least 70% identity thereto (e.g. at least 75%, 80%, 85%, 87%, 88%, 90%, 91%, 92%, 93%, 94%, 95%, 96%, 97%, 98% or 99% identity). Put alternatively such variant components may comprise a mutation level of up to 30%, 25%, 20%, 15%, 13%, 12%, 10%, 9%, 8%, 7%, 6%, 5%, 4%, 3%, 2% or 1% in SEQ ID NO:1 or SEQ ID NO:2 at either the nucleotide or amino acid level, respectively, preferably at the amino acid level. Preferred variant TorAB7 components may comprise a mutation level of up to 15%, preferably up to 13% or 10%, more preferably up to 5% or 4%.

Other preferred examples of mutated TorAB7 sequences are sequences containing up to 6, e.g. up to 5, 4, 3, 2, or 1 altered amino acids in the TorAB7 sequence, e.g. SEQ ID NO:2.

In other preferred embodiments of the invention the mutations may be found in one or more (or all) of the mNeonGreen, the linker between the mNeonGreen and pVIII, and the pVIII encoding region. In some preferred embodiments, the mutations can be found in the pVIII encoding region. Where the mutations are located in the pVIII region, in some embodiments the mutations are located in the N-terminal half of pVIII, for example within the first 90 nucleotides (or the first 30, e.g. the first 25-28 or 25-30 amino acids of pVIII). Thus, in embodiments where at least some of the mutated residues which result in the retained or improved fluorescence of the phage particles are located in these regions of the vector, such variant vectors may comprise SEQ ID NO:A or 16 or SEQ ID NO:C or 18 or a sequence with at least 70% identity to SEQ ID NO:A or 16 or C or 18 (e.g. at least 75%, 80%, 85%, 87%, 88%, 90%, 91%, 92%, 93%, 94%, 95%, 96%, 97%, 98% or 99% identity). Put alternatively such variant components may comprise a mutation level of up to 30%, 25%, 20%, 15%, 13%, 12%, 10%, 9%, 8%, 7%, 6%, 5%, 4%, 3%, 2% or 1% in SEQ ID NO:A or C. Preferred variant components may comprise a mutation level of up to 15%, preferably 13% or 10%, more preferably up to 5% or 4%.

Other preferred examples of mutated vector sequences are sequences containing up to 30, e.g. up to 25, 20, 15, 12, or 10, e.g. 1, or up to 2, 3, 4, 5, 6, 7, 8, 9 or 10 altered amino acids in the SEQ ID NO:A or 16 or C or 18.

As described elsewhere herein, although other mutated residues may be present, preferred mutated vector sequences contain a valine to isoleucine substitution at residue 276 of SEQ ID NO:C or 18, or a residue corresponding thereto (i.e. have an isoleucine residue at, or corresponding to, position 276 of SEQ ID NO:C or 18). More preferably, the codon encoding the isoleucine is ATA. For example, a valine codon GTC may be substituted with the isoleucine codon ATA. Thus, in the above discussed embodiments where variant vectors may comprise SEQ ID NO:C or 18, or a sequence with at least 70% identity to SEQ ID NO:C or 18, or a mutation level of up to 15%, or a certain number, e.g. up to 35, altered amino acids in SEQ ID NO:C or 18, in preferred embodiments this isoleucine residue or codon is present.

In other preferred embodiments of the invention the mutations may be found in one or more (or all) of the mNeonGreen, the linker between the mNeonGreen and pVIII, the pVIII encoding region, and the TorAB7 signal peptide. In some preferred embodiments, the mutations can be found in the pVIII encoding region.

Where the mutations are located in the pVIII region, in some embodiments the mutations are located in the N-terminal half of pVIII, for example within the first 90 nucleotides (or the first 30, e.g. the first 25-28 or 25-30 amino acids of pVIII). Thus, in embodiments where at least some of the mutated residues which result in the retained or improved fluorescence of the phage particles are located in these regions of the vector, such variant vectors may comprise SEQ ID NO:E or 20 or SEQ ID NO:K or 26 or a sequence with at least 70% identity to SEQ ID NO:E or 20 or SEQ ID NO:K or 26 at the amino acid level (e.g. at least 75%, 80%, 85%, 87%, 88%, 90%, 91%, 92%, 93%, 94%, 95%, 96%, 97%, 98% or 99% identity). Put alternatively such variant components may comprise a mutation level of up to 30%, 25%, 20%, 15%, 13%, 12%, 10%, 9%, 8%, 7%, 6%, 5%, 4%, 3%, 2% or 1% in SEQ ID NO:E or 20 or SEQ ID NO:K or 26. Preferred variant components may comprise a mutation level of up to 15%, preferably 13% or 10%, more preferably up to 5% or 4%.

Other preferred examples of mutated vector sequences are sequences containing up to 35, e.g. up to 30, 25, 20, 17, 15, 12, or 10, e.g. 1, or up to 2, 3, 4, 5, 6, 7, 8, 9 or 10 altered amino acids in the SEQ ID NO:E or 20 or K or 26.

As described elsewhere herein, although other mutated residues may be present, preferred mutated vector sequences contain a valine to isoleucine substitution at residue 317 of SEQ ID NO:E or 20, or a residue corresponding thereto (i.e. have an isoleucine residue at, or corresponding to, position 317 of SEQ ID NO:E or 20). More preferably, the codon encoding the isoleucine is ATA. For example, a valine codon GTC may be substituted with the isoleucine codon ATA. Thus, in the above discussed embodiments where variant vectors may comprise SEQ ID NO:E or 20, or a sequence with at least 70% identity to SEQ ID NO:E or 20, or a mutation level of up to 15%, or a certain number, e.g. up to 35, altered amino acids in SEQ ID NO:E or 20, in preferred embodiments this isoleucine residue or codon is present.

In other preferred embodiments of the invention the mutations may be found in one or more (or all) of the mNeonGreen, the linker between the mNeonGreen and pVIII, the pVIII encoding region, the TorAB7 signal peptide and the FLAG sequence.

Where the mutations are located in the pVIII region, in some embodiments the mutations are located in the N-terminal half of pVIII, for example within the first 90 nucleotides (or the first 30, e.g. the first 25-28 or 25-30 amino acids of pVIII). Thus, in embodiments where at least some of the mutated residues which result in the retained or improved fluorescence of the phage particles are located in these regions of the vector, such variant vectors may comprise SEQ ID NO:G or 22 or SEQ ID NO:M or 28 or a sequence with at least 70% identity to SEQ ID NO:G or 22 or SEQ ID NO:M or 28 (e.g. at least 75%, 80%, 85%, 87%, 88%, 90%, 91%, 92%, 93%, 94%, 95%, 96%, 97%, 98% or 99% identity). Put alternatively such variant components may comprise a mutation level of up to 30%, 25%, 20%, 15%, 13%, 12%, 10%, 9%, 8%, 7%, 6%, 5%, 4%, 3%, 2% or 1% in SEQ ID NO:G or 22 or SEQ ID NO:M or 28. Preferred variant components may comprise a mutation level of up to 15%, preferably 13% or 10%, more preferably up to 5% or 4%.

Other preferred examples of mutated vector sequences are sequences containing up to 35, e.g. up to 30, 25, 20, 17, 15, 12, or 10, e.g. 1, or up to 2, 3, 4, 5, 6, 7, 8, 9 or 10 altered amino acids in the SEQ ID NO:G or 22 or M or 28.

As described elsewhere herein, although other mutated residues may be present, preferred mutated vector sequences contain a valine to isoleucine substitution at residue 325 of SEQ ID NO:G or 22, or a residue corresponding thereto (i.e. have an isoleucine residue at, or corresponding to, position 325 of SEQ ID NO:G or 22). More preferably, the codon encoding the isoleucine is ATA. For example, a valine codon GTC can be substituted with the isoleucine codon ATA. Thus, in the above discussed embodiments where variant vectors may comprise SEQ ID NO:G or 22, or a sequence with at least 70% identity to SEQ ID NO:G or 22, or a mutation level of up to 15%, or a certain number, e.g. up to 35, altered amino acids in SEQ ID NO:G or 22, in preferred embodiments this isoleucine residue or codon is present.

In such embodiments where the vectors contain a FLAG tag, it is preferred that the FLAG tag remains unmodified or non-mutated, e.g. retains the sequence of SEQ ID NO:10 (DYKDDDDK).

In particularly preferred embodiments, the vectors of the invention contain mutations such that the mutated or variant sequences display reduced or significantly reduced or weaker or decreased translation efficiency or speed. Thus, vector constructs where the translation efficiency of the fluorophore-pVIII fusion protein is low, weak, reduced, decreased, or non-optimal are generally preferred. Preferred modifications/variant molecules are those in which translation efficiency, for example and in particular of the fluorophore-pVIII fusion protein, is reduced or significantly reduced (or decreased), for example compared to the original parent (non-mutated or unmodified) sequence, specific examples of which are described elsewhere herein. By way of example, this can be achieved by having a mutated pVIII component such that the translation efficiency of the pVIII protein (and hence the whole ORF containing the fluorophore-pVIII fusion protein) is reduced or significantly reduced. However, equally it is envisaged that mutations in other parts of the fluorophore-pVIII fusion protein, e.g. in the fluorophore (e.g. the mNeongreen fluorophore) or in the linker sequence or in the signal peptide can result in reduced translation efficiency.

Variants with reduced translation efficiency could be screened or tested by appropriate methods devised or known by a person skilled in the art. For example, a time chase assay could be carried out on normalized host cell numbers and the protein production quantified by a means independent of protein functionality, e.g. by means of a Western Blot, to assess whether the absolute amount of protein is lower in the system being tested for reduced translation efficiency compared to a relevant control (e.g. a non-variant or wild type fusion protein).

Preferably such decreases (and indeed other decreases, reductions or negative effects as mentioned elsewhere herein) are measurable decreases, etc., (as appropriate), more preferably they are significant decreases, preferably statistically significant decreases, for example with a probability value of ≤0.05, when compared to an appropriate control level or value (e.g. compared to the level of translation, e.g. translation efficiency or speed, obtained with a non-mutated or parent or wild-type vector, or other relevant control).

Whilst not wishing to be bound by theory, it is believed that this reduced translation efficiency or speed, and for example the more gradual or slower accumulation of fusion protein in the host cell, eventually results in more copies of the fluorophore-pVIII fusion protein being incorporated in the coat of the phage when compared to a vector construct (e.g. a parent construct, specific examples of which are described elsewhere herein) where normal or high translation efficiency is observed. Alternatively, the number of functional fluorophore fusions in the coat of the phage increases without necessarily changing the absolute number of units incorporated. As one of the aims of the invention is to increase the fluorescence of a phage particle by increasing the number of fluorophore-pVIII fusion proteins incorporated into the coat (on the surface) of the phage or by increasing the number of functional fusion proteins on the surface of the phage, it is somewhat surprising that in some embodiments a reduced translation efficiency, in particular of the fluorophore-pVIII fusion protein, produces better results, e.g. in terms of better functional display of the fluorophore pVIII fusion protein, and/or increased display (e.g more copies per particle) of the fluorophore pVIII fusion protein, which can then result in an increased fluorescence of phage particles.

One example of a mutation which results in improved fluorescence of phage particles is the modification of a V to an I at residue 33 of the pVIII protein shown in SEQ ID NO:8. This mutation is found in the clone F03 as described in the Examples which is shown to have improved fluorescence as compared to the parent sequence, or in other words compared to a sequence which does not have the V to I mutation at this position. Interestingly, when the nucleic acid sequence is examined, the position 33 valine encoding codon, GTC, in the parent/wild type/unmodified pVIII, has been changed to the isoleucine encoding codon, ATA. This is an extremely rare codon in *E. coli* and thus is believed to contribute to significantly reduced translation efficiency of the fluorophore-pVIII fusion protein in the F03 clone. Thus, other suitable mutations would be those which result in the incorporation of rare codons (codons which are rare in *E. coli*) such as ATA in the nucleic acid sequence (T would of course be U in a corresponding RNA sequence). Appropriate rare codons would be well-known to a person skilled in the art, however some examples might be rare Arg codons such as AGG, CGA, AGA or CGG, or CTA (Leu), CCC (Pro), or TCG (Ser). Another example might be to exchange the normal ATG start/initiation codon for a rarer codon, e.g. the rarer GTG codon.

As can be seen from the experimental Examples, the presence of the V to I mutation at this position, for example by way of the presence of the change of the GTC valine codon to the ATA isoleucine codon, results in significantly improved fluorescence, for example in the order of 2 fold higher (or 100% higher) than the fluorescence observed with the wild type/parent/unmodified pVIII sequence. The fluorescence observed was already bright. Indeed it is believed that the fluorescence conferred by expressing the parent vector exhibited the brightest fluorescence for a phage particle known in the art. Thus, to double this fluorescence, is a significantly advantageous improvement.

Thus, as described elsewhere herein, although other mutated residues may be present, preferred mutated vector sequences have a pVIII sequence which contains a valine to isoleucine substitution at residue 33 of SEQ ID NO:8, or a residue corresponding thereto (i.e. have an isoleucine residue at, or corresponding to, position 33 of SEQ ID NO:8). More preferably, the codon encoding the isoleucine is ATA. For example, a valine codon GTC may be substituted with the isoleucine codon ATA. Thus, in the embodiments as described elsewhere herein where variant vectors may comprise SEQ ID NO:8, or a variant of SEQ ID NO:8, for example a sequence with at least 70% identity to SEQ ID NO:8, or a mutation level of up to 15%, or a certain number, e.g. up to 35, altered amino acids in SEQ ID NO:8, in preferred embodiments this isoleucine residue or codon is present. Thus, in preferred vector constructs the pVIII phage coat protein or variant sequence contained (or encoded) in the vectors has a valine to isoleucine mutation (an isoleucine residue) at position 33 of SEQ ID NO:8 or a corresponding position. Preferably the nucleic acid sequence encoding said isoleucine residue comprises the codon ATA.

Equally, although other mutated residues may be present, at the nucleotide level preferred mutated vector sequences encoding the pVIII protein contain a GTC to ATA substitution at residues 97-99 of SEQ ID NO:7, or residues corresponding thereto. Thus, in the embodiments as described elsewhere herein where variant vectors may comprise SEQ ID NO:7, or a variant of SEQ ID NO:7, for example a sequence with at least 70% identity to SEQ ID NO:7, then, in preferred embodiments this ATA codon encoding isoleucine is present.

Thus, preferred vector constructs comprise a pVIII phage coat protein comprising SEQ ID NO:61, or a sequence with at least 70% identity to SEQ ID NO: 61. Alternatively, the pVIII phage coat protein is encoded by a sequence which comprises SEQ ID NO:60, or a sequence with at least 70% identity to SEQ ID NO:60.

For example, in some embodiments the encoded pVIII protein comprises or consists of an amino acid sequence with a sequence identity of at least 70%, 75% or 80% to that of SEQ ID NO: 61, such as at least 80%, 81%, 82%, 83%, 84%, 85%, 86%, 87%, 88%, 89%, 90%, 91%, 92%, 93%, 94%, 95%, 96%, 97%, 98%, or 99% identity.

As indicated above, these variant pVIII sequences should retain or have the functional ability to display a fluorophore as a pVIII fusion protein. Functional truncations or fragments of SEQ ID NO:61 (or these homologous sequences) or other pVIII sequences, could also be used providing the ability to display a fluorophore as a pVIII fusion protein was retained.

Equally the nucleic acid molecule encoding the pVIII protein comprises or consists of a nucleotide sequence with a sequence identity of at least 70%, 75% or 80% to that of SEQ ID NO: 60, such as at least 80%, 81%, 82%, 83%, 84%, 85%, 86%, 87%, 88%, 89%, 90%, 91%, 92%, 93%, 94%, 95%, 96%, 97%, 98%, or 99% identity. These variant pVIII nucleotide sequences should retain or have the functional ability to encode a fluorophore as a pVIII fusion protein which could be displayed on a phage particle. Functional truncations or fragments of SEQ ID NO:60 (or these homologous sequences) or other pVIII sequences, could also be used providing the ability to encode a fluorophore as a pVIII fusion protein which could be displayed on a phage particle was retained.

The F03 clone as shown in the Examples, comprises a TorAB7 sequence of SEQ ID NO:2, a FLAG tag of SEQ ID NO:10, an mNeonGreen fluorophore of SEQ ID NO:4, a linker sequence of SEQ ID NO:6 and a pVIII phage coat protein of SEQ ID NO:61 (encoded by SEQ ID NO:60). Thus, vectors comprising or encoding one or more, or all, of these sequences are preferred, although the FLAG tag is optional. Vectors comprising sequences encoding an mNeonGreen fluorophore of SEQ ID NO:4, a linker sequence of SEQ ID NO:6 and a pVIII phage coat protein of SEQ ID NO:61 (encoded by SEQ ID NO:60) are preferred, as are vectors comprising the sequences shown in FIG. 9 but wherein the pVIII phage coat protein has or comprises the amino acid sequence shown in SEQ ID NO: 61 (encoded by SEQ ID NO:60). Variants with at least 70% identity to one or more, or all, of these sequences are also contemplated, as described elsewhere herein. However, in such variant sequences, it is preferred that an isoleucine residue is present at residue 33 (or corresponding residues) of SEQ ID NO:61, or its variant sequence. It is also preferred that this isoleucine residue is encoded by the codon ATA (as is found in SEQ ID NO:60).

In some other embodiments the use of a variant exhibiting reduced translation efficiency of the fluorophore-pVIII fusion protein by way of the mutations in the pVIII (or other) components of the fluorophore-pVIII fusion protein (or encoding nucleic acid) as discussed above, in particular the V to I variants/mutants, can be combined with other features that result in reduced translation efficiency of the fluorophore-pVIII fusion protein, such as the use of a weak SD (or weak RBS) sequence in the vector construct upstream of the sequence encoding the ORF comprising the Tat signal peptide and the fluorophore-pVIII fusion protein as described elsewhere herein.

Preferred vectors of the invention can encode a second phage coat protein fusion which comprises a protein of interest (POI) or targeting unit fused to a phage coat protein other than pVIII. Such second phage coat protein fusions are preferably provided on the same vector as the fluorophore-pVIII fusion protein. However, the second coat protein fusion can be provided on a separate vector. Exemplary non-pVIII phage coat proteins would be well-known to a person skilled in the art, for example a fusion to pIII, pVI, pVII or pIX can be used. Such embodiments allow the display of a POI, e.g. a targeting protein, and a fluorophore on two different coat proteins of a phage particle simultaneously. Preferred second fusions would be of a protein of interest (POI) or targeting unit to pIX.

The vectors of the invention can thus further comprise a sequence (a nucleic acid sequence) encoding a POI fused (genetically fused) to a sequence encoding a non-pVIII phage coat protein. The POI and the non-pVIII phage coat protein can be in any appropriate order or spacing in the vector providing that, once expressed and packaged into phage particles, a functional fusion protein between the POI and the non-pVIII coat protein is formed wherein the non-pVIII coat protein component of the fusion protein forms part of the phage coat and the POI is functionally expressed or displayed on the surface of the phage particle. The POI part of the fusion protein is thus positioned in frame with the non-pVIII coat protein part of the fusion protein. In the vectors of the invention the POI component of the second fusion protein can be positioned N-terminally (or at or near the N-terminus) or C-terminally (or at or near the C-terminus) to the non-pVIII phage coat protein component of the second fusion protein. This will generally be determined based on the type of non-pVIII phage coat protein used and will be readily apparent to a person skilled in the art.

In embodiments where fusion of a POI to a second phage coat protein is used, it is preferred that each of the coat protein fusions (i.e. the pVIII and the non-pVIII fusion) is expressed as a separate open reading frame. Thus, in such embodiments, the vectors may contain two separate ribosomal binding sites (RBS) or SD or TIR regions, one directing translation of the fluorophore-pVIII fusion protein and the other directing translation of the POI-second coat protein fusion protein. Any appropriate RBS, etc., can be used to direct translation of the POI-second coat protein fusion protein (e.g strong, weak or consensus sequences as described elsewhere herein). The RBS sequences for the two coat protein fusions can thus be the same or different and examples are described elsewhere herein.

An exemplary structure for such a construct with two fusion proteins is shown in FIG. 2.

In such vectors, the sequences encoding the two fusion proteins can be in any order, although in some embodiments the POI fusion protein is positioned N-terminally to the fluorophore-pVIII fusion protein.

As described elsewhere herein a signal sequence or signal peptide can be included in the ORF for the non-pVIII fusion protein. This will largely depend on the type of non-pVIII fusion protein being used. A pIII fusion protein will generally require a signal peptide, whereas a signal peptide is optional for pVII and pIX fusion proteins (i.e. present or absent), whereas signal sequences will generally not be used for pVI. For example, pVI is generally used as a C-terminal fusion. In some embodiments of the invention where a second signal peptide is used, a signal peptide other than Tat will be used.

In such embodiments it is also preferred that both coat protein fusions are expressed under the control of the same promoter sequence, although in other embodiments separate or different (e.g. 2) promoter sequences could be used. Exemplary promoter sequences would be well known to a person skilled in the art and any of these could be used. An exemplary promoter sequence might be a lac promoter which can for example be induced with IPTG. Other promoters may include tac, arabB, or psp.

Importantly, the results shown herein demonstrate that the expression of the pVIII-fluorophore fusion protein on the phage surface does not interfere with the binding capability of a POI, and in particular a targeting protein (e.g. the antigen binding capability of an antibody), displayed on a different coat protein on the same phage particle, e.g. pIX. Thus, the pVIII-fluorophore fusion protein can be used in conjunction with expression of a protein of interest on any other phage coat protein.

Any protein of interest (POI) can be encoded in the vectors of the invention providing that it is suitable for display on a phage. Preferred examples would be targeting molecules/targeting units or binding partners which can bind to (target) other entities. Some preferred examples of POIs would be antibodies or fragments thereof (e.g. Fab, scFv, nanobodies), MHC molecules (class I or class II), T cell receptors, or non-Ig derived binding proteins such as DARPins, Ankyrin family, fibronectin family, knottins, anticalins, etc., (Hosse et al., 2006, Protein Sci 15:14-27) and peptides.

The vectors of the present invention can be used for classical phage display in order to select binding partners (e.g. antibodies) for a particular target entity, e.g. target protein. In such applications a library of POIs can be expressed on phage particles as part of the non-pVIII fusion protein (the second coat protein fusion) and selected for binding to a target entity by standard and well-known techniques. The detectable phage surface fluorescence provided by the fluorescent-pVIII fusion protein can be used for screening and detection.

Thus, the POI is typically exogenous or heterologous, as indeed is the fluorophore. When referring to an exogenous or heterologous protein, what is meant is a protein or peptide not originally part of the relevant phage coat protein, e.g. the pIII, pVI, pVII, pIX or pVIII protein, etc., which is fused (with or without any linker amino acids) to a phage coat protein (or fragment thereof), e.g. fused to the N-terminal end of the phage coat protein.

Other optional features which may be present in the vectors (or nucleic acid molecules) of the invention would be well-known to a person skilled in the art. For example, the vectors, e.g. the phage vectors or phagemid vectors (which can collectively be termed phage display vectors or constructs) may optionally additionally contain other appropriate components, for example origins of replication, inducible or non-inducible promoters/operators for initiating transcription, enhancers, termination sequences, antibiotic resistance genes and markers, sequences encoding chaperone proteins (e.g. periplasmic chaperone proteins such as FkpA), signal sequences, linkers, protease sites, general tags or reporter molecules, restriction sites to enable cloning and other manipulations, primer binding sites to enable amplification of the constructs by e.g. PCR, or other desirable sequence elements, for example, DNA sequences to allow the discrimination between different libraries by e.g. PCR. Appropriate sources and positioning of such additional components within the phage display constructs so that they perform their desired function would be well within the normal practice of a skilled person in the art.

Appropriate bacterial hosts for phage display which can be used to express the vectors and nucleic acid sequences of the invention and to package and produce fluorescent phage particles would be well-known to a person skilled in the art and could be selected accordingly. Preferred bacterial host cells are Gram negative bacteria such as strains of E. coli. Exemplary E. coli strains would include XL-1 blue, TG1, ER2738, AVB100FmkII', MC1061, SS320 and TOP10F'. In some embodiments XL-1 blue strains are preferred.

Preferred bacterial hosts, e.g. E. coli hosts, for use in the present invention are hosts which have been engineered to overexpress the Tat transporter protein, or components of the Tat transporter protein, for example overexpression of the proteins Tat A, Tat B and Tat C. Methods for such overexpression would be well known to a person skilled in the art, for example by expressing components of the Tat transporter protein, e.g. at least the proteins Tat A, Tat B and Tat C on expression vectors. Sequences and sources of these components, e.g. the proteins Tat A, Tat B and Tat C are readily available in the art, e.g. from standard databases. An exemplary method is shown in the attached Examples. These host cells can then be transfected or otherwise provided with the vectors of the invention and used to produce fluorescent phage particles.

As shown in the experimental Examples, the use of such hosts can enable improved fluorescence (increased fluorescence intensity) of bacterial cells expressing the phage particles, in addition to improved fluorescence (increased fluorescence intensity) of the phage particles produced in and secreted by the host cells, e.g. as compared to the fluorescence observed when a non-Tat transporter overexpressing bacterial host cell is used. This improved fluorescence can be significant, for example observed and preferred increases in fluorescence intensity might be increases of greater than or at least two-fold or three-fold, e.g. up to 5-fold, 10-fold, 20-fold or 30 fold more than the fluorescence observed when a non-Tat transporter overexpressing host cell is used.

Such bacterial host cells, e.g. E. coli, e.g. XL-1 blue or others as described herein, engineered to heterologously express or overexpress the Tat transporter protein, e.g. to heterologously express or overexpress at least the proteins Tat A, Tat B and Tat C, form a yet further aspect of the invention.

As described elsewhere herein the vectors of the invention are used for phage display and can therefore be phagemid vectors or phage vectors.

Phage display is a technique that is well known and described in the art. In this regard, in 1985, G. P. Smith established a method to display polypeptides on the surface of filamentous phage, a virus that infects E. coli cells (Smith, G. P., 1985, Science 228, 1315-1317). Since then, so called phage display has evolved into a powerful technology for protein engineering and selection of peptides and proteins binding a specific target (Løset and Sandlie, 2012, Methods 58, 40-46). The filamentous phage M13 is built from five different structural proteins. Protein VIII (pVIII) is the major coat protein, and the particle is capped at one end by 3-5 copies of pIII and pVI, and at the other end by 3-5 copies of pVII and pIX. The particle infects F pilus+ E. coli by way of pIII, and its ssDNA is injected into the bacterial cell. Here, phage DNA is replicated and transcribed, and new phage particles are assembled before nonlytic secretion into the growth medium.

In phage display, a gene encoding a protein of interest (POI) is normally placed between a gene encoding a coat protein (most often pIII) and its N-terminal signal sequence, to produce a POI-coat protein fusion, although in some embodiments of the present invention signal sequences are not always present. The term "phage library" refers to a collection of unique phages that differ in the amino acid sequence of the POI, and is prepared by standard molecular cloning techniques. A library may well contain >$10^{10}$ members, and can be used for selection of specific binders.

Another aspect of the present invention thus provides a library of fluorescent phages, e.g. fluorescent filamentous phages, produced by and therefore comprising the vectors (or nucleic acid molecules) of the invention as described herein. Said fluorescent phages comprise fluorophore-pVIII fusion proteins. Optionally said filamentous phages also display a POI or a library of POIs as fusions to pIII, pVI, pVII or pIX. As with other phage display libraries, each individual phage particle expresses/displays the same POI, but the presence of multiple particles allows the display of multiple (or a library or a plurality of) different POIs.

For aspects of the invention involving phage display, a general purpose phage display textbook such as "Phage Display in Biotechnology and Drug Discovery" by Sachdev S. Sidhu, 1995, or "Phage Display: A Laboratory Manual" by Barbas et al., 1994 can be referred to for relevant techniques and definitions.

Fluorophore- and POI-coat protein fusions can be encoded either in a complete phage genome by insertion of the sequences encoding the fluorophore or the POI into the sequences encoding the relevant coat protein in the phage genome (phage vector display), or on a phagemid (phagemid display). A phagemid is a high copy number plasmid that can encode the fluorophore-pVIII and optionally the POI-non-pVIII coat fusion protein, and superinfection with a helper phage that provides the genetic material required for phage production, is required. Thus, in phagemid display, there are generally two sources of the coat protein that is utilized for fluorophore and optionally POI display; the helper phage encoded wild type protein, and the phagemid encoded fluorophore-pVIII and optionally POI-coat protein fusion. The new virions will then have a mixture of fluorophore-pVIII/POI-non-pVIII coat protein fusions and wild type coat proteins. Similarly, if a phage genome system is used, then wild-type phage proteins also generally need to be present, although in some embodiments of the present invention, no wild-type of the POI-non-pVIII coat protein is present.

However, in the present invention, it is possible for the phage particles to be engineered to have one or multiple copies of the POI displayed on the non-pVIII coat protein. This can be controlled by the helper phage which is used and in preferred embodiments of the invention phage particles with multiple copies of the POI displayed on the non-pVIII coat protein are used. This can be achieved in any appropriate manner. However, in particular, to increase the display level and result in multiple copies of the POI on the surface of the phage (which can also increase the avidity of binding), it is possible to use a modified type of helper phage termed DeltaPhage that allows high valence display on pIX. Such modified helper phages contrast the use of normal helper phages such as M13K07, VCSM13, R408 or similar that only allows for low valence displays.

The helper phage called DeltaPhage was developed by Nicolay Rustad Nilssen (Nilssen et al., 2012, Nucleic acids research, 40, e120; WO 2011/036555). In this helper phage, at least one (e.g. two) amber mutations were inserted close to the pIX start codon, thereby conditionally inactivating the helper phage encoded pIX. If this helper phage is then superinfected into a host cell (e.g. *E. coli*) transformed with a phagemid encoding a POI-pIX fusion, then in a host cell which suppresses the amber mutation (e.g. a supE+ strain) intermediate valence display of the POI-pIX is seen, whereas in a host cell which does not suppress the amber mutation (e.g. a supE− strain) high valence display of the POI-pIX is seen. This is because, in supE+ host cell strains (e.g. supE+ *E. coli*), wild type pIX from the helper phage is translated to give intermediate valence display as the wild-type pIX competes with the POI-pIX for display and a mixture of both are displayed. However, production of wild type pIX on the helper phage is blocked in supE− strains, and only the phagemid encoded POI-pIX will be present, resulting in high valence display.

Thus, in preferred embodiments of the invention, the vector construct is a phagemid vector which comprises a POI-pIX fusion protein in addition to the fluorophore-pVIII fusion protein and such a vector construct is used in combination with a helper phage which has a conditional mutation such that expression of the wild-type pIX phage protein can be controlled, which in turn can enable control of the number of POI-pIX fusion proteins on the surface of the phage. In embodiments where the conditional mutation is not suppressed then the wild-type pIX will not be expressed and only the POI-pIX will be expressed resulting in only POI-pIX fusion proteins on the surface and high valency display. In embodiments where the conditional mutation is suppressed, then the wild-type pIX protein will be expressed resulting in a mixture of wild-type pIX and POI-pIX fusion proteins on the surface.

Suitable conditional mutations would be well known to a person skilled in the art and helper phage vectors can readily be designed so that the pIX is under control of the conditional mutation. For example, in the helper phage called DeltaPhage, as described above, conditional mutations in the form of one or more suppressible stop codons (e.g. amber mutations) are used in conjunction with appropriate host cells to suppress or not suppress the conditional mutation.

The term "phagemid" is a term of the art and refers to a type of cloning vector developed as a hybrid of the filamentous phage Ff and plasmids to produce a vector that can propagate as a plasmid, and also be packaged as single stranded DNA in viral particles. Similarly to a plasmid, a phagemid can be used to clone DNA fragments and be introduced into a bacterial host by a range of techniques (transformation, electroporation). However, infection of a bacterial host containing a phagemid with a 'helper' phage, for example VCSM13 or M13K07, provides the necessary viral components to enable single stranded DNA replication and packaging of the phagemid DNA into phage particles.

As described elsewhere herein, another aspect of the present invention provides phage particles comprising the vector (or nucleic acid molecules) of the invention and expressing functional fluorophore-pVIII fusion proteins on the surface and optionally also expressing a second coat fusion protein comprising a POI. The phage particles may thus comprise a phage genome or a phagemid.

Phage, often called bacteriophage, is used herein in its art recognised form as meaning a virus infecting, replicating and which is secreted from bacteria. A filamentous bacteriophage, or filamentous phage, is a phage with a single stranded DNA genome (ssDNA genome) which is packaged with phage coat proteins. The secreted filamentous phage particle has phenotypically a filamentous structure.

The term phage or filamentous phage as used herein encompasses both phage genome derived virions and phagemid-derived virions.

The term "helper phage" is a term of the art and refers to a virus which helps a separate and unrelated defective virus, e.g. a phagemid, which in itself is not a phage genome or a functional virus, but merely a plasmid containing one or several elements derived from a phage genome, to reproduce by infecting the same host cell that is already occupied by the defective virus (e.g. phagemid) and providing the proteins which the defective virus (e.g. phagemid) is missing and needs to complete its life cycle and form virions, e.g. containing the phagemid.

Preferred helper phage for use in the present invention are described elsewhere herein and include M13K07 (Stratagene), Hyperphage (Progen Biotechnik GmbH), R408 (Agilent Technologies) and VCSM13 (Stratagene). In preferred embodiments, the helper phage may be a helper phage with a conditional (or suppressible) mutation as described e.g. the DeltaPhage constructs as described herein, or Phaberge, Ex-phage, VCSM13d3, or R408d3

Another aspect provided by the present invention is a phage display system comprising a vector (or nucleic acid molecule) of the invention. Preferred phage display systems comprise a vector (or nucleic acid molecule) of the invention, e.g. a phagemid vector of the invention and a helper phage, e.g. as defined herein. Other preferred phage display systems of the invention comprise a vector of the invention, e.g. a phagemid vector of the invention, and a bacterial host cell, e.g. an *E. coli* host cell, overexpressing the Tat transporter protein, e.g. overexpressing at least the proteins Tat A, Tat B and Tat C. Such host cells are also described elsewhere herein and can be included as a component in all the phage display systems, kits, methods and uses described here.

Another aspect described herein for use in the methods of the present invention is a kit comprising a vector (or nucleic acid molecule) of the invention or a kit comprising a phage display system as described above, for example composed of a phagemid of the invention and a helper phage, preferably a helper phage as described herein, e.g. a helper phage with a conditional (or suppressible) mutation as described herein, or a kit comprising a vector of the invention, e.g. a phagemid vector of the invention, and a bacterial host cell, e.g. an *E. coli* host cell, overexpressing the Tat transporter protein, e.g. overexpressing at least the proteins Tat A, Tat B and Tat C. The kit could also include be accompanied with necessary instructions for use.

Preferred vectors (or nucleic acid molecules) of the invention for inclusion in such kits could comprise the fluorophore-pVIII vector as described herein comprising a sequence encoding a Tat signal peptide and a sequence encoding a fluorophore-pVIII fusion protein. Optionally, the vectors (or nucleic acid molecules) could also comprise a sequence encoding a second phage coat protein (a non-pVIII phage protein) e.g. as described herein, and one or more cloning sites (e.g. a multiple cloning site) suitable for cloning in a POI which would then be fused to the second phage protein.

A preferred kit can thus comprise or consist of a collection of reagents for generating fluorescent phage particles comprising a fluorophore-pVIII fusion protein, optionally with a second fusion protein of a POI to a non-pVIII coat protein. As well as the vector of the invention, a kit could include one or more components selected from: other phagemids, helper phages, bacterial strains and instructions. Preferred options for such additional components are as described elsewhere herein.

A yet further aspect of the invention provides the use of a vector construct, a nucleic acid molecule, a phage display system or a kit of the invention to produce fluorescent phage particles, or use in phage display. Put alternatively, the present invention provides a method for producing fluorescent phage particles (or a method of phage display), said method comprising the use of a vector construct, a nucleic acid molecule, a phage display system or a kit of the invention.

The fluorescent phage particles of the invention as defined herein may also be used as molecular tools for in vitro applications and assays. The particles may be used in any assay in which a detectable fluorescent reagent is desired.

As preferred phage particles of the invention also display a POI which can be a specific binding partner or targeting unit, e.g. an antibody etc., as described elsewhere herein, these can function as members of specific binding pairs or targeting reagents, and such fluorescent phage particles can be used in any assay where the particular binding pair member or targeting unit is required. The fluorophore can then readily be used to detect the particles and hence detect the binding of the POI to its target. Importantly for such uses it has been shown herein that the display of the fluorophore-pVIII on the surface of the phage particles does not interfere with a targeting module displayed on another phage coat protein.

The fluorescent phage particles of the invention can also be used for any assay involving fluorescence detection, in particular fluorescence staining (e.g. in solution or on cells). Thus preferred assays for use of the particles are FACS analysis or immunofluorescence or FLISA assays (which have a detection system comparable to FACS analysis). The ability to use the particles in immunofluorescence or FLISA assays avoids the need for staining (or detection) antibodies, but only relies on the inherent fluorescence of the fluorophore-pVIII fusion for detection. The ability to use the particles in FACS analysis would provide a significant advantage of being able to carry out real-time selection (e.g. real-time phage display) to avoid the need for staining (or detection) antibodies, but only relying on the inherent fluorescence of the fluorophore-pVIII fusion for detection. Use for in vitro diagnosis is also contemplated.

Thus, yet further aspects of the invention provide a reagent that comprises fluorescent phage particles of the invention as defined herein and the use of such fluorescent phage particles as molecular tools, for example in in vitro assays.

Some of the sequences referred to herein are summarised in the Table below, along with relevant identifiers.

| SEQ ID NO: | Description | Sequence |
| --- | --- | --- |
| 1 (part 1 of vector) | Tor AB7 nt (114 residues) | ATGAACAATAACGATCTCTTTCAGACATCACGTCAGCGTTTTTTGGCAC AACTCGGCGGCTTAACCGTCGCCGGGATGCTGGGGCCGTCATTGTTAAC GCCGCGACGTGCGACT |
| 2 | aa (38 residues) | MNNNDLFQTSRQRFLAQLGGLTVAGMLGPSLLTPRRAT |
| 3 (part 2 of vector) | mNG nt (705 residues) | GTTTCTAAAGGTGAAGAAGACAACATGGCTTCTCTGCCGGCTACCCACG AACTGCACATCTTCGGTTCTATCAACGGTGTTGACTTCGACATG GTTGGTCAGGGTACCGGTAACCCGAACGACGGTTACGAAGAACTGAACC TGAAATCTACCAAAGGTGACCTGCAGTTCTCTCCGTGGATCTTAGTTCC GCACATCGGTTACGGTTTCCAC CAGTACCTGCCGTACCCGGACGGTATGTCTCCGTTCCAGGCTGCTATGG TTGACGGTTCT GGTTACCAGGTTCACCGTACCATGCAGTTCGAAGACGGTGCTTCTCTGA CCGTTAACTAC CGTTACACCTACGAAGGTTCTCACATCAAAGGTGAAGCTCAGGTTAAAG GTACCGGTTTC CCGGCTGACGGTCCGGTTATGACCAACTCTCTGACCGCTGCTGACTGGT GCCGTTCTAAA AAAACCTACCCGAACGACAAAACCATCATCTCTACCTTCAAATGGTCTT ACACCACCGGT AACGGTAAACGTTACCGTTCTACCGCTCGTACCACCTACACCTTCGCTA AACCGATGGCT |

| SEQ ID NO: | Description | Sequence |
|---|---|---|
| | | GCTAACTACCTGAAAAACCAGCCGATGTACGTTTTCCGTAAAACCGAAC<br>TGAAACACTCT<br>AAAACCGAACTGAACTTCAAAGAATGGCAGAAAGCTTTCACCGACGTTA<br>TGGGTATGGACGAACTGTACAAA |
| 4 | aa<br>(235 residues) | VSKGEEDNM ASLPATHELH IFGSINGVDF<br>DMVGQGTGNP NDGYEELNLK STKGDLQFSP<br>WILVPHIGYG FHQYLPYPDG MSPFQAAMVD<br>GSGYQVHRTM QFEDGASLTV NYRYTYEGSH<br>IKGEAQVKGT GFPADGPVMT NSLTAADWCR<br>SKKTYPNDKT IISTFKWSYT TGNGKRYRST<br>ARTTYTFAKP MAANYLKNQP<br>MYVFRKTELK HSKTELNFKE WQKAFTDVMG MDELYK |
| 5<br>(part 3 of vector) | Linker nt<br>(24 residues) | GGCGGTGGCAGCGGCGGTGGCAGC |
| 6 | aa<br>(8 residues) | GGGSGGGS |
| 7<br>(part 4 of vector) | pVIII (M13) nt<br>(150 residues) | GCTGAGGGTGACGATCCCGCAAAA<br>GCGGCCTTTAACTCCCTGCAAGCCTCAGCGACCGAATATATCGGTTATG<br>CGTGGGCGATG<br>GTTGTTGTCATTGTCGGCGCAACTATCGGTATCAAGCTGTTTAAGAAAT<br>TCACCTCGAAAGCAAGC |
| 8 | pVIII aa<br>(50 residues) | AEGDDP AKAAFNSLQASATEYIGYAW AMVVVIVGAT<br>IGIKLFKKFT SKAS |
| 9<br>(part 5 of vector) | FLAG nt<br>(24 residues) | GATTACAAGGATGACGATGACAAG |
| 10 | aa<br>(8 residues) | DYKDDDDK |
| A or 16 | Part 2, 3, N-t part of 4, (i.e. mNG, linker, 30 aa of pVIII) 273 residues total | VSKGEEDNM ASLPATHELH IFGSINGVDF<br>DMVGQGTGNP NDGYEELNLK STKGDLQFSP<br>WILVPHIGYG FHQYLPYPDG MSPFQAAMVD<br>GSGYQVHRTM QFEDGASLTV NYRYTYEGSH<br>IKGEAQVKGT GFPADGPVMT NSLTAADWCR<br>SKKTYPNDKT IISTFKWSYT TGNGKRYRST<br>ARTTYTFAKP MAANYLKNQP<br>MYVFRKTELK HSKTELNFKE WQKAFTDVMG<br>MDELYKGGGS GGGSAEGDDP AKAAFNSLQA<br>SATEYIGYAW AMVV |
| B or 17 | nt sequence of A | GTTTCTAAAGGTGAAGAAGACAACATGGCTTCTCTGCCGGCTACCCACG<br>AACTGCACATCTTCGGTTCTATCAACGGTGTTGACTTCGACATG<br>GTTGGTCAGGGTACCGGTAACCCGAACGACGGTTACGAAGAACTGAACC<br>TGAAATCTACCAAAGGTGACCTGCAGTTCTCTCCGTGGATCTTAGTTCC<br>GCACATCGGTTACGGTTTCCAC<br>CAGTACCTGCCGTACCCGGACGGTATGTCTCCGTTCCAGGCTGCTATGG<br>TTGACGGTTCT<br>GGTTACCAGGTTCACCGTACCATGCAGTTCGAAGACGGTGCTTCTCTGA<br>CCGTTAACTAC<br>CGTTACACCTACGAAGGTTCTCACATCAAAGGTGAAGCTCAGGTTAAAG<br>GTACCGGTTTC<br>CCGGCTGACGGTCCGGTTATGACCAACTCTCTGACCGCTGCTGACTGGT<br>GCCGTTCTAAA<br>AAAACCTACCCGAACGACAAAACCATCATCTCTACCTTCAAATGGTCTT<br>ACACCACCGGT<br>AACGGTAAACGTTACCGTTCTACCGCTCGTACCACCTACACCTTCGCTA<br>AACCGATGGCT<br>GCTAACTACCTGAAAAACCAGCCGATGTACGTTTTCCGTAAAACCGAAC<br>TGAAACACTCT<br>AAAACCGAACTGAACTTCAAAGAATGGCAGAAAGCTTTCACCGACGTTA<br>TGGGTATGGACGAACTGTACAAA<br>GGCGGTGGCAGCGGCGGTGGCAGC<br>GCTG |

| SEQ ID NO: | Description | Sequence |
|---|---|---|
| | | AGGGTGACGATCCCGCAAAAGCGGCCTTTAACTCCCTGCAA<br>GCCTCAGCGACCGAATATATCGGTTATGCGTGGGCGATGGT<br>TGTT |
| C or 18 | Part 2, 3, 4 (i.e. mNG, linker, full pVIII) 293 residues total | VSKGEEDNM ASLPATHELH IFGSINGVDF<br>DMVGQGTGNP NDGYEELNLK STKGDLQFSP<br>WILVPHIGYG FHQYLPYPDG MSPFQAAMVD<br>GSGYQVHRTM QFEDGASLTV NYRYTYEGSH<br>IKGEAQVKGT GFPADGPVMT NSLTAADWCR<br>SKKTYPNDKT IISTFKWSYT TGNGKRYRST<br>ARTTYTFAKP MAANYLKNQP<br>MYVFRKTELK HSKTELNFKE WQKAFTDVMG<br>MDELYKGGGS GGGSAEGDDP AKAAFNSLQA<br>SATEYIGYAW AMVVVIVGAT IGIKLFKKFT SKAS |
| D or 19 | nt sequence of C 879 residues total | GTTTCTAAAGGTGAAGAAGACAACATGGCTTCTCTGCCGGCTACCCACG<br>AACTGCACATCTTCGGTTCTATCAACGGTGTTGACTTCGACATG<br>GTTGGTCAGGGTACCGGTAACCCGAACGACGGTTACGAAGAACTGAACC<br>TGAAATCTACCAAAGGTGACCTGCAGTTCTCTCCGTGGATCTTAGTTCC<br>GCACATCGGTTACGGTTTCCAC<br>CAGTACCTGCCGTACCCGGACGGTATGTCTCCGTTCCAGGCTGCTATGG<br>TTGACGGTTCT<br>GGTTACCAGGTTCACCGTACCATGCAGTTCGAAGACGGTGCTTCTCTGA<br>CCGTTAACTAC<br>CGTTACACCTACGAAGGTTCTCACATCAAAGGTGAAGCTCAGGTTAAAG<br>GTACCGGTTTC<br>CCGGCTGACGGTCCGGTTATGACCAACTCTCTGACCGCTGCTGACTGGT<br>GCCGTTCTAAA<br>AAAACCTACCCGAACGACAAAACCATCATCTCTACCTTCAAATGGTCTT<br>ACACCACCGGT<br>AACGGTAAACGTTACCGTTCTACCGCTCGTACCACCTACACCTTCGCTA<br>AACCGATGGCT<br>GCTAACTACCTGAAAAACCAGCCGATGTACGTTTTCCGTAAAACCGAAC<br>TGAAACACTCT<br>AAAACCGAACTGAACTTCAAAGAATGGCAGAAAGCTTTCACCGACGTTA<br>TGGGTATGGACGAACTGTACAAA<br>GGCGGTGGCAGCGGCGGTGGCAGC<br>GCTGAGGGTGACGATCCCGCAAAA<br>GCGGCCTTTAACTCCCTGCAAGCCTCAGCGACCGAATATATCGGTTATG<br>CGTGGGCGATG<br>GTTGTTGTCATTGTCGGCGCAACTATCGGTATCAAGCTGTTTAAGAAAT<br>TCACCTCGAAAGCAAGC |
| E or 20 | Parts 1, 2, 3, 4 (NO FLAG) (i.e. TorAB7, mNG, linker, full pVIII) 334 residues total | MNNNDLFQTS RQRFLAQLGG LTVAGMLGPS<br>LLTPRRATAA GVSKGEEDNM ASLPATHELH<br>IFGSINGVDF DMVGQGTGNP NDGYEELNLK<br>STKGDLQFSP WILVPHIGYG FHQYLPYPDG<br>MSPFQAAMVD GSGYQVHRTM QFEDGASLTV<br>NYRYTYEGSH IKGEAQVKGT GFPADGPVMT<br>NSLTAADWCR SKKTYPNDKT IISTFKWSYT<br>TGNGKRYRST ARTTYTFAKP MAANYLKNQP<br>MYVFRKTELK HSKTELNFKE WQKAFTDVMG<br>MDELYKGGGS GGGSAEGDDP AKAAFNSLQA<br>SATEYIGYAW AMVVVIVGAT IGIKLFKKFT SKAS |
| F or 21 | nt sequence of E | ATGAACAATAACGATCTCTTTCAGACATCACGTCAGCGTTTTTTGGCAC<br>AACTCGGCGGCTTAACCGTCGCCGGGATGCTGGGGCCGTCATTGTTAAC<br>GCCGCGACGTGCGACT<br>GCGGCGGGC<br>GTTTCTAAAGGTGAAGAAGACAACATGGCTTCTCTGCCGGCTACCCACG<br>AACTGCACATCTTCGGTTCTATCAACGGTGTTGACTTCGACATG<br>GTTGGTCAGGGTACCGGTAACCCGAACGACGGTTACGAAGAACTGAACC<br>TGAAATCTACCAAAGGTGACCTGCAGTTCTCTCCGTGGATCTTAGTTCC<br>GCACATCGGTTACGGTTTCCAC<br>CAGTACCTGCCGTACCCGGACGGTATGTCTCCGTTCCAGGCTGCTATGG<br>TTGACGGTTCT<br>GGTTACCAGGTTCACCGTACCATGCAGTTCGAAGACGGTGCTTCTCTGA<br>CCGTTAACTAC<br>CGTTACACCTACGAAGGTTCTCACATCAAAGGTGAAGCTCAGGTTAAAG<br>GTACCGGTTTC<br>CCGGCTGACGGTCCGGTTATGACCAACTCTCTGACCGCTGCTGACTGGT<br>GCCGTTCTAAA<br>AAAACCTACCCGAACGACAAAACCATCATCTCTACCTTCAAATGGTCTT<br>ACACCACCGGT<br>AACGGTAAACGTTACCGTTCTACCGCTCGTACCACCTACACCTTCGCTA<br>AACCGATGGCT |

-continued

| SEQ ID NO: | Description | Sequence |
|---|---|---|
| | | GCTAACTACCTGAAAAACCAGCCGATGTACGTTTTCCGTAAAACCGAAC<br>TGAAACACTCT<br>AAAACCGAACTGAACTTCAAAGAATGGCAGAAAGCTTTCACCGACGTTA<br>TGGGTATGGACGAACTGTACAAA<br>GGCGGTGGCAGCGGCGGTGGCAGC<br>GCTGAGGGTGACGATCCCGCAAAA<br>GCGGCCTTTAACTCCCTGCAAGCCTCAGCGACCGAATATATCGGTTATG<br>CGTGGGCGATG<br>GTTGTTGTCATTGTCGGCGCAACTATCGGTATCAAGCTGTTTAAGAAAT<br>TCACCTCGAAAGCAAGC |
| G or 22 | 1, 2, 3, 4, 5 (i.e. TorAB7, mNG, linker, full pVIII + FLAG) 342 residues total | MNNNDLFQTS RQRFLAQLGG LTVAGMLGPS<br>LLTPRRATAA DYKDDDDKG VSKGEEDNM ASLPATHELH<br>IFGSINGVDF DMVGQGTGNP NDGYEELNLK<br>STKGDLQFSP WILVPHIGYG FHQYLPYPDG<br>MSPFQAAMVD GSGYQVHRTM QFEDGASLTV<br>NYRYTYEGSH IKGEAQVKGT GFPADGPVMT<br>NSLTAADWCR SKKTYPNDKT IISTFKWSYT<br>TGNGKRYRST ARTTYTFAKP MAANYLKNQP<br>MYVFRKTELK HSKTELNFKE WQKAFTDVMG<br>MDELYKGGGS GGGSAEGDDP AKAAFNSLQA<br>SATEYIGYAW AMVVVIVGAT IGIKLFKKFT SKAS |
| H or 23 | nt sequence of G | ATGAACAATAACGATCTCTTTCAGACATCACGTCAGCGTTTTTTGGCAC<br>AACTCGGCGGCTTAACCGTCGCCGGGATGCTGGGGCCGTCATTGTTAAC<br>GCCGCGACGTGCGACT<br>GCGGCG<br>GATTACAAGGATGACGATGACAAG GGC<br>GTTTCTAAAGGTGAAGAAGACAACATGGCTTCTCTGCCGGCTACCCACG<br>AACTGCACATCTTCGGTTCTATCAACGGTGTTGACTTCGACATG<br>GTTGGTCAGGGTACCGGTAACCCGAACGACGGTTACGAAGAACTGAACC<br>TGAAATCTACCAAAGGTGACCTGCAGTTCTCTCCGTGGATCTTAGTTCC<br>GCACATCGGTTACGGTTTCCAC<br>CAGTACCTGCCGTACCCGGACGGTATGTCTCCGTTCCAGGCTGCTATGG<br>TTGACGGTTCT<br>GGTTACCAGGTTCACCGTACCATGCAGTTCGAAGACGGTGCTTCTCTGA<br>CCGTTAACTAC<br>CGTTACACCTACGAAGGTTCTCACATCAAAGGTGAAGCTCAGGTTAAAG<br>GTACCGGTTTC<br>CCGGCTGACGGTCCGGTTATGACCAACTCTCTGACCGCTGCTGACTGGT<br>GCCGTTCTAAA<br>AAAACCTACCCGAACGACAAAACCATCATCTCTACCTTCAAATGGTCTT<br>ACACCACCGGT<br>AACGGTAAACGTTACCGTTCTACCGCTCGTACCACCTACACCTTCGCTA<br>AACCGATGGCT<br>GCTAACTACCTGAAAAACCAGCCGATGTACGTTTTCCGTAAAACCGAAC<br>TGAAACACTCT<br>AAAACCGAACTGAACTTCAAAGAATGGCAGAAAGCTTTCACCGACGTTA<br>TGGGTATGGACGAACTGTACAAA<br>GGCGGTGGCAGCGGCGGTGGCAGC<br>GCTGAGGGTGACGATCCCGCAAAA<br>GCGGCCTTTAACTCCCTGCAAGCCTCAGCGACCGAATATATCGGTTATG<br>CGTGGGCGATG<br>GTTGTTGTCATTGTCGGCGCAACTATCGGTATCAAGCTGTTTAAGAAAT<br>TCACCTCGAAAGCAAGC |
| I or 24 | First 90 nt of pVIII | GCTG<br>AGGGTGACGATCCCGCAAAAGCGGCCTTTAACTCCCTGCAA<br>GCCTCAGCGACCGAATATATCGGTTATGCGTGGGCGATGGT<br>TGTT |
| J or 25 | aas corresponding to first 90 nt of pVIII | AEGDDP AKAAFNSLQASATEYIGYAW AMVV |
| K or 26 | Parts 1, 2, 3, 4N-t (NO FLAG) (i.e. TorAB7, mNG, linker, N-t pVIII) | MNNNDLFQTS RQRFLAQLGG LTVAGMLGPS<br>LLTPRRATAA GVSKGEEDNM ASLPATHELH<br>IFGSINGVDF DMVGQGTGNP NDGYEELNLK<br>STKGDLQFSP WILVPHIGYG FHQYLPYPDG<br>MSPFQAAMVD GSGYQVHRTM QFEDGASLTV<br>NYRYTYEGSH IKGEAQVKGTGFPADGPVMT<br>NSLTAADWCR SKKTYPNDKTIISTFKWSYT<br>TGNGKRYRST ARTTYTFAKP MAANYLKNQP |

-continued

| SEQ ID NO: | Description | Sequence |
|---|---|---|
| | 314 residues | MYVFRKTELK HSKTELNFKE WQKAFTDVMG MDELYKGGGS GGGSAEGDDP AKAAFNSLQA SATEYIGYAWAMVV |
| L or 27 | nt sequence of K | ATGAACAATAACGATCTCTTTCAGACATCACGTCAGCGTTTTTGGCAC<br>AACTCGGCGGCTTAACCGTCGCCGGGATGCTGGGGCCGTCATTGTTAAC<br>GCCGCGACGTGCGACT<br>GCGGCGGGC<br>GTTTCTAAAGGTGAAGAAGACAACATGGCTTCTCTGCCGGCTACCCACG<br>AACTGCACATCTTCGGTTCTATCAACGGTGTTGACTTCGACATG<br>GTTGGTCAGGGTACCGGTAACCCGAACGACGGTTACGAAGAACTGAACC<br>TGAAATCTACCAAGGTGACCTGCAGTTCTCTCCGTGGATCTTAGTTCC<br>GCACATCGGTTACGGTTTCCAC<br>CAGTACCTGCCGTACCCGGACGGTATGTCTCCGTTCCAGGCTGCTATGG<br>TTGACGGTTCT<br>GGTTACCAGGTTCACCGTACCATGCAGTTCGAAGACGGTGCTTCTCTGA<br>CCGTTAACTAC<br>CGTTACACCTACGAAGGTTCTCACATCAAAGGTGAAGCTCAGGTTAAAG<br>GTACCGGTTTC<br>CCGGCTGACGGTCCGGTTATGACCAACTCTCTGACCGCTGCTGACTGGT<br>GCCGTTCTAAA<br>AAAACCTACCCGAACGACAAAACCATCATCTCTACCTTCAAATGGTCTT<br>ACACCACCGGT<br>AACGGTAAACGTTACCGTTCTACCGCTCGTACCACCTACACCTTCGCTA<br>AACCGATGGCT<br>GCTAACTACCTGAAAAACCAGCCGATGTACGTTTTCCGTAAAACCGAAC<br>TGAAACACTCT<br>AAAACCGAACTGAACTTCAAAGAATGGCAGAAAGCTTTCACCGACGTTA<br>TGGGTATGGACGAACTGTACAAA<br>GGCGGTGGCAGCGGCGGTGGCAGC<br>GCTG<br>AGGGTGACGATCCCGCAAAAGCGGCCTTTAACTCCCTGCAA<br>GCCTCAGCGACCGAATATATCGGTTATGCGTGGGCGATGGT<br>TGTT |
| M or 28 | Parts 1, 2, 3, 4N-t, 5 (i.e. TorAB7, mNG, linker, N-t pVIII + FLAG) 322 residues | MNNNDLFQTS RQRFLAQLGG LTVAGMLGPS LLTPRRATAA DYKDDDDK GVSKGEEDNM ASLPATHELH IFGSINGVDF DMVGQGTGNP NDGYEELNLK STKGDLQFSP WILVPHIGYG FHQYLPYPDG MSPFQAAMVD GSGYQVHRTM QFEDGASLTV NYRYTYEGSH IKGEAQVKGTGFPADGPVMT NSLTAADWCR SKKTYPNDKTIISTFKWSYT TGNGKRYRST ARTTYTFAKP MAANYLKNQP MYVFRKTELK HSKTELNFKE WQKAFTDVMG MDELYKGGGS GGGSAEGDDP AKAAFNSLQA SATEYIGYAWAMVV |
| N or 29 | nt sequence of M | ATGAACAATAACGATCTCTTTCAGACATCACGTCAGCGTTTTTGGCAC<br>AACTCGGCGGCTTAACCGTCGCCGGGATGCTGGGGCCGTCATTGTTAAC<br>GCCGCGACGTGCGACT<br>GCGGCG<br>GATTACAAGGATGACGATGACAAG GGC<br>GTTTCTAAAGGTGAAGAAGACAACATGGCTTCTCTGCCGGCTACCCACG<br>AACTGCACATCTTCGGTTCTATCAACGGTGTTGACTTCGACATG<br>GTTGGTCAGGGTACCGGTAACCCGAACGACGGTTACGAAGAACTGAACC<br>TGAAATCTACCAAGGTGACCTGCAGTTCTCTCCGTGGATCTTAGTTCC<br>GCACATCGGTTACGGTTTCCAC<br>CAGTACCTGCCGTACCCGGACGGTATGTCTCCGTTCCAGGCTGCTATGG<br>TTGACGGTTCT<br>GGTTACCAGGTTCACCGTACCATGCAGTTCGAAGACGGTGCTTCTCTGA<br>CCGTTAACTAC<br>CGTTACACCTACGAAGGTTCTCACATCAAAGGTGAAGCTCAGGTTAAAG<br>GTACCGGTTTC<br>CCGGCTGACGGTCCGGTTATGACCAACTCTCTGACCGCTGCTGACTGGT<br>GCCGTTCTAAA<br>AAAACCTACCCGAACGACAAAACCATCATCTCTACCTTCAAATGGTCTT<br>ACACCACCGGT<br>AACGGTAAACGTTACCGTTCTACCGCTCGTACCACCTACACCTTCGCTA<br>AACCGATGGCT<br>GCTAACTACCTGAAAAACCAGCCGATGTACGTTTTCCGTAAAACCGAAC<br>TGAAACACTCT<br>AAAACCGAACTGAACTTCAAAGAATGGCAGAAAGCTTTCACCGACGTTA<br>TGGGTATGGACGAACTGTACAAA<br>GGCGGTGGCAGCGGCGGTGGCAGC<br>GCTG |

-continued

| SEQ ID NO: | Description | Sequence |
|---|---|---|
| | | AGGGTGACGATCCCGCAAAAGCGGCCTTTAACTCCCTGCAA GCCTCAGCGACCGAATATATCGGTTATGCGTGGGCGATGGT TGTT |
| 30 | SD weak nt | AGGAGA |
| 31 | SD strong nt | TTAACTTTAAGAAGGAGATATACAT |
| | Tor A signal sequence nt | |
| 32 | Tor A aa | MNNNDLFQASRRRFLAQLGGLTVAGMLGPSLLTPRRAT |
| 60 | pVIII clone F03 nt | GCTGAGGGTGACGATCCCGCAAAA GCGGCCTTTAACTCCCTGCAAGCCTCAGCGACCGAATATATCGGTTATG CGTGGGCGATG GTTGTTGTCATTATAGGCGCCACTATCGGTATCAAGCTGTTTAAGAAAT TCACCTCGAAAGCAAGC |
| 61 | pVIII clone F03 aa | AEGDDP AKAAFNSLQASATEYIGYAW AMVVVIIGAT IGIKLFKKFT SKAS |

All sequences in this Table are recited herein 5' to 3' in line with convention in this technical field.

The invention will be further described with reference to the following non-limiting Examples with reference to the following drawings in which:

FIG. 1A shows a schematic overview illustrating some of the components of the fluorophore-pVIII phagemid constructs described herein. SD=Shine Dalgarno sequence (which can be weak or strong); Sig Sequence=Signal Sequence (shown here as TorAB7 but can be any signal sequence that directs the protein to the TAT secretory pathway); FLAG=FLAG tag; pVIII=phage pVIII coat protein. The boxes show variants of the various components in the SD, Sig Seq and Fluorophore parts of the vector which were made and tested. All variants were identical in sequence apart from the indicated variations. FIG. 1B shows a cartoon of a fluorophore-pVIII display Fluorophage particle. The phage particles will have multiple copies of the fluorophore randomly distributed along the length of the phage particle.

FIG. 2A shows a schematic overview illustrating some of the components of a dual display phagemid construct described herein. Lac=lac promoter; SD=Shine Dalgarno sequence; POI=protein of interest; pIX=phage pIX coat protein; Sig Sequence=Signal Sequence; FLAG=FLAG tag; pVIII=phage pVIII coat protein. The boxes show the variants of the various components in the SD, Sig Seq and Fluorophore parts of the vector which were made and tested. All variants were identical in sequence apart from the indicated variations. FIG. 2B shows a cartoon of a dual display Fluorophage particle. The phage particles will have one or multiple copies of the POI displayed on pIX depending on helper phage, and multiple copies of the fluorophore randomly distributed along the length of the phage particle.

Figure 3:
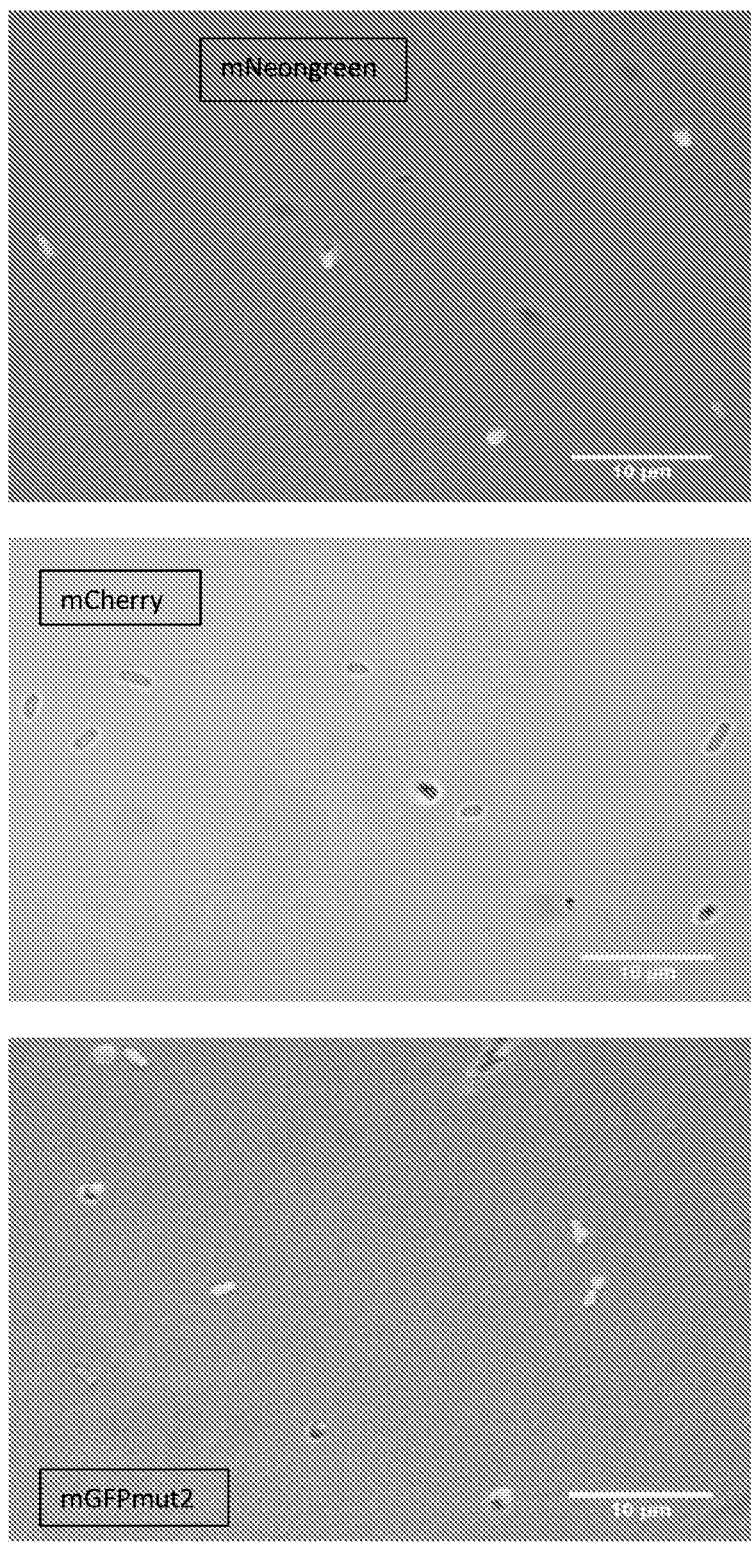

FIG. 3 shows E. coli staining with phagemid constructs containing the fluorophores mNeonGreen, mCherry and mGFPmut2 fused to pVIII. Transformed E. coli cells were grown overnight at 30° C. to allow for expression of the fluorophore. Cell cultures were added to glass slides and fluorescence was visualized using a confocal microscope. mNeongreen and eGFPmut2 show clear and bright fluorescence in most cells. mCherry shows weak but detectable fluorescence.

Figure 4:
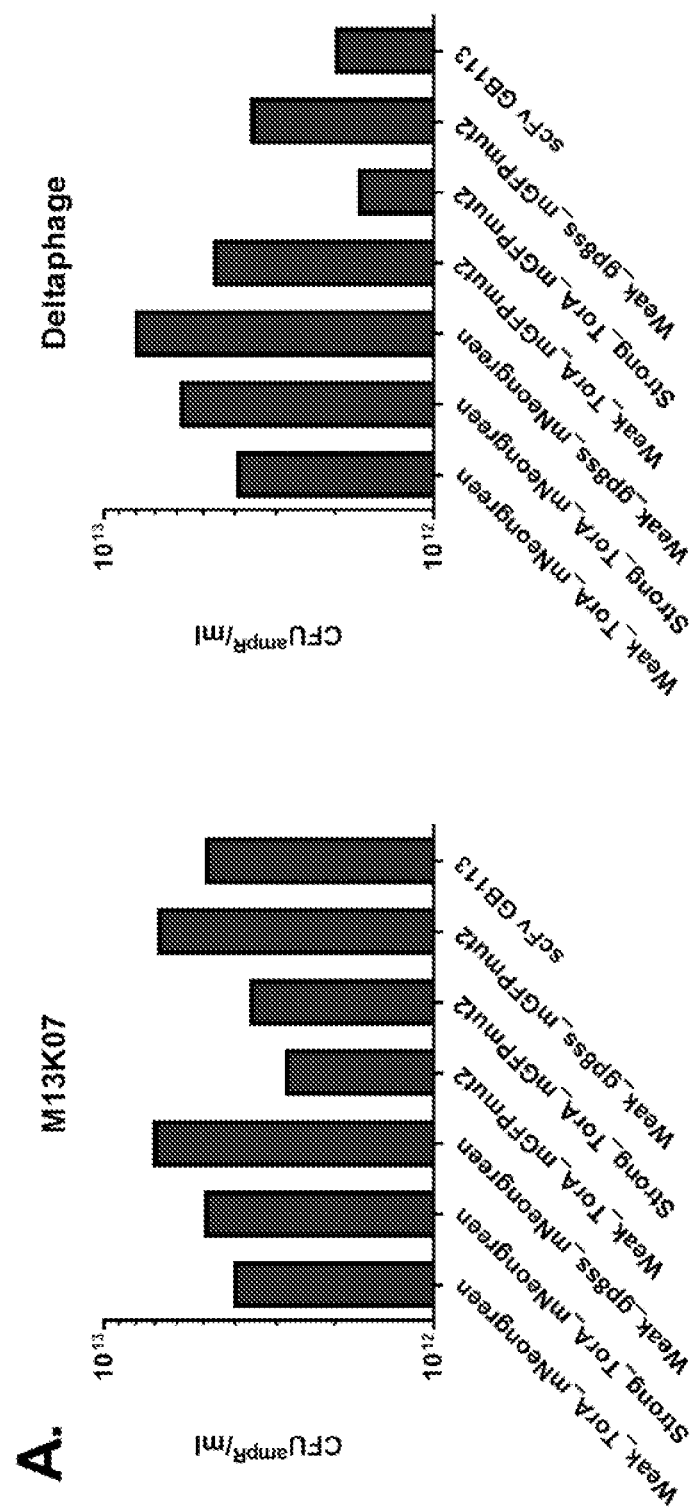
Figure 4:
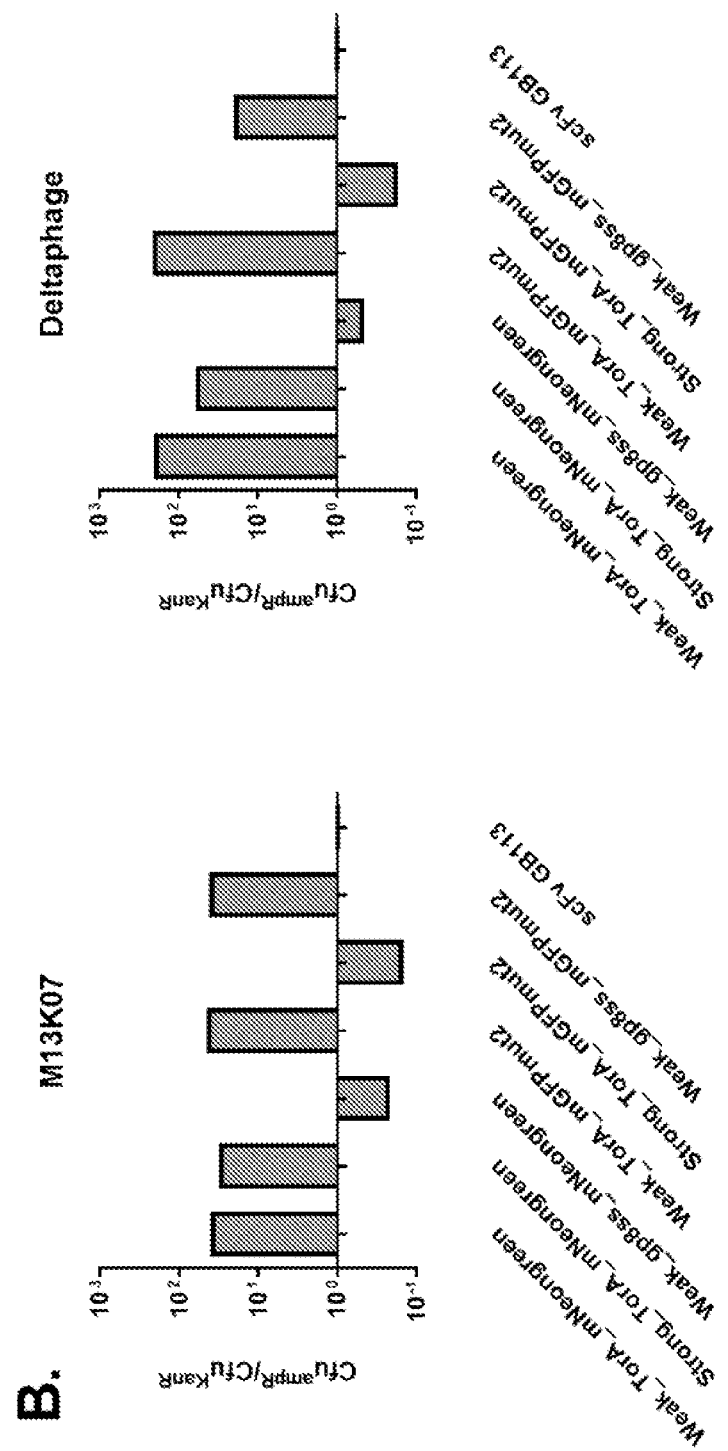
Figure 4:
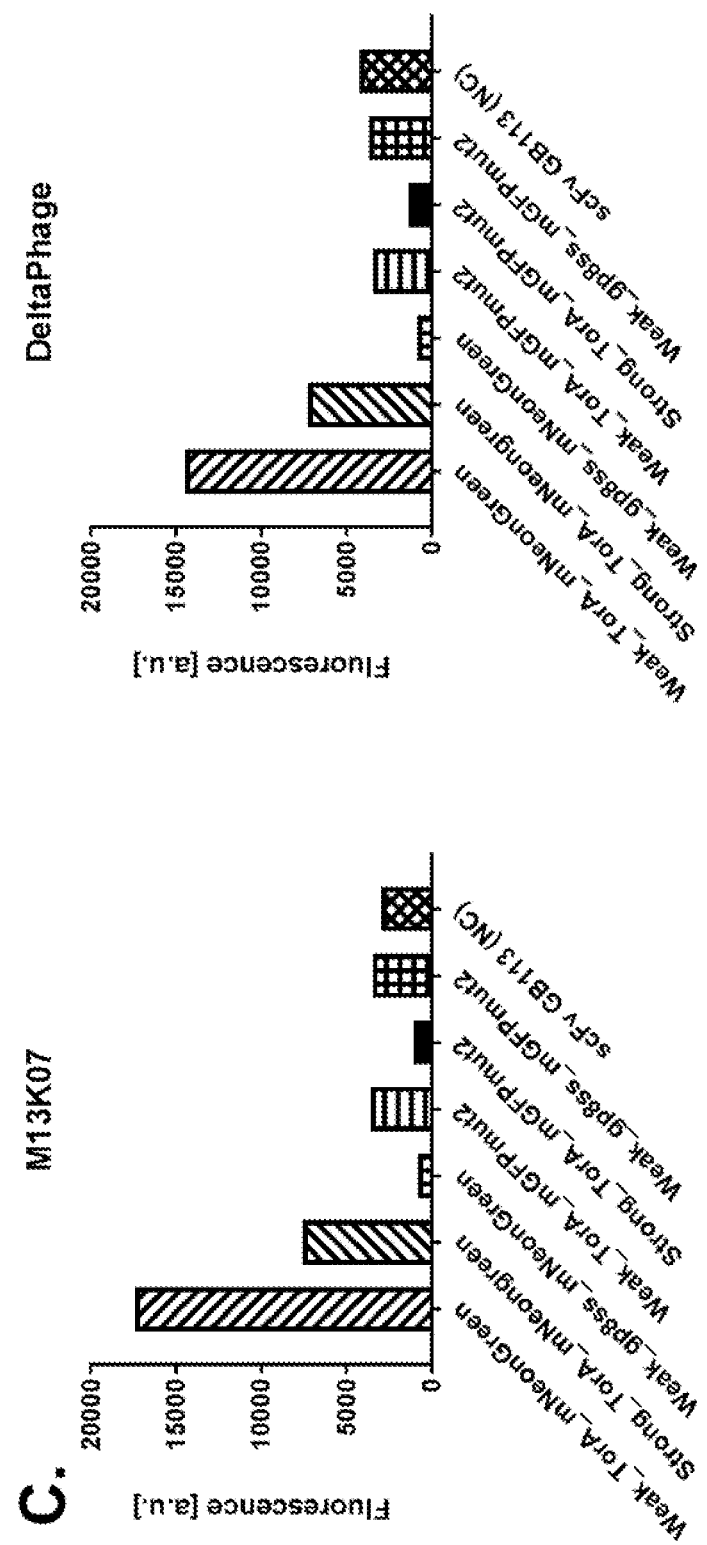

FIG. 4 shows an assessment of Fluorophage in phagemid rescue. A) Six variants of the Fluorophage phagemids containing weak or strong SD sequences, Tor AB7 or gp8 signal sequences, and mNeongreen or mGFPmut2 fluorophores, were propagated in 100 ml cultures of E. coli TOP10F' followed by rescue by either M13K07 or Deltaphage helper phages. Phages were concentrated by PEG precipitation followed by infectious titration, and the results given as $cfu^{ampR}$/ml. B) Phagemid to helper phage ratios were determined by $cfu^{ampR}/cfu^{kanR}$. C) Rescued Fluorophage particles were normalized to $1 \times 10^{12}$ $cfu^{ampR}$ and tested for fluorescence in a Victor$^3$ multilabel plate reader using a FITC filter. Fluorescence intensity is given as arbitrary units.

FIG. 5 shows an assessment of the effect on fluorescence intensity by use of different E. coli strains. A) Four different E. coli strains were transduced with the Fluorophage with or without a FLAG-tag and grown overnight and normalized on $OD_{600nm}$. Bacterial fluorescence was measured with the varioskan multimode plate reader and fluorescence intensity is given as arbitrary units. B) Normalized Fluorophage samples (Fluorophage particles) rescued using DeltaPhage from four different strains were analyzed for fluorescent intensity in the varioskan multimode plate reader. Fluorescence intensity is given as arbitrary units.

FIG. 6 shows evaluation of Fluorophage performance in ELISA and FLISA. A) Normalized phage samples were analyzed for fluorescence intensity on the Victor$^3$ plate reader and intensity is given as arbitrary units. B) A dilution series of normalized phage samples were added to wells either coated with 1 µg/ml phOx-BSA or milk block. Captured phages were detected with an anti-M13 HRP mAb and developed with soluble TMB. C) The same dilution series were analyzed for fluorescent signal in the Victor$^3$ plate reader in parallel.

Figure 7:
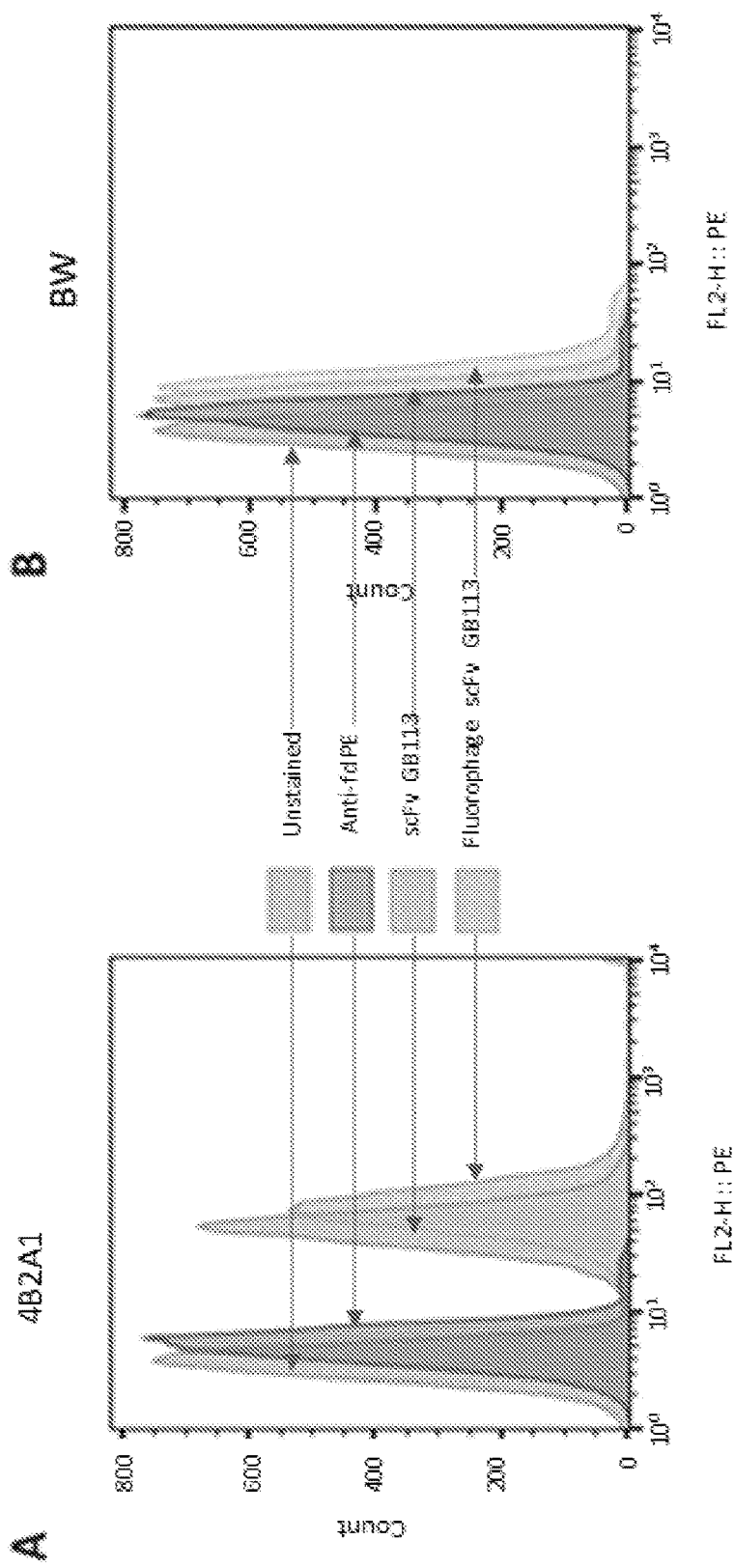
Figure 7:
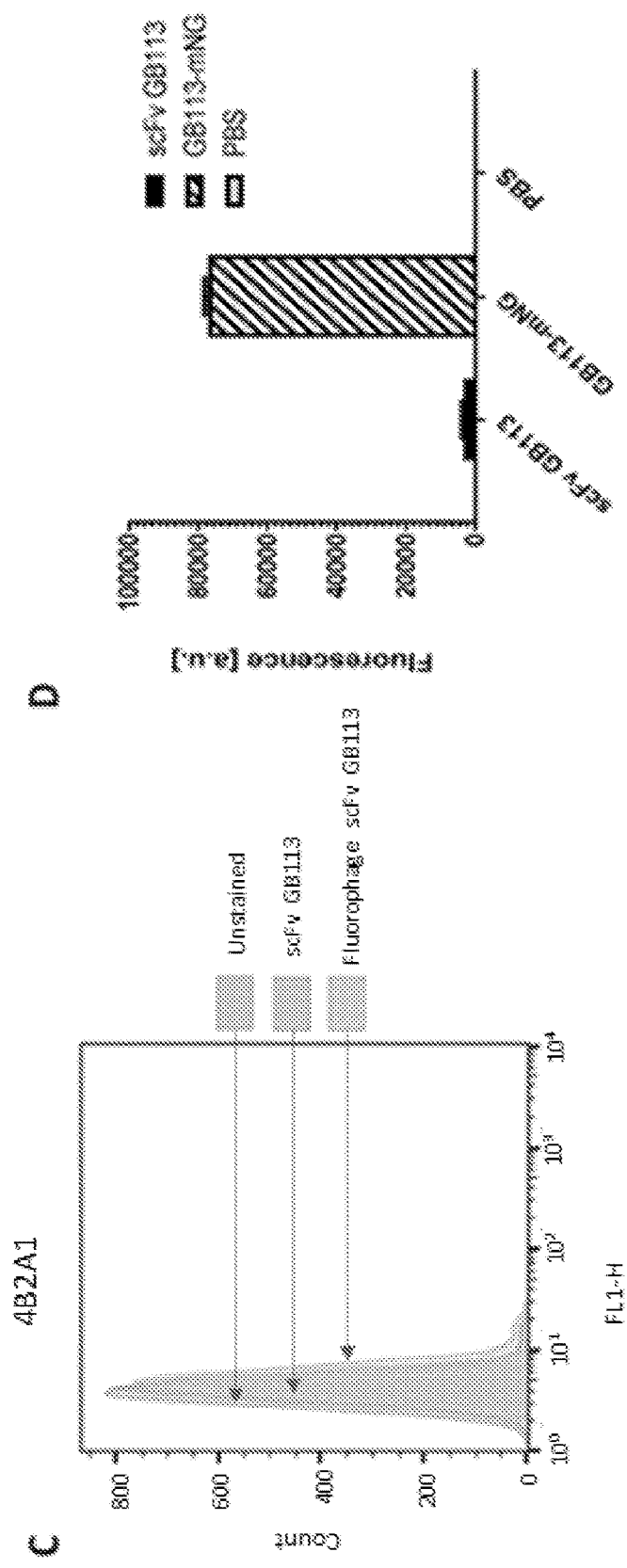

FIG. 7 shows fluorophage staining of BW TCR 4B2A1 cells by flow cytometry. A normalized phage input of $5 \times 10^{11}$ cfu/ml to $2 \times 10^5$ cells was used throughout. A) Staining of transfected BW 4B2A1 cells. Bound phages were detected with PE-conjugated anti-FD IgY. B) Staining of untransfected BW cells. Bound phages were detected with PE-conjugated anti-FD IgY. C) Staining of BW 4B2A1 cells. Bound phages were detected by intrinsic phage fluorescence. D) Normalized phage samples were analyzed for fluorescence intensity on the Victor$^3$ plate reader and intensity is given as arbitrary units.

Figure 8:
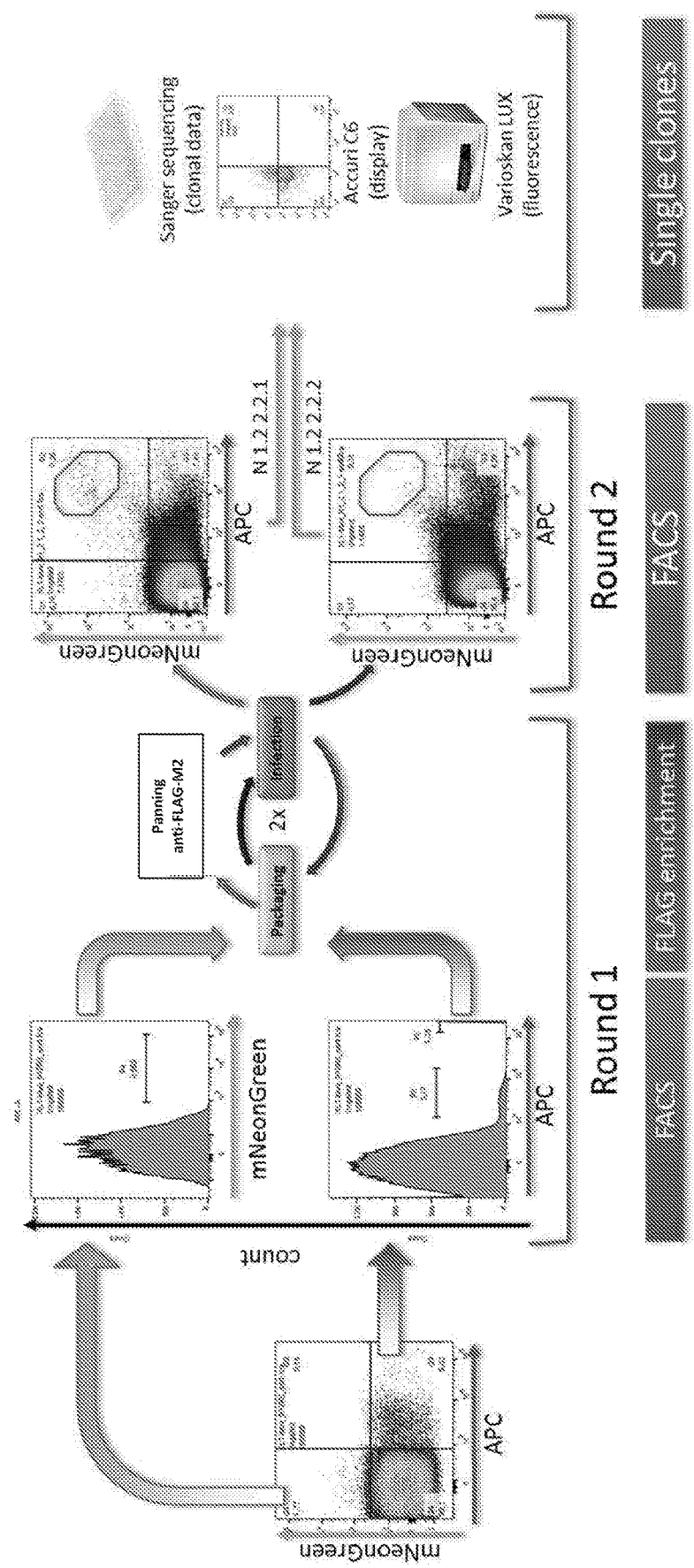

FIG. 8 shows an overview of the sorting/gating strategy used with the mutant library. Round 1 was a combination of cell based sorting and phage based enrichment of clones with high display level. Round 2 focused on clones with mNeonGreen signal and high levels of surface FLAG (double positive cells). Single clones were analysed using Sanger sequencing, Flow cytometry and fluorescence measurement.

FIG. 9 shows the sequence of FLAG_mNG_pVIII vector (which is a preferred embodiment of the invention); the nucleotide sequence is provided as SEQ ID NO:54 and the amino acid sequence as SEQ ID NO:55. The TorAB7, FLAG, mNG (mNeonGreen), linker and pVIII components of this vector are all shown.

Figure 10:
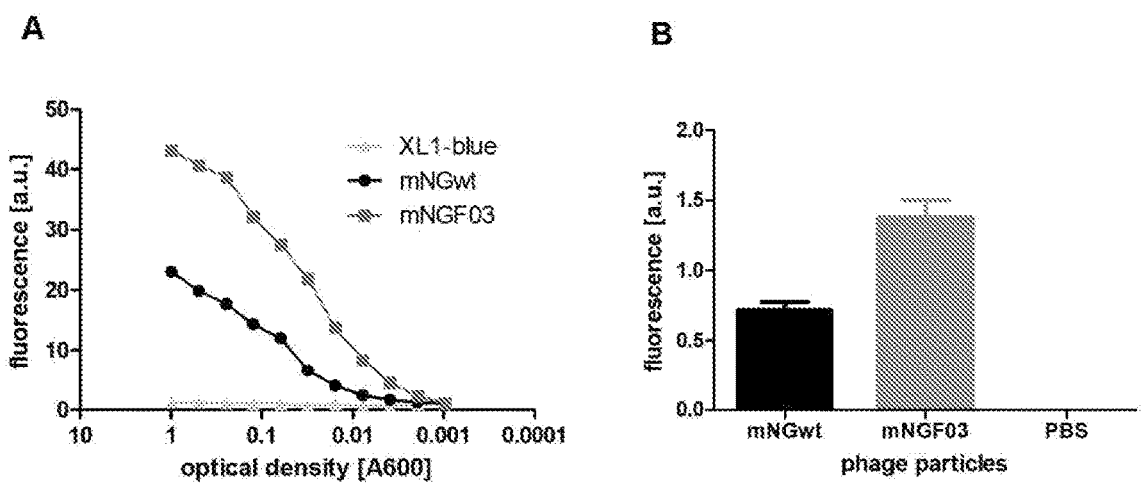

FIG. 10 shows the comparison of the original Fluorophage (mNGwt) with the lead candidate from the screening (mNGF03). (A) XL1-blue cells containing the different phagemids were cultured for 16 hours at 37 deg C. in the absence of glucose to allow expression of the fusion protein. Cells were washed 3× times in PBS. The optical density of the cells was measured, and all samples were adjusted based on the optical density, to an A600 value of 1. A serial dilution with 1:2 steps was prepared. (B) Phages were packaged following the standard protocol using Deltaphage. Sample concentrations were determined by infectious titration and all samples were normalized to 5.0e+12 CFU$^{AMP}$/mL. Fluorescence measurement was done in the Varioskan LUX at 488ex/517em.

Figure 11:
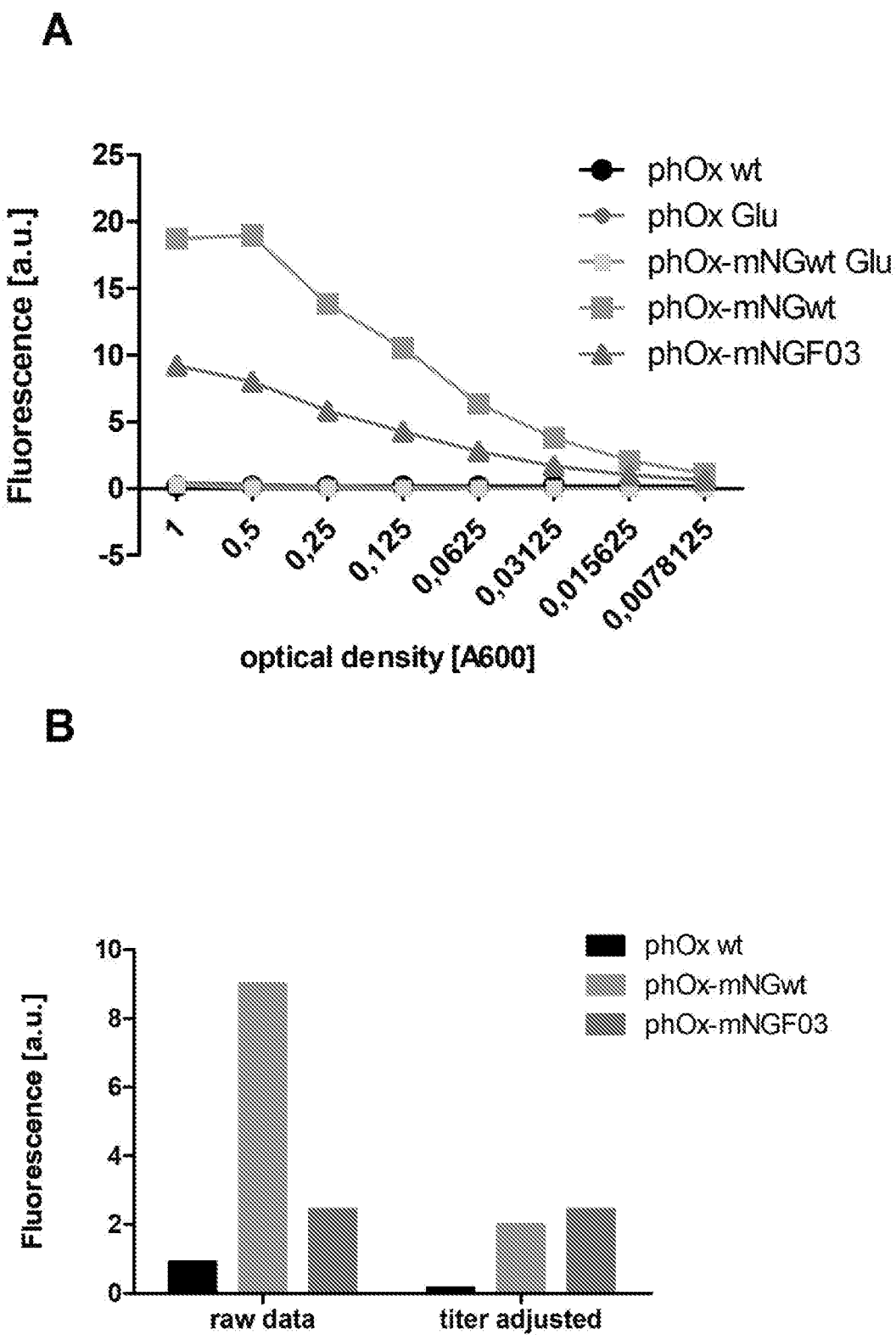

FIG. 11: Assessment of pVIII-mNGF03 clone in the context of the phOx-pIX fusion system. (A) Cells were taken during the packaging process. The fluorescence from the starting cultures (containing glucose) was measured to establish the baseline for the fluorescence measurement (Glu). The fluorescence of the same cells was measured after overnight packaging (absence of glucose). All samples were normalized based on the optical density, to an A600 value of 1. A serial dilution in 1:2 steps was prepared. (B) the phage concentration was determined based on the DNA amount present in the sample. Raw data was adjusted to the lowest value, 4,18E+12.

FIG. 12 shows the Fluorophage staining of SKW-3 R12-C9 cells by flow cytometry. A normalized phage input of $5×10^{12}$ cfu/ml to $5×10^4$ cells was used throughout. A) Staining of transfected SKW-3 R12-C9 cells. Bound phages were detected with APC-conjugated anti-FD IgY. B) Staining of untransfected SKW-3 cells. Bound phages were detected with APC-conjugated anti-FD IgY. C) Staining of SKW-3 R12-C9 cells. Bound phages were detected by intrinsic phage fluorescence. D) Normalized phage samples were analyzed for fluorescence intensity on the Varioskan LUX plate reader and intensity is given as arbitrary units.

Figure 13:
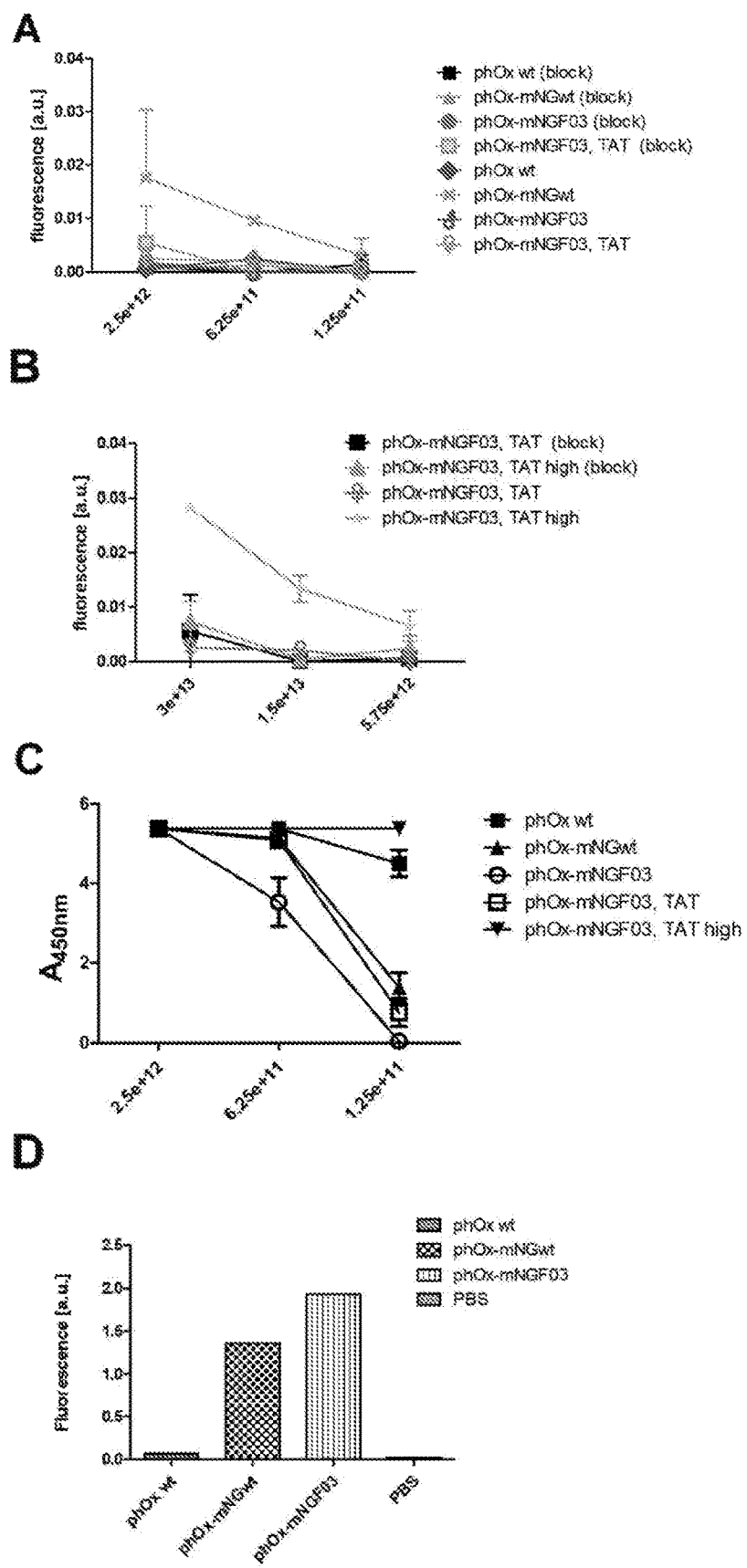

FIG. 13 shows the evaluation of Fluorophage performance in ELISA and FLISA. A,B) A dilution series of normalized phage samples (the different titers used in pNGF03, TAT high are indicated on the x-axis) were added to wells either coated with 1 µg/ml phOx-BSA or milk block. Captured phages were analyzed for fluorescent signal in the Varioskan LUX plate reader. C) The same samples were detected with an anti-M13 HRP mAb and developed with soluble TMB. (D) Normalized phage (5.0E+12 CFU$^{AMP}$/mL) samples were analyzed for fluorescence intensity on the Varioskan LUX plate reader and intensity is given as arbitrary units.

Figure 14:
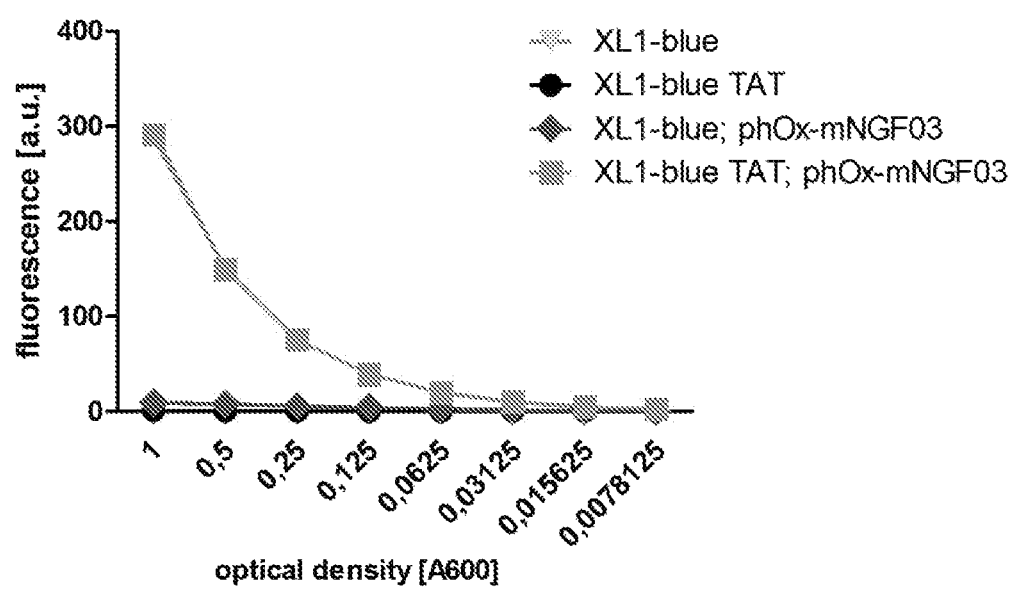

FIG. 14 shows the comparison of bacterial fluorescence level. XL1-blue cells containing expression vectors for the TAT AC and B genes in addition to the mNGF03 phagemid were cultured for 16 hours at 37 deg C. in the absence of glucose to allow expression of the fusion protein. Cells without phagemids were used as negative controls. The cells were washed 3× times in PBS. The optical density of the cells was measured, and all samples were adjusted based on the optical density, to an A600 value of 1. A serial dilution with 1:2 steps was prepared. Fluorescence measurement was done in the Varioskan LUX at 488ex/517em.

EXAMPLE 1—EFFICIENT M13 DISPLAY OF A FUNCTIONAL BIOLOGICAL FLUOROPHORE ON THE MAJOR CAPSID PROTEIN PVIII BY USING PERIPLASMIC TARGETING

Materials and Methods
Construction of the Dual Display Phagemid

All fluorophore-pVIII constructs were assembled in silico and ordered from Genscript (China). The fragments were inserted in the NheI cloning site in the pGALD9ΔLFN phagemid (Løset, G. Å., et al., 2011, *PLoS ONE*, 6, e17433, details of the vector also in Genbank HQ528250) carrying the scFv GB113 (Nilssen, et al., 2012, *Nucleic acids research*, 40, e120). Cloning procedure was confirmed by sequencing (GATC, Germany).

A gene fragment containing the FLAG-tag and N-terminal portion of mNeongreen was ordered from Genscript and inserted using the SnabI and BsgI restriction sites in order to create FLAG-mNeongreen. The general structure of this phagemid is shown in the schematic in FIG. 2A. Part of this vector sequence is shown in FIG. 9. Phagemids encoding the mCherry and the mGFPmut 2 fluorophores were made in an analogous way.

Phage Production

Five ml of 2×YT medium containing 100 µg/ml Ampicilline, 20 µg/ml tetracycline and 0.1 glucose (YT-TAG) were inoculated with cells from a glycerol stock of *E. coli* XL1-Blue containing the respective phagemid and grown overnight at 37° C. on an orbital shaker. 200 ml of YT-TAG were inoculated with the pre-culture at an OD$_{600}$ of 0.025 and grown at 37° C. with shaking. Cultures were infected with M0110 of helper phage DeltaPhage (Nilssen et al., 2012, supra), which is a helper phage with a conditional knockdown of its cognate pIX, allowing for high valence display of the pIX-POI, at an OD$_{600}$ of 0.3-0.4. After 60 min incubation the cultures were pelleted and resuspended in 2×YT supplemented with 100 µg/ml ampicillin and 50 µg/ml Kanamycin, and shaking was continued at 28° C. for 16 hrs. Bacterial cells were removed by centrifugation and filtering through 0.2 µm vacuum driven filters (Millipore), and mixed 1:5 with polyethylene glycol (PEG)/NaCl solution (20% PEG 8000, 2.5 M NaCl). After overnight incubation on ice, the sample was centrifuged (5000×g, 45 min, 4° C.) and the pellets were dissolved in 25 ml Phosphate-buffered saline (PBS). The samples were mixed 1:5 with PEG/NaCl and incubated for 4 h on ice followed by centrifugation as before, and pellets were resuspended in 1 ml PBS. Virion titers were assessed by infectious spot titration as described in Koch, J., et al., 2000, Biotechniques, 29, 1196-1198, 2002.

Fluorescence Measurements

Excitation/emission spectra were determined using an FP-8500 Spectrofluorometer (Jasco). In balancing the crosstalk versus sensitivity of the instrument we set the separation of excitation and emission to 15 nm while allowing the emission filter to accept ±2.5 nm of variation. The measurements were done with 5 nm intervals for both excitation and emission.

Fluorescence Measurement of Bacteria

Single colonies of E. coli harboring Fluorophage mNeongreen or Fluorophage mNeongreen-FLAG phagemids were inoculated in 5 ml 2×YT supplemented with 100 µg/ml Ampicillin and incubated over night at 37° C. The cells were pelleted, and resuspended in 1×PBS followed by normalization based on $OD_{600nm}$. The samples were prepared in 1:2 dilution series, and fluorescence was measured with the Varioskan multimode plate reader (Thermo Fischer) with appropriate ex/em setting for mNeongreen within the limitations of the instrument (500/525).

Confocal Microscopy of Bacteria on Glass Slides

Single colonies of E. coli harboring all three variants of mNeongreen, mGFPmut2 and mCherry Fluorophage phagemids were inoculated in 5 ml 2×YT supplemented with 100 µg/ml Ampicillin and incubated over night at 37° C. 3 µl of bacterial cultures were pipetted onto glass slides and glass cover slips were placed on top. The bacteria were visualized using a FV1000 Confocal Laser Scanning Microscope (Olympus) with appropriate available laser wave lengths for each fluorophore (488 nm: mNeongreen and mGFPmut2, 543 nm: mCherry).

Fluorescence Measurement of Phage

Fluorescence intensity measurements of phage were done by normalizing phage samples (diluted in 1×PBS) and measuring fluorescence with either the Victor$^3$ multilabel reader (PerkinElmer) with FITC-filter (488/510) at 1 s. excitation, or with the Varioskan multimode plate reader (Thermo Fischer) with appropriate ex/em setting for mNeongreen within the limitations of the instrument (500/525).

Phage Capture ELISA

Microtiter plates were coated with 1 µg/ml phOx-BSA over night at 4° C. and blocked with PBS with 0.1% Tween (X) and 4% non-fat skimmed milk powder (PBSTM). 1:4 serial dilutions of phage samples starting at $2.5 \times 10^{12}$ cfu/ml diluted in PBSTM were added in triplicate. Bound phage were detected by either anti-m13 HRP (Amersham Biosciences) followed by development with TMB solution and absorbance reading at 610 nm, or by fluorescence measurement in the Victor$^3$ multilabel reader.

Flow Cytometry

Aliquots of $2 \times 10^5$ BW 4B2A1 TCR transfectant and untransfected BW cells (negative control) were distributed into a V-shaped 96-well dish (NUNC). The total volumes were adjusted to 250 µl/well with 5% w/v FCS/PBS (pH 7.4). The plate was centrifuged at 300 g/5 min at RT and the supernatants discarded. Aliquots of 50 µl/well of phages with normalized titers of $5 \times 10^{11}$ cfu$^{ampR}$/ml pre-blocked in 5% FCS/PBS were added (Control wells received 5% FCS/PBS only) and the plate incubated for 1 h at 4° C. The cells were washed by adding 200 µl/well with 5% FCS/PBS, the cells pelleted by centrifuged at 300 g/5 min/RT and the supernatants discarded. PE-conjugated chicken Anti-fd (Norwegian Antibodies) in 5% FCS/PBS was added to the appropriate wells, and unstained samples received 5% FCS/PBS, followed by a 30 min incubation at 4° C. The wells were washed as above and fixed with 200 µl/well 2% PFA and kept in the dark until analysis on a FACScalibur (BD Biosciences). Data analysis was done using the FlowJo (v10.2) software.

Results and Discussion

Construction

A number of phagemid variants were designed based on the pGALD9ΔLFN (Løset, G. Å., et al., 2011, supra) phagemid vector (see FIGS. 1 and 2). In the case of the dual display phagemids as depicted in FIG. 2, such phagemids encode a protein of interest (POI) (herein an antibody fragment, scFv of the antibody GB113) fused to pIX. This system was chosen as it has previously been found that display on pIX performs highly favorably in e.g. antibody selection (Hoydahl, et al., 2016, Scientific reports, 6, 39066; Loset, G. A., et al., 2011, PLoS One, 6, e14702). The phagemid also encodes the periplamic chaperone FkpA for enhanced folding efficiency (Gunnarsen, et al., 2010, BMC Biotechnol, 10, 8). In order to display a targeting protein and a fluorophore on two different coat proteins simultaneously, the pVIII fusion was inserted directly after the termination of pIX in the phagemid. This allows the new ORF to be regulated by the same promoter (lac), thus allowing production of dual display phage particles with fusions to both pIX and pVIII (FIGS. 2A and 2B).

Some variations were included in the constructs (as shown in FIG. 2A). To investigate the effect of variations in translation intensity, we included either a weak SD (comprising the sequence AGGAGA, with the upstream region from the ATG start site of the Tat signal peptide having the sequence AAGGAGACAGTCATA) or a strong SD (the T7g10 TIR was used, which also includes an Epsilon sequence, TTAACTTTA, with the upstream region from the ATG start site of the Tat signal peptide having the sequence TTAACTTTAAGAAGGAGATATACAT). A stronger translation could force a greater amount of pVIII-fusions into the growing particle. To investigate the importance of translocation pathways, we introduced either gp8ss or TorAB7 as periplasmic targeting leader peptides. The leader peptide gp8ss provides targeting of the fusion to the Sec pathway of the secretory system, through which the protein is translocated in an unfolded state and allows folding to occur in the oxidizing environment of the periplasm (Manting, E. H. and Driessen, A. J., 2000, Mol Microbiol, 37, 226-238). The TorAB7 leader peptide has been engineered for improved periplasmic targeting of GFP (DeLisa et al., 2002, supra), and targets the fusion to the Twin Arginine Transport (TAT) pathway where the protein is folded in the reducing conditions of the cytoplasm prior to translocation. The fully folded protein is then translocated to the periplasm (Berks, B. C., et al., 2005, Curr Opin Microbiol, 8, 174-181).

To investigate how various fluorescent proteins perform as fusions to pVIII, three different fluorescent proteins were assessed: GFPmut2 (Cormack, B. P., et al., 1996, Gene, 173, 33-38.) which is a FACS-optimized version of GFP that was selected for a red-shift for optimal detection in FACS selection using a standard FITC filter from an E. coli library. The mutant GFP also proved to be an excellent folder when expressed in E. coli. Another green fluorescent protein, mNeongreen (Shaner, N.C., et al., 2013, Nat Methods, 10, 407-409) was chosen. We also chose to include mCherry (Shaner, N.C., et al., 2004, Nat Biotechnol, 22, 1567-1572.) based on the results of a previous study done with display of biological fluorophores (Speck et al., 2011, supra), where it was shown to be functionally displayed regardless of translocation route. Unless otherwise specified, the pIX-fusion was scFv GB113, an antibody fragment that exclusively reacts with the murine T cell receptor (TCR) 4B2A1 (Bogen, B., et al., 1990, *Eur J Immunol*, 20, 2359-2362.), and has previously been shown to perform well in flow cytometry when displayed on phage (Nilssen, N. R., et al., 2012, Nucleic acids research, 40, e120).

Phage Production and Validation

In order to confirm that the pVIII-fluorophore fusion did indeed produce fluorescent proteins, we inspected cultures of transformed *E. coli* cells using fluorescence microscopy. In preparation for this, we discovered that bacteria transformed with a phagemid harboring the combination of strong SD and SEC-targeted fluorescent protein did not grow in culture when the glucose repressor was removed, and thus this phagemid version was omitted from further experiments (data not shown).

Phagemid variants with the fluorophores mNeongreen, mCherry and mGFPmut2 (FIG. 2A) were transformed into *E. coli* which were then grown overnight at 30° C. to allow for expression of the fluorophore. These phagemid variants all contained a weak SD sequence and a TorAB7 signal sequence. Cell cultures were added to glass slides and fluorescence was visualised using a confocal microscope. The results are shown in FIG. 3 where it can be seen that mNeongreen and mGFPmut2 show clear and bright fluorescence and mCherry shows weak fluorescence. The presence of detectable levels of fluorescence with all three fluorophores demonstrates that the fluorophores are expressed and correctly folded. This fluorophore expression was confirmed by western blotting (data not shown). Thus, the above-described phagemid system is working to display functional fluorophore-pVIII fusion proteins.

As mNeongreen and mGFPmut2 showed better detectable fluorescence than mCherry further experiments were carried out with these constructs.

To evaluate whether the addition of a second coat protein fusion to the system would affect phage production and/or phagemid packaging, we produced all Fluorophage variants carrying the Green fluorescent proteins (mGFPmut2 and mNeongreen), and measured phage production and phagemid packaging by infectious titration (FIG. 4A). All phage samples reached end titers comparable to those previously observed in our pIX system (Loset et al., 2011, e17433, supra, and Nilssen et al., 2012, supra). Furthermore, as previously observed, phagemid rescue with DeltaPhage, a helper phage with a conditional knockdown of its cognate pIX, allowing for high valence display of the pIX-POI, did not appear to affect phage production (Nilssen et al., 2012, supra). The combination of weak SD and SEC-targeting caused preferential packaging of helper phage genome for mNeongreen, and the same effect was observed for strong SD and TAT targeting for mGFPmut2 (FIG. 4B). However, these results show that the dual display phagemids containing two coat protein fusions are packaged and allow phage production at equivalent levels to that seen when only a pIX fusion is present.

In order to assess the levels of functional fluorescent proteins presented on the Fluorophage particles, normalized Fluorophage samples were analyzed in the victor$^3$ multilabel reader using a FITC filter (488 nm/510 nm) (FIG. 4C). The combination of weak SD and TAT-targeted mNeongreen stood out as it exceeded background fluorescence by at least three-fold. However, the Fluorophage with a strong SD and TAT targeting also showed approximately two-fold higher intensity than background, while the intensity of, for example, the mGFPmut2 Fluorophage with a weak SD and TAT targeting was slightly above the background signal. Variations in display valence of the pIX POI did not appear to affect functional display levels of the fluorescent protein on pVIII. Reaching high end titers is highly important for downstream applications such as library selections, and the Fluorophages were not produced in lower numbers than previously observed in the pIX system. The Fluorophage construct did indeed produce fluorescent phage particles, and one of the variations, namely TAT-targeted mNeongreen with a weak SD reached a satisfactory signal to noise ratio. Worth noting here is that mNeongreen possesses a sharp excitation peak at 506 nm and a likewise sharp emission peak at 517 nm which does not match the fluorescein filter used in the Victor$^3$ (485 nm/535 nm). The intensity measured using this filter is likely to be highly underestimated. Regardless, the combination of weak SD and TAT targeted mNeongreen stood out as the best performing construct and was thus chosen for downstream characterization.

In order to investigate and verify the excitation and emission spectra of mNeongreen when displayed on pVIII, $2 \times 10^{11}$ phage particles/ml were analyzed on a Spectrofluorometer (data not shown). As a positive control we included 2 μg/ml of soluble eGFP which showed a clear and defined peak at the expected wavelengths (490 nm/510 nm). As a negative control we analyzed phage particles displaying the scFv GB113, but no fluorophore. Here we observed a sharp peak at 440 nm/455 nm. When analyzing the phage samples with display of mNeongreen, the same sharp peak appeared in addition to the peak that was expected from correctly folded mNeongreen at (505 nm/520 nm) (Shaner et al., 2013, supra).

Optimization of Functional Display

We wanted to investigate whether there were any differences in expression and folding in the standard lab strains of *E. coli* and whether any differences would translate into functional display levels. In addition, we wanted to include a detection tag for fluorescent protein expression, and added a FLAG tag to the N-terminus of mNeongreen. Four *E. coli* strains, XL1-Blue, AVB100F', SS320 and Top10F' were transformed with the Fluorophage±FLAG.

Fluorescence intensity was then measured directly in live *E. coli* cells (FIG. 5A). There was a clear difference in fluorescence between strains. Proteins expressed in XL1-blue gave the highest intensity, closely followed by AVB100F'. These two strains showed markedly higher fluorescence intensity than SS320 and TOP10F', although functional expression and folding was still clearly observed in these strains. To our surprise, we observed that the addition of the FLAG appeared to translate into higher overall fluorescence intensities. These FLAG containing constructs were then used to measure the fluorescence intensity from phage samples produced in the four individual strains (FIG. 5B), and again comparing the fluorescence of mNeongreen-FLAG from Fluorophage packaged in the four different strains (FIG. 5B), it became clear that XL1-blue was the superior strain, followed by AVB100F'. Phages packaged in SS320 and Top10F' gave poorer fluorescence intensities.

Even though they are closely related, the different strains showed quite large differences in functional expression and folding of the fluorophores. Moreover, although XL1-Blue and AVB100 were very similar in bacterial fluorescence when producing the pVIII-fluorophore fusion alone, Fluorophage particles produced in XL1-blue gave almost two-fold higher fluorescence intensity. These data suggest that the favourable ability to fold the fluorophore functionally in the cytosol is shared between XL1-Blue and AVB100, which contrast SS320 and TOP10F'. However, XL1-Blue appears to have a superior ability also compared with AVB100 to transport the folded fluorophore from cytosol to the periplasm and integrate it into the virion. Thus, although any of these strains (or indeed other E coli strains) can be used, XL1-blue is preferred in some cases.

Enzyme-Linked Immunosorbent Assay (ELISA) and Fluorescent-Linked Immunosorbent Assay (FLISA)

To assess whether or not we could combine the ability to display both a functional fluorophore-pVIII fusion and a different functional fusion on a different capsid than pVIII on the same phage particle, we chose to insert a well-described anti-phOx scFv (Marks et al., 1992, Biotechnology, 10:779-783) into the fluorophore-pVIII expressing phagemid as a pIX fusion. We then prepared phages and tested them for phox binding in classical ELISA as well as FLISA as described. For comparison, we prepared anti-phox scFv-pIX displaying phages without the fluorophore-pVIII fusion and tested in parallel.

The fluorescence intensity of normalized amounts of phage particles was measured in the Victor$^3$ plate reader (FIG. 6A) and showed very high fluorescence intensity, and only from the phages displaying the fluorophore-pVIII fusion. Importantly, when testing the same phage samples for scFv target binding in standard ELISA, specific and identical binding was observed independent of presence or absence of the fluorophore-pVIII fusion (FIG. 6B). Thus, the data demonstrate that display of a fluorophore on pVIII did not affect antigen binding mediated by the targeting moiety in the pIX fusion on dual display phage. When the same phage samples again were tested for target binding using FLISA employing the Victor$^3$ plate reader, we could not observe a fluorescent signal from any sample (FIG. 6C). Thus, the data show that measuring the fluorescence of all phages applied in the well is readily done, whereas in the current set-up we did not have the sensitivity to specifically detect the reduced amount of phages retained on target after washing in the FLISA. Importantly, the data irrevocably shows that dual display of the fluorophore-pVIII fusion and scFv-pIX fusion on the same phage particle does not affect the phenotype of the scFv-pIX fusion.

Detection of Cell Surface Expressed Proteins by Flow Cytometry

A powerful application of the Fluorophage would be to use it in real time selection on FACS without the need for staining antibodies, but only relying on the inherent fluorescence of the fluorophore-pVIII fusion for detection. To assess this, we tested the GB113 scFv-pIX displaying Fluorophage for specific binding to the T-cell receptor expressed on murine 4B2A1 T cell hybridoma cells using flow cytometry. For comparison, we prepared GB113 scFv-pIX displaying phages without the fluorophore-pVIII fusion and tested in parallel.

In order to verify specific binding to the cells expressing the TCR 4B2A1 using standard methodology, we used a PE-conjugated anti-fd antibody to detect bound phages. This also allowed a side-by-side comparison of the Fluorophage and the regular phage bound to the TCR (FIG. 7A), and neither bound to the TCR negative murine BW58 cells (PMID: 2558022) (FIG. 7B). When attempting to stain cells without the addition of a detection mAb, we observed no increase in fluorescence intensity compared to the controls (FIG. 7C), despite the strong fluorescence signal observed from the Fluorophage scFv GB113 when in solution (FIG. 7D). Thus, even though the Fluorophage exhibited strong fluorescent signal in solution, we were unable to detect it in binding to surface bound antigen using flow cytometry. This means that although this Fluorophage is highly useful and advantageous in many assays, the Fluorophage in this form does not yet reach the brightness per particle needed to allow direct staining and FACS sorting of cells.

Concluding Remarks

Previous efforts that attempt to build on the combined strengths of phage and cellular technologies have been reported, but have yet to see regular use. Functional display of fluorescent proteins on phage particles has been achieved previously, but has so far only shown limited success and has not been achieved on the pVIII coat protein. At this point, in vitro indirect coupling of a fluorophore to sortase tagged pVIII has shown the greatest promise (Hess et al., 2012, supra), but this procedure is inefficient, laborious and expensive.

We here show the generation of a phage particle with both intrinsic fluorescence capability and target binding activity. mNeongreen proved to be the superior fluorophore of those investigated for display on pVIII. We found that the optimal conditions for functional display of biological fluorophores on pVIII involved translocation of the fusion through the Tat pathway for cytosolic folding. We surprisingly also found that a weak SD gave higher functional display. The exact cause of this is unknown, but one might speculate that a form of overload of the E. coli folding machinery may occur. XL1-Blue was shown to give the highest fluorescence intensity to the produced phage particles.

Potential end use of this reagent is not limited to selection and screening of antibodies. Any protein that can be displayed on a phage can be inserted into Fluorophage phagemid to produce a single layer detection reagent.

Even though the Fluorophage exhibited strong fluorescence and will have advantageous utility in many assays due to its intrinsic fluorescence, thereby avoiding the use of labelled or staining reagents/antibodies, combined with its ability to bind to a target molecule via the second coat protein fusion to a POI, it was still not bright enough to be detected when bound to antigen. A possible way to achieve this might be to increase the brightness of the Fluorophage particles. This might theoretically be achieved by: 1) increasing the number of pVIII-mNeongreen per particle, or 2) improving functional display of mNeongreen by improving folding, or 3) increasing the intrinsic brightness of mNeongreen, or a combination of all.

To this end, we have advantageously been able to develop variants of the Fluorophage constructs which show improved efficacy (improved fluorescence properties).

EXAMPLE 2—GENERATION OF FLUOROPHAGE VARIANTS

Random mutation of amino acids in the sequence of the original (parent) mNeonGreen protein as described herein (SEQ ID NO:3 and 4) was carried out to assess whether it was possible to produce a version that is either brighter than the existing (parent) protein or shows an improved display as a pVIII-fusion in the phage coat. Ideally, we would identify a mutant that shows improvement in both categories. However, we were not sure that this would be possible.

We constructed a library that consists of Fluorophage vector variants carrying mutations in the mNeonGreen gene, the linker and the first 90 nucleotides of the pVIII gene.

The part of the construct which was subjected to mutagenesis is shown below (these three parts are found as consecutive sequences in the vector but have been shown separately here for clarity):

```
                                        (SEQ ID NO: 56)
GTTTCTAAAGGTGAAGAAGACAACATGGCTTCTCTGCCGGCTACCCACGA

ACTGCACATCTTCGGTTCTATCAACGGTGTTGACTTCGACATGGTTGGTC

AGGGTACCGGTAACCCGAACGACGGTTACGAAGAACTGAACCTGAAATCT

ACCAAAGGTGACCTGCAGTTCTCTCCGTGGATCTTAGTTCCGCACATCGG

TTACGGTTTCCACCAGTACCTGCCGTACCCGGACGGTATGTCTCCGTTCC

AGGCTGCTATGGTTGACGGTTCTGGTTACCAGGTTCACCGTACCATGCAG

TTCGAAGACGGTGCTTCTCTGACCGTTAACTACCGTTACACCTACGAAGG

TTCTCACATCAAAGGTGAAGCTCAGGTTAAAGGTACCGGTTTCCCGGCTG

ACGGTCCGGTTATGACCAACTCTCTGACCGCTGCTGACTGGTGCCGTTCT

AAAAAAACCTACCCGAACGACAAAACCATCATCTCTACCTTCAAATGGTC

TTACACCACCGGTAACGGTAAACGTTACCGTTCTACCGCTCGTACCACCT

ACACCTTCGCTAAACCGATGGCTGCTAACTACCTGAAAAACCAGCCGATG

TACGTTTTCCGTAAAACCGAACTGAAACACTCTAAAACCGAACTGAACTT

CAAAGAATGGCAGAAAGCTTTCACCGACGTTATGGGTATGGACGAACTGT

ACAAA (mNeonGreen)

GGCGGTGGCAGCGGCGGTGGCAGC (linker)

GCTGAGGGTGACGATCCCGCAAAAGCGGCCTTTAACTCCCTGCAAGCCTC

AGCGACCGAATATATCGGTTATGCGTGGGCGATGGTTGTT pVIII (partially, first 90 nucleotides),
```

Library Construction

We carried out incorporation of dNTP analogues by PCR to introduce random mutations into the phagemid DNA. Based on a paper by Zaccolo et al. (1996, J Mol Biol 255(4):589-603), Jena Biosciences produces and sells a PCR-based mutagenesis kit that was used during library generation. As a cloning tool we used the NEBuilder® HiFi DNA Assembly Cloning Kit. This kit will ligate any fragments with sequence overlaps between 15-80 nts.

Mutagenesis:

We created and characterized libraries of one fragment with different mutational loads based on the number of rounds/cycles used to incorporate dNTP analogues during PCR. We choose a fragment that contains the complete fluorophage pVIII-fusion gene (including all 5 functional domains, i.e. TorAB7, FLAG, mNG, linker and full length pVIII) and its flanking regions (see sequence below). Using this approach, we have the possibility to go back and amplify different regions to construct new libraries in the future without having to go through the mutagenesis process all over again:

The individual parts of this construct are shown below (these parts are found as consecutive sequences in the vector but have been shown separately here for clarity):

```
                                        (SEQ ID NO: 57)
AGTGTTTTAGTGTATTCTTTCGCCTCTTTCGTTTTAGGTTGGTGCCTTCG

TAGTGGCATTACGTATTTTACCCGTTTAATGGAAACTTCCTCATGATAAG

CTAGCAAGCAAGGAGACAGTCATA (flanking region)

ATGAACAATAACGATCTCTTTCAGACATCACGTCAGCGTTTTTTGGCACA
```

```
-continued
ACTCGGCGGCTTAACCGTCGCCGGGATGCTGGGGCCGTCATTGTTAACGC

CGCGACGTGCGACT (Tor AB7)

GCGGCG (amino acids AA)

Gattacaaggatgacgatgacaag (FLAG)

GGC (amino acid G)

GTTTCTAAAGGTGAAGAAGACAACATGGCTTCTCTGCCGGCTACCCACGA

ACTGCACATCTTCGGTTCTATCAACGGTGTTGACTTCGACATGGTTGGTC

AGGGTACCGGTAACCCGAACGACGGTTACGAAGAACTGAACCTGAAATCT

ACCAAAGGTGACCTGCAGTTCTCTCCGTGGATCTTAGTTCCGCACATCGG

TTACGGTTTCCACCAGTACCTGCCGTACCCGGACGGTATGTCTCCGTTCC

AGGCTGCTATGGTTGACGGTTCTGGTTACCAGGTTCACCGTACCATGCAG

TTCGAAGACGGTGCTTCTCTGACCGTTAACTACCGTTACACCTACGAAGG

TTCTCACATCAAAGGTGAAGCTCAGGTTAAAGGTACCGGTTTCCCGGCTG

ACGGTCCGGTTATGACCAACTCTCTGACCGCTGCTGACTGGTGCCGTTCT

AAAAAAACCTACCCGAACGACAAAACCATCATCTCTACCTTCAAATGGTC

TTACACCACCGGTAACGGTAAACGTTACCGTTCTACCGCTCGTACCACCT

ACACCTTCGCTAAACCGATGGCTGCTAACTACCTGAAAAACCAGCCGATG

TACGTTTTCCGTAAAACCGAACTGAAACACTCTAAAACCGAACTGAACTT

CAAAGAATGGCAGAAAGCTTTCACCGACGTTATGGGTATGGACGAACTGT

ACAAA (mNeonGreen)

GGCGGTGGCAGCGGCGGTGGCAGC (Linker)

GCTGAGGGTGACGATCCCGCAAAAGCGGCCTTTAACTCCCTGCAAGCCTC

AGCGACCGAATATATCGGTTATGCGTGGGCGATGGTTGTTGTCATTGTCG

GCGCAACTATCGGTATCAAGCTGTTTAAGAAATTCACCTCGAAAGCAAGC (pVIII full)

TGATAAGCTAGCTTGAGGCATCAATAAAACGAAAGGCTCAGTCGAAAGAC

TGGGCCTTTCATTTTATCTGTTGTTTGTCGGTTAACGCTTGTCGTCATCG

TCCTTGTAGTCTTTTTTAGCAGAATCTGCGGCTTTCGCATC

AGCTTCCGGCTTTGCATCAGC (flanking region),
```

This sequence was produced with following primers:

```
                                        (SEQ ID NO: 58)
    pVIII_fwd:       AGTGTTTTAGTGTATTCTTTCGCC (SEQ ID NO: 59)
    FkpA_R:          GCTGATGCAAAGCCGG
```

Sequences were analyzed using Sanger sequencing service by GATC (Germany). Up to 28 rounds (PCR cycles) of mutation were carried out which resulted in around 25% mutation frequency at the amino acid level (around 10% at the nucleotide level), data not shown.

The mutagenized fragments were cloned back into the vector as shown in FIG. 2 comprising a TorAB7 signal peptide and a FLAG tag. The sequence of the TorAB7, FLAG, mNG, Linker and pVIII components of this vector are as shown in FIG. 9.

Cloning of the Library:

The cloning process is straight forward and we strictly followed the recommendations of the NEBuilder® HiFi DNA Assembly Cloning Kit.

The complete ligation reaction was transformed into electro-competent SS320 to produce a library with high diversity. Titration based calculation of the library was 1.0E+06. We then prepared DNA from the SS320 cells and electroporated XL1-blue cells, the standard packaging strain for the Fluorophages.

The library was packaged with Hyperphage following standard packaging protocols and the mutant library members were screened by FACS.

Gating Strategy on the FACS ARIA IIu

An overview of the complete sorting strategy is shown in FIG. 8. We gated the library based on two characteristics: mNeonGreen performance (green; Alexa488) and display level of fusion protein (red; APC). (For the second characteristic, the level of surface bound mNeonGreen-pVIII fusion protein can be quantified using an anti-DYKDDDDK-APC conjugated antibody, i.e. a fluorescently labelled anti-FLAG tag antibody). The gating strategy in the first round was liberal regarding the signal strength of both channels. The sorted cells were packaged to produce the corresponding phage library. An anti-FLAG®-M2 coated immunotube was then used to enrich clones with fusion proteins integrated into the phage coat. Fresh XL1-blue cells were transduced with the output of this enrichment and the resulting cells were prepared for sorting as in round 1. The gating in round 2 was much more stringent and intended to sort double positive clones only.

It can be seen from the FACS profiles shown in FIG. 8 that library members with increased numbers of fluorophores on the surface and/or clones with increased mNeonGreen signal have been generated. See the shift of clones from the bottom left quadrant of the FACS panel on the left-hand side of FIG. 8 (which shows results before sorting), to the bottom right quadrant (high levels of surface FLAG, APC signal), the top left quadrant (increased mNeonGreen signal) or the top right quadrant (clones with both high levels of surface FLAG, APC signal, and increased mNeonGreen signal) seen in the Round 2 FACS profiles of FIG. 8 (i.e. after two rounds of sorting).

Such results show that obtaining variant fluorophages which have significantly increased and improved fluorescence from that observed when the parent mNeonGreen sequence was used can be achieved, and single clones can now be further characterised in order to select highly advantageous mutants.

EXAMPLE 3—CHARACTERIZATION OF A MUTANT FLUOROPHORE

The libraries prepared as described above can be screened for mutants showing improved fluorescence properties. One of the improved clones identified by these screenings is the so called F03 mutant as described herein. This F03 mutant was identified from one of the screenings which contained libraries with mutations in the full length pVIII. When sequenced the pVIII part of the F03 mutant had the nucleotide sequence:

(SEQ ID NO: 60)
GCTGAGGGTGACGATCCCGCAAAAGCGGCCTTTAACTCCCTGCAAGCCTC

AGCGACCGAATATATCGGTTATGCGTGGGCGATGGTTGTTGTCATTATAG

GCGCCACTATCGGTATCAAGCTGTTTAAGAAATTCACCTCGAAAGCAAGC

The amino acid sequence was:

(SEQ ID NO: 61)
AEGDDP AKAAFNSLQASATEYIGYAW AMVVVIIGAT IGIKLFKKFT
SKAS

The F03 clone contained only a single amino acid mutation in the mNeonGreen-pVIII fusion protein as compared with the parent clone, which was a V to I mutation at position 33 of the pVIII protein. The corresponding codon was GTC in the parent clone, which was ATA in the F03 clone.

XL1-blue cells containing the different phagemids (either the mNG-pVIII wild type/parent fusion protein in the context of the GB113 fusion system described above, i.e. mNGwt, or the F03 clone with the mNG-mutated pVIII sequence, mNGF03) were cultured for 16 hours at 37 deg C. in the absence of glucose to allow expression of the fusion protein. Cells were washed 3× times in PBS. The optical density of the cells was measured, and all samples were adjusted based on the optical density, to an A600 value of 1. A serial dilution with 1:2 steps was prepared.

The results are shown in FIG. 10. Panel 10A shows the comparison of fluorescence intensity measured directly in live XL-1 blue cells expressing the original Fluorophage (mNGwt) with the lead candidate from the screening (mNGF03). Panel 10B shows the same comparison by monitoring the fluorescence intensity of phage particles which had been packaged in the strains following the standard protocol using Deltaphage as described above. Sample concentrations were determined by infectious titration and all samples were normalized to $5.0\mathrm{e}+12$ $\mathrm{CFU}^{AMP}$/mL. Fluorescence measurement was done in the Varioskan LUX at 488ex/517em.

It can be seen that the F03 clone shows increased bacterial and phage particle fluorescence which is approximately 2 fold higher than the fluorescence seen with the parent clone.

The mNGF03-pVIII fusion cassette was cloned into the phOx-pIX fusion system as described above to form a dual expression construct. Bacterial cells expressing both the phOx-mNGwt as described above and the phOx-mNGF03 were assessed for fluorescence intensity (FIG. 11A), as were phage particles (FIG. 11B).

In FIG. 11A cells were taken during the packaging process. The fluorescence from the starting cultures (containing glucose) was measured to establish the baseline for the fluorescence measurement (Glu). The fluorescence of the same cells was measured after overnight packaging (absence of glucose). All samples were normalized based on the optical density, to an A600 value of 1. A serial dilution in 1:2 steps was prepared. In FIG. 11B the phage concentration was determined based on the DNA amount present in the sample. Raw data was adjusted to the lowest value, 4.18E+12.

It can be seen from FIGS. 11A and B that in the phOx system the mNGwt produces good fluorescence as measured on both bacterial cells (FIG. 11A) and phage particles (FIG. 11B). FIGS. 11A and B show that the mNGF03 also produces fluorescence in the phOx system. FIG. 11B also shows that, once adjusted for titre, the phOx-mNGF03 phage show a better fluorescence signal per phage than the mNGwt.

A further dual display vector was constructed in which the H57 anti-mouse TCR scFv was fused to pIX.

Construction of the pGALD9FN

The H57 anti-mouse TCR scFv antibody sequence, as described by Huppa et al, 2010 (Nature 463:963-7) fused to pIX was generated by gene synthesis (GS) and standard molecular cloning into the pGALD9ΔLFN phagemid on the compatible NcoI/NotI RE sites (Huppa et al. 2010, supra; Løset et al. 2011, PLosONE, 6: e17433 supra) was carried out. The GS, cloning procedure and confirmation by sequencing was performed by Eurofins.

Construction of the H57-mNGF03

The cassette containing the complete mNGF03-pVIII cassette was sub-cloned into the pGALD9ΔLFN-H57 phagemid using the flanking NheI. The correct orientation was confirmed by sequencing by Eurofins.

Construction of Retroviral Vector for TCR Expression

A gene containing the Vα and Vβ of the R12-C9 TCR (Straetemans, T., et al., 2012) grafted onto murine Cα and Cβ, respectively, with alpha and beta coupled by P2A cleavable peptide (Eurofins Genomics) were cloned into pMSCV-Neo (Clontech) with a re-organized MCS on EcoRI and XhoI restriction sites essentially as described (Hoist, J. et al. Generation of T-cell receptor retrogenic mice. *Nat. Protocols* 1, 406-417 (2006).

Construction of SKW-3 R12-C9 Cell Line

GP2-293 cells (Clontech) were co-transfected with pMSCV-Neo R12-09 and pEco (Clontech). Viral supernatant was transduced into SKW-3 cells (CLS Cell Line Services, Germany). A transduced pool of SKW-3 R12-C9 cells were co-stained with PE α-hCD3 mAb (BD Biosciences) and mCβ specific H57-A647 mAb (LifeTech) and positive transductants were isolated on a FACSAria Hu (BD).

Flow Cytometry

Aliquots of $5 \times 10^4$ SKW-3 R12-C9 TCR transfectant and untransfected SKW-3 cells (negative control) were distributed into a V-shaped 96-well dish (Costar). The total volumes were adjusted to 250 µl/well with 0.5% w/v BSA/PBS (pH 7.4). The plate was centrifuged at 300 g/5 min at RT and the supernatants discarded. Aliquots of 25 µl/well of phages with normalized titers of $5 \times 10^{12}$ cfu$^{ampR}$/ml pre-blocked in 0.5% BSA/PBS were added (Control wells received 0.5% BSA/PBS only) and the plate incubated for 30 min at RT. The cells were washed by adding 200 µl/well with 0.5% BSA/PBS, the cells pelleted by centrifuged at 300 g/5 min/RT and the supernatants discarded. APC-conjugated chicken Anti-fd (Norwegian Antibodies) in 0.5% BSA/PBS was added to the appropriate wells, followed by a 30 min incubation at 4° C. The wells were washed twice as above and immediately analysed on an Accuri C6 (BD Biosciences). Data analysis was done using the FlowJo (v10.5) software.

Detection of Cell Surface Expressed Proteins by Flow Cytometry

A powerful application of the Fluorophage would be to use it in real time selection on FACS without the need for staining antibodies, but only relying on the inherent fluorescence of the fluorophore-pVIII fusion for detection. To assess this, we tested the H57 scFv-pIX displaying Fluorophage for specific binding to the T-cell receptor expressed on human SKW-3 R12-C9 T cell hybridoma cells using flow cytometry. For comparison, we prepared H57 scFv-pIX displaying phages without the fluorophore-pVIII fusion and tested in parallel.

In order to verify specific binding to the cells expressing the TCR R12-C9 using standard methodology, we used a APC-conjugated anti-fd antibody to detect bound phages. This also allowed a side-by-side comparison of the Fluorophage and the regular phage bound to the TCR (FIG. 12A), and neither bound to the TCR negative human SKW-3 (FIG. 12B). When attempting to stain cells without the addition of a detection mAb, we observed no increase in fluorescence intensity compared to the controls (FIG. 12C), despite the strong fluorescence signal observed from the Fluorophage scFv H57 when in solution (H57-mNGF03, FIG. 12D). Thus, even though the Fluorophage exhibited strong fluorescent signal in solution, we were unable to detect it in binding to surface bound antigen using flow cytometry. This means that although this Fluorophage is highly useful and advantageous in many assays, e.g. FLISA as described below which shares many similarities and components with a FACS assay, the Fluorophage in this form does not yet reach the brightness per particle needed to allow direct staining and FACS sorting of cells.

EXAMPLE 4—ENZYME-LINKED IMMUNOSORBENT ASSAY (ELISA) AND FLUORESCENT-LINKED IMMUNOSORBENT ASSAY (FLISA)

Materials and Methods

Construction of TAT-ABC Expression Vectors

The vectors containing the Tat AC/B genes were designed using the Gensmart design tool (Genscript Ltd.). All constructs were produced and quality controlled by Genscript Ltd. The TatB sequence source is NC_000913.3: 4022218-4022733 (NCBI) and the TatAC sequence source is #X73888.1 (European Nucleotide Archive). For detection purposes TatB was fused to an C-terminal 6×HIS tag and TatC to an C-terminal FLAG tag.

Construction of TaT-AC/B Over Expressing XL1-Blue Cells Containing the phOx-mNGF03 Phagemid Electrocompetent XL1-blue cells were transformed with 1 ng of each vector using the standard protocol for the ECM399 Electroporation System. XL1-blue cells were grown an LB-agar containing 30 µg/mL Chloramphenicol and 50 µg/mL Zeocin to select cells with both expression vectors. Expression of TatC and TatB were confirmed by standard Western Blot analysis using horse radish peroxidase conjugated anti-FLAG-M2 (1:5000 dilution) and anti-HIS (1:2000 dilution) mAB on lysates from double positive clones. 3 cell clones were chosen based on their expression levels. 10 mL from all three cell clones were transduced with phages carrying a phagemid containing the phOx-pIX and the mNeonGreen-F03-pVIII fusion. 10 µl culture were incubated on LB-agar containing 30 µg/mL Chloramphenicol, 50 µg/mL Zeocin, 500 mM glucose and 100 µg/mL Ampicillin. Resulting clones were tested based on their ability to fluoresce.

In this Example, in some experiments XL-1 host cells were used which had been engineered to overexpress the Tat transporter as described above, as well as expressing the phOx-mNGF03 phagemid in order to see if fluorescence levels could be improved by overexpressing the Tat transporter.

Some exemplary results are shown in FIG. 14, in which an overnight culture of bacterial cells in the absence of glucose shows a high increase in the fluorescence intensity of bacterial cells containing the phOx-mNGF03 phagemid when the Tat transporter is overexpressed (XL1-blue TAT; phOx-mNGF03) as compared to bacterial cells with no Tat transporter overexpression (XL1-blue; phOx-mNGF03).

In addition, to assess whether or not we could combine the ability to display both a functional fluorophore-pVIII fusion and a different functional fusion on a different capsid than pVIII on the same phage particle, we chose to insert a well-described anti-phOx scFv (Marks et al., 1992, Biotechnology, 10:779-783) into the fluorophore-pVIII expressing phagemid as a pIX fusion (this anti-phOX phagemid was also used in some experiments above). We then prepared phages and tested them for phOx binding in classical ELISA as well as FLISA as described. For comparison, we prepared anti-phox scFv-pIX displaying phages without the fluorophore-pVIII fusion and tested in parallel.

The fluorescence intensity of normalized amounts of phage particles was measured in the Varioskan LUX plate reader (FIG. 13D) and showed very high fluorescence intensity, and only from the phages displaying the fluorophore-pVIII fusion. Again when assessed on the phage particles the F03 clone shows improved fluorescence per phage particle when compared to the parent (wt) clone.

Importantly, when testing the same phage samples for scFv target binding in standard ELISA, specific binding was observed independent of presence or absence of the fluorophore-pVIII fusion (FIG. 13C). Thus, the data demonstrate that display of a fluorophore on pVIII did not affect antigen binding mediated by the targeting moiety in the pIX fusion on dual display phage. When the same phage samples again were tested for target binding using FLISA employing the Varioskan LUX plate reader, we could observe fluorescent signal from phage particles that were displaying the mNGwt-pVIII (FIG. 13A, phOx-mNGwt) and the mNGF03-pVIII fusion protein (FIG. 13B), in particular when a high titre of the Tat overexpressing XL-1 bacterial host cells were used (TAT high). Thus, the data show that the intrinsic fluorescence of these phage particles is high enough to provide a sensitivity to specifically detect the reduced amount of phages retained on target after washing in the FLISA and that these phage particles find advantageous utility in such assays, for example enable detection when bound to antigen. Importantly, the data irrevocably shows that dual display of the fluorophore-pVIII fusion and scFv-pIX fusion on the same phage particle does not affect the phenotype of the scFv-pIX fusion.

The invention claimed is:

1. A vector construct comprising:
   (i) a polynucleotide sequence encoding a signal peptide which directs proteins into the Tat secretory pathway; and
   (ii) a polynucleotide sequence encoding a fluorophore fused to a polynucleotide sequence encoding a pVIII phage coat protein.

2. The vector construct of claim 1, wherein the fluorophore is a fluorophore having or comprising a β-barrel structure or architecture.

3. The vector construct of claim 2, wherein the fluorophore is green fluorescent protein (GFP), a GFP-derivative, or has GFP architecture.

4. The vector construct of claim 3, wherein the fluorophore is mNeonGreen comprising SEQ ID NO:4 or a variant sequence thereof having at least 70% identity to SEQ ID NO:4.

5. The vector construct of claim 1, wherein the signal peptide is TorA comprising SEQ ID NO:32 or a variant sequence thereof having at least 70% identity to SEQ ID NO:32.

6. The vector construct of claim 1, wherein the signal peptide is Tor AB7 comprising SEQ ID NO:2 or a variant sequence thereof having at least 70% identity to SEQ ID NO:2.

7. The vector construct of claim 1, wherein the pVIII phage coat protein corresponds to the pVIII coat protein from M13, fd or f1 phage or a variant thereof.

8. The vector construct of claim 1, wherein the pVIII phage coat protein comprises SEQ ID NO:8, or a variant sequence thereof having at least 70% identity to SEQ ID NO:8.

9. The vector construct of claim 8, wherein the variant sequence has a valine to isoleucine mutation at position 33 of SEQ ID NO:8 or a corresponding position.

10. The vector construct of claim 9, wherein the nucleic acid sequence encoding said isoleucine residue comprises the codon ATA.

11. The vector construct of claim 9, wherein the pVIII phage coat protein comprises SEQ ID NO:61, or a variant sequence thereof having at least 70% identity to SEQ ID NO:61, or is encoded by a nucleic acid sequence comprising SEQ ID NO:60 or a variant sequence thereof having at least 70% identity to SEQ ID NO:60.

12. The vector construct of claim 1, wherein the pVIII phage coat protein comprises SEQ ID NO:25, or a variant sequence thereof having at least 70% identity to SEQ ID NO:25.

13. The vector construct of claim 1, wherein the vector further comprises a polynucleotide sequence encoding a linker between the fluorophore and the pVIII phage coat protein.

14. The vector construct of claim 13, wherein the linker comprises SEQ ID NO:6 or a variant sequence thereof having at least 70% identity to SEQ ID NO:6.

15. The vector construct of claim 1, wherein the vector further comprises a polynucleotide sequence encoding a detectable tag.

16. The vector construct of claim 15, wherein the tag is located between the signal peptide and the fluorophore.

17. The vector construct of claim 15, wherein the tag is a FLAG tag or a derivative thereof, or another negatively charged tag.

18. The vector construct of claim 1, wherein the vector further comprises one or more ribosome binding sites (RBS).

19. The vector construct of claim 18, wherein the RBS driving translation of the fluorophore-pVIII fusion protein is a weak RBS.

20. The vector construct of claim 1, wherein the vector construct encodes a polypeptide sequence comprising SEQ ID NO:16: or a variant sequence thereof having at least 70% identity to SEQ ID NO:16.

21. The vector construct of claim 1, wherein the vector construct encodes a polypeptide sequence comprising: (i) SEQ ID NO:18 or a variant sequence thereof having at least 70% identity to SEQ ID NO:18; (ii) SEQ ID NO:20 or a variant sequence thereof having at least 70% identity to SEQ ID NO:20; or (iii) SEQ ID NO:22 or a variant sequence thereof having at least 70% identity to SEQ ID NO:22.

22. The vector construct of claim 21, wherein the pVIII phage coat protein comprises a variant sequence having a valine to isoleucine mutation at the position corresponding to position 33 of SEQ ID NO:8.

23. The vector construct of claim 22, wherein the nucleic acid sequence encoding said isoleucine residue comprises the codon ATA.

24. The vector construct of claim 1, wherein the vector construct further comprises a polynucleotide sequence encoding a protein of interest fused to a polynucleotide sequence encoding a non-pVIII phage coat protein.

25. The vector construct of claim 1, wherein the vector is a phagemid or a phage vector.

26. A nucleic acid molecule comprising a sequence encoding the pVIII phage coat protein variant sequence as defined in claim 9.

27. Phage particles comprising the vector construct of claim 1 and expressing a fluorophore-pVIII fusion protein on the surface.

28. The phage particles of claim 27, wherein said phage particles are particles of a filamentous phage.

29. A library of phage particles, wherein the phage particles are as defined in claim 27, and wherein multiple different proteins of interest are expressed on the surface of the phage particles.

30. A phage display system comprising a vector construct as defined in claim 1.

31. The phage display system of claim 30, further comprising an *E. coli* host cell which over expresses the proteins Tat A, Tat B and Tat C.

32. A method for producing fluorescent phage particles comprising:
   introducing the vector construct as defined in claim 1 into a bacterial host cell.

33. The method according to claim 32, wherein the bacterial host cell is an *E. coli* host cell.

34. The method according to claim 33, wherein the *E. coli* host cell over expresses the proteins Tat A, Tat B and Tat C.

* * * * *

SEQUENCE LISTING

<160> NUMBER OF SEQ ID NOS: 61

<210> SEQ ID NO 1
<211> LENGTH: 114
<212> TYPE: DNA
<213> ORGANISM: Artificial Sequence
<220> FEATURE:
<223> OTHER INFORMATION: Synthesized

<400> SEQUENCE: 1

```
atgaacaata acgatctctt tcagacatca cgtcagcgtt ttttggcaca actcggcggc      60
ttaaccgtcg ccgggatgct ggggccgtca ttgttaacgc cgcgacgtgc gact          114
```

<210> SEQ ID NO 2
<211> LENGTH: 38
<212> TYPE: PRT
<213> ORGANISM: Artificial Sequence
<220> FEATURE:
<223> OTHER INFORMATION: Synthesized

<400> SEQUENCE: 2

```
Met Asn Asn Asn Asp Leu Phe Gln Thr Ser Arg Gln Arg Phe Leu Ala
1               5                   10                  15

Gln Leu Gly Gly Leu Thr Val Ala Gly Met Leu Gly Pro Ser Leu Leu
            20                  25                  30

Thr Pro Arg Arg Ala Thr
        35
```

<210> SEQ ID NO 3
<211> LENGTH: 705
<212> TYPE: DNA
<213> ORGANISM: Artificial Sequence
<220> FEATURE:
<223> OTHER INFORMATION: Synthesized

<400> SEQUENCE: 3

```
gtttctaaag gtgaagaaga caacatggct tctctgccgg ctacccacga actgcacatc      60
ttcggttcta tcaacggtgt tgacttcgac atggttggtc agggtaccgg taacccgaac     120
gacggttacg aagaactgaa cctgaaatct accaaaggtg acctgcagtt ctctccgtgg     180
atcttagttc cgcacatcgg ttacggtttc caccagtacc tgccgtaccc ggacggtatg     240
```

-continued

```
tctccgttcc aggctgctat ggttgacggt tctggttacc aggttcaccg taccatgcag      300
ttcgaagacg gtgcttctct gaccgttaac taccgttaca cctacgaagg ttctcacatc      360
aaaggtgaag ctcaggttaa aggtaccggt ttcccggctg acggtccggt tatgaccaac      420
tctctgaccg ctgctgactg gtgccgttct aaaaaaacct acccgaacga caaaaccatc      480
atctctacct tcaaatggtc ttacaccacc ggtaacggta aacgttaccg ttctaccgct      540
cgtaccacct cacccttcgc taaaccgatg gctgctaact acctgaaaaa ccagccgatg      600
tacgttttcc gtaaaaccga actgaaacac tctaaaaccg aactgaactt caagaatgg       660 cagaaagctt tcaccgacgt tatgggtatg gacgaactgt acaaa                      705
```

```
<210> SEQ ID NO 4
<211> LENGTH: 235
<212> TYPE: PRT
<213> ORGANISM: Artificial Sequence
<220> FEATURE:
<223> OTHER INFORMATION: Synthesized

<400> SEQUENCE: 4
```

Val Ser Lys Gly Glu Glu Asp Asn Met Ala Ser Leu Pro Ala Thr His
1               5                   10                  15

Glu Leu His Ile Phe Gly Ser Ile Asn Gly Val Asp Phe Asp Met Val
            20                  25                  30

Gly Gln Gly Thr Gly Asn Pro Asn Asp Gly Tyr Glu Glu Leu Asn Leu
        35                  40                  45

Lys Ser Thr Lys Gly Asp Leu Gln Phe Ser Pro Trp Ile Leu Val Pro
    50                  55                  60

His Ile Gly Tyr Gly Phe His Gln Tyr Leu Pro Tyr Pro Asp Gly Met
65                  70                  75                  80

Ser Pro Phe Gln Ala Ala Met Val Asp Gly Ser Gly Tyr Gln Val His
                85                  90                  95

Arg Thr Met Gln Phe Glu Asp Gly Ala Ser Leu Thr Val Asn Tyr Arg
            100                 105                 110

Tyr Thr Tyr Glu Gly Ser His Ile Lys Gly Glu Ala Gln Val Lys Gly
        115                 120                 125

Thr Gly Phe Pro Ala Asp Gly Pro Val Met Thr Asn Ser Leu Thr Ala
    130                 135                 140

Ala Asp Trp Cys Arg Ser Lys Lys Thr Tyr Pro Asn Asp Lys Thr Ile
145                 150                 155                 160

Ile Ser Thr Phe Lys Trp Ser Tyr Thr Thr Gly Asn Gly Lys Arg Tyr
                165                 170                 175

Arg Ser Thr Ala Arg Thr Thr Tyr Thr Phe Ala Lys Pro Met Ala Ala
            180                 185                 190

Asn Tyr Leu Lys Asn Gln Pro Met Tyr Val Phe Arg Lys Thr Glu Leu
        195                 200                 205

Lys His Ser Lys Thr Glu Leu Asn Phe Lys Glu Trp Gln Lys Ala Phe
    210                 215                 220

Thr Asp Val Met Gly Met Asp Glu Leu Tyr Lys
225                 230                 235

```
<210> SEQ ID NO 5
<211> LENGTH: 24
<212> TYPE: DNA
<213> ORGANISM: Artificial Sequence
<220> FEATURE:
<223> OTHER INFORMATION: Synthesized
```

```
<400> SEQUENCE: 5
ggcggtggca gcggcggtgg cagc                                              24

<210> SEQ ID NO 6
<211> LENGTH: 8
<212> TYPE: PRT
<213> ORGANISM: Artificial Sequence
<220> FEATURE:
<223> OTHER INFORMATION: Synthesized

<400> SEQUENCE: 6

Gly Gly Gly Ser Gly Gly Gly Ser
1               5

<210> SEQ ID NO 7
<211> LENGTH: 150
<212> TYPE: DNA
<213> ORGANISM: Artificial Sequence
<220> FEATURE:
<223> OTHER INFORMATION: Synthesized

<400> SEQUENCE: 7
gctgagggtg acgatcccgc aaaagcggcc tttaactccc tgcaagcctc agcgaccgaa       60
tatatcggtt atgcgtgggc gatggttgtt gtcattgtcg gcgcaactat cggtatcaag      120
ctgtttaaga aattcaccct cgaaagcaagc                                      150

<210> SEQ ID NO 8
<211> LENGTH: 50
<212> TYPE: PRT
<213> ORGANISM: Artificial Sequence
<220> FEATURE:
<223> OTHER INFORMATION: Synthesized

<400> SEQUENCE: 8

Ala Glu Gly Asp Asp Pro Ala Lys Ala Ala Phe Asn Ser Leu Gln Ala
1               5                   10                  15

Ser Ala Thr Glu Tyr Ile Gly Tyr Ala Trp Ala Met Val Val Val Ile
            20                  25                  30

Val Gly Ala Thr Ile Gly Ile Lys Leu Phe Lys Lys Phe Thr Ser Lys
        35                  40                  45

Ala Ser
    50

<210> SEQ ID NO 9
<211> LENGTH: 24
<212> TYPE: DNA
<213> ORGANISM: Artificial Sequence
<220> FEATURE:
<223> OTHER INFORMATION: Synthesized

<400> SEQUENCE: 9
gattacaagg atgacgatga caag                                              24

<210> SEQ ID NO 10
<211> LENGTH: 8
<212> TYPE: PRT
<213> ORGANISM: Artificial Sequence
<220> FEATURE:
<223> OTHER INFORMATION: Synthesized

<400> SEQUENCE: 10

Asp Tyr Lys Asp Asp Asp Asp Lys
```

<210> SEQ ID NO 11
<211> LENGTH: 1221
<212> TYPE: DNA
<213> ORGANISM: Artificial Sequence
<220> FEATURE:
<223> OTHER INFORMATION: Synthesized

<400> SEQUENCE: 11

```
gctgaaactg ttgaaagttg tttagcaaaa ccccatacag aaaattcatt tactaacgtc      60
tggaaagacg acaaaacttt agatcgttac gctaactatg agggctgtct gtggaatgct     120
acaggcgttg tagtttgtac tggtgacgaa actcagtgtt acggtacatg ggttcctatt     180
gggcttgcta tccctgaaaa tgagggtggt ggctctgagg gtggcggttc tgagggtggc     240
ggttctgagg gtggcggtac taaacctcct gagtacggtg atacacctat tccgggctat     300
acttatatca accctctcga cggcacttat ccgcctggta ctgagcaaaa ccccgctaat     360
cctaatcctt ctcttgagga gtctcagcct cttaatactt tcatgtttca gaataatagg     420
ttccgaaata ggcaggggc attaactgtt tatacgggca ctgttactca aggcactgac     480
cccgttaaaa cttattacca gtacactcct gtatcatcaa aagccatgta tgacgcttac     540
tggaacggta aattcagaga ctgcgctttc cattctggct ttaatgagga tccattcgtt     600
tgtgaatatc aaggccaatc gtctgacctg cctcaacctc ctgtcaatgc tggcggcggc     660
tctggtggtg gttctggtgg cggctctgag ggtggtggct ctgagggtgg cggttctgag     720
ggtggcggct ctgagggagg cggttccggt ggtggctctg gttccggtga ttttgattat     780
gaaaagatgg caaacgctaa taagggggct atgaccgaaa atgccgatga aaacgcgcta     840
cagtctgacg ctaaaggcaa acttgattct gtcgctactg attacggtgc tgctatcgat     900
ggtttcattg gtgacgtttc cggccttgct aatggtaatg gtgctactgg tgattttgct     960
ggctctaatt cccaaatggc tcaagtcggt gacggtgata attcaccttt aatgaataat    1020
ttccgtcaat atttaccttc cctccctcaa tcggttgaat gtcgcccttt tgtctttggc    1080
gctggtaaac catatgaatt ttctattgat tgtgacaaaa taaacttatt ccgtggtgtc    1140
tttgcgtttc ttttatatgt tgccaccttt atgtatgtat tttctacgtt tgctaacata    1200
ctgcgtaata aggagtctta a                                              1221
```

<210> SEQ ID NO 12
<211> LENGTH: 406
<212> TYPE: PRT
<213> ORGANISM: Artificial Sequence
<220> FEATURE:
<223> OTHER INFORMATION: Synthesized

<400> SEQUENCE: 12

```
Ala Glu Thr Val Glu Ser Cys Leu Ala Lys Pro His Thr Glu Asn Ser
1               5                   10                  15

Phe Thr Asn Val Trp Lys Asp Asp Lys Thr Leu Asp Arg Tyr Ala Asn
            20                  25                  30

Tyr Glu Gly Cys Leu Trp Asn Ala Thr Gly Val Val Val Cys Thr Gly
        35                  40                  45

Asp Glu Thr Gln Cys Tyr Gly Thr Trp Val Pro Ile Gly Leu Ala Ile
    50                  55                  60

Pro Glu Asn Glu Gly Gly Gly Ser Glu Gly Gly Gly Ser Glu Gly Gly
65                  70                  75                  80
```

```
Gly Ser Glu Gly Gly Gly Thr Lys Pro Pro Glu Tyr Gly Asp Thr Pro
                85                  90                  95
Ile Pro Gly Tyr Thr Tyr Ile Asn Pro Leu Asp Gly Thr Tyr Pro Pro
            100                 105                 110
Gly Thr Glu Gln Asn Pro Ala Asn Pro Asn Pro Ser Leu Glu Glu Ser
        115                 120                 125
Gln Pro Leu Asn Thr Phe Met Phe Gln Asn Asn Arg Phe Arg Asn Arg
    130                 135                 140
Gln Gly Ala Leu Thr Val Tyr Thr Gly Thr Val Thr Gln Gly Thr Asp
145                 150                 155                 160
Pro Val Lys Thr Tyr Tyr Gln Tyr Thr Pro Val Ser Ser Lys Ala Met
                165                 170                 175
Tyr Asp Ala Tyr Trp Asn Gly Lys Phe Arg Asp Cys Ala Phe His Ser
            180                 185                 190
Gly Phe Asn Glu Asp Pro Phe Val Cys Glu Tyr Gln Gly Gln Ser Ser
        195                 200                 205
Asp Leu Pro Gln Pro Pro Val Asn Ala Gly Gly Ser Gly Gly Gly Gly
    210                 215                 220
Ser Gly Gly Gly Ser Glu Gly Gly Ser Glu Gly Gly Ser Glu
225                 230                 235                 240
Gly Gly Gly Ser Glu Gly Gly Ser Gly Gly Ser Gly Ser Gly
                245                 250                 255
Asp Phe Asp Tyr Glu Lys Met Ala Asn Ala Asn Lys Gly Ala Met Thr
            260                 265                 270
Glu Asn Ala Asp Glu Asn Ala Leu Gln Ser Asp Ala Lys Gly Lys Leu
        275                 280                 285
Asp Ser Val Ala Thr Asp Tyr Gly Ala Ala Ile Asp Gly Phe Ile Gly
    290                 295                 300
Asp Val Ser Gly Leu Ala Asn Gly Asn Gly Ala Thr Gly Asp Phe Ala
305                 310                 315                 320
Gly Ser Asn Ser Gln Met Ala Gln Val Gly Asp Gly Asp Asn Ser Pro
                325                 330                 335
Leu Met Asn Asn Phe Arg Gln Tyr Leu Pro Ser Leu Pro Gln Ser Val
            340                 345                 350
Glu Cys Arg Pro Phe Val Phe Gly Ala Gly Lys Pro Tyr Glu Phe Ser
        355                 360                 365
Ile Asp Cys Asp Lys Ile Asn Leu Phe Arg Gly Val Phe Ala Phe Leu
    370                 375                 380
Leu Tyr Val Ala Thr Phe Met Tyr Val Phe Ser Thr Phe Ala Asn Ile
385                 390                 395                 400
Leu Arg Asn Lys Glu Ser
                405

<210> SEQ ID NO 13
<211> LENGTH: 112
<212> TYPE: PRT
<213> ORGANISM: Artificial Sequence
<220> FEATURE:
<223> OTHER INFORMATION: Synthesized

<400> SEQUENCE: 13

Met Pro Val Leu Leu Gly Ile Pro Leu Leu Leu Arg Phe Leu Gly Phe
1               5                   10                  15
Leu Leu Val Thr Leu Phe Gly Tyr Leu Leu Thr Phe Leu Lys Lys Gly
            20                  25                  30
```

```
Phe Gly Lys Ile Ala Ile Ala Ile Ser Leu Phe Leu Ala Leu Ile Ile
             35                  40                  45

Gly Leu Asn Ser Ile Leu Val Gly Tyr Leu Ser Asp Ile Ser Ala Gln
 50                  55                  60

Leu Pro Ser Asp Phe Val Gln Gly Val Gln Leu Ile Leu Pro Ser Asn
 65                  70                  75                  80

Ala Leu Pro Cys Phe Tyr Val Ile Leu Ser Val Lys Ala Ala Ile Phe
                 85                  90                  95

Ile Phe Asp Val Lys Gln Lys Ile Val Ser Tyr Leu Asp Trp Asp Lys
                100                 105                 110
```

<210> SEQ ID NO 14
<211> LENGTH: 33
<212> TYPE: PRT
<213> ORGANISM: Artificial Sequence
<220> FEATURE:
<223> OTHER INFORMATION: Synthesized

<400> SEQUENCE: 14

```
Met Glu Gln Val Ala Asp Phe Asp Thr Ile Tyr Gln Ala Met Ile Gln
 1               5                  10                  15

Ile Ser Val Val Leu Cys Phe Ala Leu Gly Ile Ala Gly Gly Gln
                 20                  25                  30

Arg
```

<210> SEQ ID NO 15
<211> LENGTH: 32
<212> TYPE: PRT
<213> ORGANISM: Artificial Sequence
<220> FEATURE:
<223> OTHER INFORMATION: Synthesized

<400> SEQUENCE: 15

```
Met Ser Val Leu Val Tyr Ser Phe Ala Ser Phe Val Leu Gly Trp Cys
 1               5                  10                  15

Leu Arg Ser Gly Ile Thr Tyr Phe Thr Arg Leu Met Glu Thr Ser Ser
                 20                  25                  30
```

<210> SEQ ID NO 16
<211> LENGTH: 273
<212> TYPE: PRT
<213> ORGANISM: Artificial Sequence
<220> FEATURE:
<223> OTHER INFORMATION: Synthesized

<400> SEQUENCE: 16

```
Val Ser Lys Gly Glu Glu Asp Asn Met Ala Ser Leu Pro Ala Thr His
 1               5                  10                  15

Glu Leu His Ile Phe Gly Ser Ile Asn Gly Val Asp Phe Asp Met Val
                 20                  25                  30

Gly Gln Gly Thr Gly Asn Pro Asn Asp Gly Tyr Glu Glu Leu Asn Leu
             35                  40                  45

Lys Ser Thr Lys Gly Asp Leu Gln Phe Ser Pro Trp Ile Leu Val Pro
 50                  55                  60

His Ile Gly Tyr Gly Phe His Gln Tyr Leu Pro Tyr Pro Asp Gly Met
 65                  70                  75                  80

Ser Pro Phe Gln Ala Ala Met Val Asp Gly Ser Gly Tyr Gln Val His
                 85                  90                  95

Arg Thr Met Gln Phe Glu Asp Gly Ala Ser Leu Thr Val Asn Tyr Arg
                100                 105                 110
```

```
Tyr Thr Tyr Glu Gly Ser His Ile Lys Gly Glu Ala Gln Val Lys Gly
            115                 120                 125

Thr Gly Phe Pro Ala Asp Gly Pro Val Met Thr Asn Ser Leu Thr Ala
        130                 135                 140

Ala Asp Trp Cys Arg Ser Lys Lys Thr Tyr Pro Asn Asp Lys Thr Ile
145                 150                 155                 160

Ile Ser Thr Phe Lys Trp Ser Tyr Thr Thr Gly Asn Gly Lys Arg Tyr
                165                 170                 175

Arg Ser Thr Ala Arg Thr Thr Tyr Thr Phe Ala Lys Pro Met Ala Ala
            180                 185                 190

Asn Tyr Leu Lys Asn Gln Pro Met Tyr Val Phe Arg Lys Thr Glu Leu
            195                 200                 205

Lys His Ser Lys Thr Glu Leu Asn Phe Lys Glu Trp Gln Lys Ala Phe
        210                 215                 220

Thr Asp Val Met Gly Met Asp Glu Leu Tyr Lys Gly Gly Gly Ser Gly
225                 230                 235                 240

Gly Gly Ser Ala Glu Gly Asp Asp Pro Ala Lys Ala Ala Phe Asn Ser
                245                 250                 255

Leu Gln Ala Ser Ala Thr Glu Tyr Ile Gly Tyr Ala Trp Ala Met Val
            260                 265                 270

Val
```

<210> SEQ ID NO 17
<211> LENGTH: 819
<212> TYPE: DNA
<213> ORGANISM: Artificial Sequence
<220> FEATURE:
<223> OTHER INFORMATION: Synthesized

<400> SEQUENCE: 17

```
gtttctaaag gtgaagaaga caacatggct tctctgccgg ctacccacga actgcacatc    60
ttcggttcta tcaacggtgt tgacttcgac atggttggtc agggtaccgg taacccgaac   120
gacggttacg aagaactgaa cctgaaatct accaaaggtg acctgcagtt ctctccgtgg   180
atcttagttc cgcacatcgg ttacggtttc accagtacc tgccgtaccc ggacggtatg   240
tctccgttcc aggctgctat ggttgacggt tctggttacc aggttcaccg taccatgcag   300
ttcgaagacg gtgcttctct gaccgttaac taccgttaca cctacgaagg ttctcacatc   360
aaaggtgaag ctcaggttaa aggtaccggt ttcccggctg acggtccggt tatgaccaac   420
tctctgaccg ctgctgactg gtgccgttct aaaaaaacct acccgaacga caaaaccatc   480
atctctacct tcaaatggtc ttacaccacc ggtaacggta acgttaccg ttctaccgct   540
cgtaccacct cacccttcgc taaaccgatg gctgctaact acctgaaaaa ccagccgatg   600
tacgttttcc gtaaaaccga actgaaacac tctaaaaccg aactgaactt caaagaatgg   660
cagaaagctt tcaccgacgt tatgggtatg gacgaactgt acaaaggcgg tggcagcggc   720
ggtggcagcg ctgagggtga cgatcccgca aaagcggcct taactcccct gcaagcctca   780
gcgaccgaat atatcggtta tgcgtgggcg atggttgtt                          819
```

<210> SEQ ID NO 18
<211> LENGTH: 293
<212> TYPE: PRT
<213> ORGANISM: Artificial Sequence
<220> FEATURE:
<223> OTHER INFORMATION: Synthesized

<400> SEQUENCE: 18

| | | | | | | | | | | | | | | |
|---|---|---|---|---|---|---|---|---|---|---|---|---|---|---|
|Val|Ser|Lys|Gly|Glu|Glu|Asp|Asn|Met|Ala|Ser|Leu|Pro|Ala|Thr|His|
|1| | | |5| | | | |10| | | | |15| |

Val Ser Lys Gly Glu Glu Asp Asn Met Ala Ser Leu Pro Ala Thr His
1               5                   10                  15

Glu Leu His Ile Phe Gly Ser Ile Asn Gly Val Asp Phe Asp Met Val
            20                  25                  30

Gly Gln Gly Thr Gly Asn Pro Asn Asp Gly Tyr Glu Leu Asn Leu
        35                  40                  45

Lys Ser Thr Lys Gly Asp Leu Gln Phe Ser Pro Trp Ile Leu Val Pro
50                  55                  60

His Ile Gly Tyr Gly Phe His Gln Tyr Leu Pro Tyr Pro Asp Gly Met
65                  70                  75                  80

Ser Pro Phe Gln Ala Ala Met Val Asp Gly Ser Gly Tyr Gln Val His
                85                  90                  95

Arg Thr Met Gln Phe Glu Asp Gly Ala Ser Leu Thr Val Asn Tyr Arg
            100                 105                 110

Tyr Thr Tyr Glu Gly Ser His Ile Lys Gly Glu Ala Gln Val Lys Gly
            115                 120                 125

Thr Gly Phe Pro Ala Asp Gly Pro Val Met Thr Asn Ser Leu Thr Ala
    130                 135                 140

Ala Asp Trp Cys Arg Ser Lys Lys Thr Tyr Pro Asn Asp Lys Thr Ile
145                 150                 155                 160

Ile Ser Thr Phe Lys Trp Ser Tyr Thr Thr Gly Asn Gly Lys Arg Tyr
                165                 170                 175

Arg Ser Thr Ala Arg Thr Thr Tyr Thr Phe Ala Lys Pro Met Ala Ala
            180                 185                 190

Asn Tyr Leu Lys Asn Gln Pro Met Tyr Val Phe Arg Lys Thr Glu Leu
            195                 200                 205

Lys His Ser Lys Thr Glu Leu Asn Phe Lys Glu Trp Gln Lys Ala Phe
            210                 215                 220

Thr Asp Val Met Gly Met Asp Glu Leu Tyr Lys Gly Gly Gly Ser Gly
225                 230                 235                 240

Gly Gly Ser Ala Glu Gly Asp Asp Pro Ala Lys Ala Ala Phe Asn Ser
            245                 250                 255

Leu Gln Ala Ser Ala Thr Glu Tyr Ile Gly Tyr Ala Trp Ala Met Val
            260                 265                 270

Val Val Ile Val Gly Ala Thr Ile Gly Ile Lys Leu Phe Lys Lys Phe
            275                 280                 285

Thr Ser Lys Ala Ser
        290

<210> SEQ ID NO 19
<211> LENGTH: 879
<212> TYPE: DNA
<213> ORGANISM: Artificial Sequence
<220> FEATURE:
<223> OTHER INFORMATION: Synthesized

<400> SEQUENCE: 19

```
gtttctaaag gtgaagaaga caacatggct tctctgccgg ctacccacga actgcacatc      60
ttcggttcta tcaacggtgt tgacttcgac atggttggtc agggtaccgg taacccgaac     120
gacggttacg aagaactgaa cctgaaatct accaaaggtg acctgcagtt ctctccgtgg     180
atcttagttc cgcacatcgg ttacggtttc caccagtacc tgccgtaccc ggacggtatg     240
tctccgttcc aggctgctat ggttgacggt tctggttacc aggttcaccg taccatgcag     300
```

```
ttcgaagacg gtgcttctct gaccgttaac taccgttaca cctacgaagg ttctcacatc    360
aaaggtgaag ctcaggttaa aggtaccggt ttcccggctg acggtccggt tatgaccaac    420
tctctgaccg ctgctgactg gtgccgttct aaaaaaacct acccgaacga caaaaccatc    480
atctctacct tcaaatggtc ttacaccacc ggtaacggta acgttaccg ttctaccgct     540 cgtaccacct acaccttcgc taaaccgatg ctgctaact acctgaaaaa ccagccgatg     600
tacgttttcc gtaaaaccga actgaaacac tctaaaaccg aactgaactt caaagaatgg    660
cagaaagctt tcaccgacgt tatgggtatg gacgaactgt acaaggcgg tggcagcggc     720 ggtggcagcg ctgagggtga cgatcccgca aaagcggcct taactccct gcaagcctca     780 gcgaccgaat atatcggtta tgcgtgggcg atggttgttg tcattgtcgg cgcaactatc    840
ggtatcaagc tgtttaagaa attcacctcg aaagcaagc                          879
```

<210> SEQ ID NO 20
<211> LENGTH: 334
<212> TYPE: PRT
<213> ORGANISM: Artificial Sequence
<220> FEATURE:
<223> OTHER INFORMATION: Synthesized

<400> SEQUENCE: 20

```
Met Asn Asn Asn Asp Leu Phe Gln Thr Ser Arg Gln Arg Phe Leu Ala
1               5                   10                  15

Gln Leu Gly Gly Leu Thr Val Ala Gly Met Leu Gly Pro Ser Leu Leu
            20                  25                  30

Thr Pro Arg Arg Ala Thr Ala Ala Gly Val Ser Lys Gly Glu Glu Asp
        35                  40                  45

Asn Met Ala Ser Leu Pro Ala Thr His Glu Leu His Ile Phe Gly Ser
    50                  55                  60

Ile Asn Gly Val Asp Phe Asp Met Val Gly Gln Gly Thr Gly Asn Pro
65                  70                  75                  80

Asn Asp Gly Tyr Glu Glu Leu Asn Leu Lys Ser Thr Lys Gly Asp Leu
                85                  90                  95

Gln Phe Ser Pro Trp Ile Leu Val Pro His Ile Gly Tyr Gly Phe His
            100                 105                 110

Gln Tyr Leu Pro Tyr Pro Asp Gly Met Ser Pro Phe Gln Ala Ala Met
        115                 120                 125

Val Asp Gly Ser Gly Tyr Gln Val His Arg Thr Met Gln Phe Glu Asp
    130                 135                 140

Gly Ala Ser Leu Thr Val Asn Tyr Arg Tyr Thr Tyr Glu Gly Ser His
145                 150                 155                 160

Ile Lys Gly Glu Ala Gln Val Lys Gly Thr Gly Phe Pro Ala Asp Gly
                165                 170                 175

Pro Val Met Thr Asn Ser Leu Thr Ala Ala Asp Trp Cys Arg Ser Lys
            180                 185                 190

Lys Thr Tyr Pro Asn Asp Lys Thr Ile Ile Ser Thr Phe Lys Trp Ser
        195                 200                 205

Tyr Thr Thr Gly Asn Gly Lys Arg Tyr Arg Ser Thr Ala Arg Thr Thr
    210                 215                 220

Tyr Thr Phe Ala Lys Pro Met Ala Ala Asn Tyr Leu Lys Asn Gln Pro
225                 230                 235                 240

Met Tyr Val Phe Arg Lys Thr Glu Leu Lys His Ser Lys Thr Glu Leu
                245                 250                 255

Asn Phe Lys Glu Trp Gln Lys Ala Phe Thr Asp Val Met Gly Met Asp
```

```
                260                 265                 270
Glu Leu Tyr Lys Gly Gly Gly Ser Gly Gly Ser Ala Glu Gly Asp
            275                 280                 285

Asp Pro Ala Lys Ala Ala Phe Asn Ser Leu Gln Ala Ser Ala Thr Glu
        290                 295                 300

Tyr Ile Gly Tyr Ala Trp Ala Met Val Val Ile Val Gly Ala Thr
305                 310                 315                 320

Ile Gly Ile Lys Leu Phe Lys Lys Phe Thr Ser Lys Ala Ser
                325                 330
```

<210> SEQ ID NO 21
<211> LENGTH: 1002
<212> TYPE: DNA
<213> ORGANISM: Artificial Sequence
<220> FEATURE:
<223> OTHER INFORMATION: Synthesized

<400> SEQUENCE: 21

```
atgaacaata acgatctctt tcagacatca cgtcagcgtt ttttggcaca actcggcggc       60
ttaaccgtcg ccgggatgct ggggccgtca ttgttaacgc cgcgacgtgc gactgcggcg     120
ggcgtttcta aaggtgaaga agacaacatg gcttctctgc cggctaccca cgaactgcac     180
atcttcggtt ctatcaacgg tgttgacttc gacatggttg gtcagggtac cggtaacccg     240
aacgacggtt acgaagaact gaacctgaaa tctaccaaag tgacctgca gttctctccg      300
tggatcttag ttccgcacat cggttacggt tccaccagt acctgccgta cccggacggt      360
atgtctccgt tccaggctgc tatggttgac ggttctggtt accaggttca ccgtaccatg     420
cagttcgaag acggtgcttc tctgaccgtt aactaccgtt acacctacga aggttctcac     480
atcaaaggtg aagctcaggt taaaggtacc ggtttcccgg ctgacggtcc ggttatgacc     540
aactctctga ccgctgctga ctggtgccgt tctaaaaaaa cctacccgaa cgacaaaacc     600
atcatctcta ccttcaaatg gtcttacacc accggtaacg gtaaacgtta ccgttctacc     660
gctcgtacca cctacacctt cgctaaaccg atggctgcta actacctgaa aaaccagccg     720
atgtacgttt tccgtaaaac cgaactgaaa cactctaaaa ccgaactgaa cttcaaagaa     780
tggcagaaag ctttcaccga cgttatgggt atggacgaac tgtacaaagg cggtggcagc     840
ggcggtggca gcgctgaggg tgacgatccc gcaaaagcgg cctttaactc cctgcaagcc     900
tcagcgaccg aatatatcgg ttatgcgtgg gcgatggttg ttgtcattgt cggcgcaact     960
atcggtatca agctgtttaa gaaattcacc tcgaaagcaa gc                        1002
```

<210> SEQ ID NO 22
<211> LENGTH: 342
<212> TYPE: PRT
<213> ORGANISM: Artificial Sequence
<220> FEATURE:
<223> OTHER INFORMATION: Synthesized

<400> SEQUENCE: 22

```
Met Asn Asn Asn Asp Leu Phe Gln Thr Ser Arg Gln Arg Phe Leu Ala
1               5                   10                  15

Gln Leu Gly Gly Leu Thr Val Ala Gly Met Leu Gly Pro Ser Leu Leu
            20                  25                  30

Thr Pro Arg Arg Ala Thr Ala Ala Asp Tyr Lys Asp Asp Asp Asp Lys
        35                  40                  45

Gly Val Ser Lys Gly Glu Glu Asp Asn Met Ala Ser Leu Pro Ala Thr
    50                  55                  60
```

His Glu Leu His Ile Phe Gly Ser Ile Asn Gly Val Asp Phe Asp Met
 65                  70                  75                  80

Val Gly Gln Gly Thr Gly Asn Pro Asn Asp Gly Tyr Glu Glu Leu Asn
             85                  90                  95

Leu Lys Ser Thr Lys Gly Asp Leu Gln Phe Ser Pro Trp Ile Leu Val
            100                 105                 110

Pro His Ile Gly Tyr Gly Phe His Gln Tyr Leu Pro Tyr Pro Asp Gly
            115                 120                 125

Met Ser Pro Phe Gln Ala Ala Met Val Asp Gly Ser Gly Tyr Gln Val
130                 135                 140

His Arg Thr Met Gln Phe Glu Asp Gly Ala Ser Leu Thr Val Asn Tyr
145                 150                 155                 160

Arg Tyr Thr Tyr Glu Gly Ser His Ile Lys Gly Glu Ala Gln Val Lys
                165                 170                 175

Gly Thr Gly Phe Pro Ala Asp Gly Pro Val Met Thr Asn Ser Leu Thr
            180                 185                 190

Ala Ala Asp Trp Cys Arg Ser Lys Lys Thr Tyr Pro Asn Asp Lys Thr
            195                 200                 205

Ile Ile Ser Thr Phe Lys Trp Ser Tyr Thr Thr Gly Asn Gly Lys Arg
210                 215                 220

Tyr Arg Ser Thr Ala Arg Thr Thr Tyr Thr Phe Ala Lys Pro Met Ala
225                 230                 235                 240

Ala Asn Tyr Leu Lys Asn Gln Pro Met Tyr Val Phe Arg Lys Thr Glu
                245                 250                 255

Leu Lys His Ser Lys Thr Glu Leu Asn Phe Lys Glu Trp Gln Lys Ala
            260                 265                 270

Phe Thr Asp Val Met Gly Met Asp Glu Leu Tyr Lys Gly Gly Gly Ser
            275                 280                 285

Gly Gly Gly Ser Ala Glu Gly Asp Asp Pro Ala Lys Ala Ala Phe Asn
290                 295                 300

Ser Leu Gln Ala Ser Ala Thr Glu Tyr Ile Gly Tyr Ala Trp Ala Met
305                 310                 315                 320

Val Val Val Ile Val Gly Ala Thr Ile Gly Ile Lys Leu Phe Lys Lys
                325                 330                 335

Phe Thr Ser Lys Ala Ser
            340

<210> SEQ ID NO 23
<211> LENGTH: 1026
<212> TYPE: DNA
<213> ORGANISM: Artificial Sequence
<220> FEATURE:
<223> OTHER INFORMATION: Synthesized

<400> SEQUENCE: 23
atgaacaata acgatctctt tcagacatca cgtcagcgtt ttttggcaca actcggcggc    60
ttaaccgtcg ccgggatgct ggggccgtca ttgttaacgc cgcgacgtgc gactgcggcg   120
gattacaagg atgacgatga caagggcgtt tctaaaggtg aagaagacaa catggcttct   180
ctgccggcta cccacgaact gcacatcttc ggttctatca acggtgttga cttcgacatg   240
gttggtcagg gtaccggtaa cccgaacgac ggttacgaag aactgaacct gaaatctacc   300
aaaggtgacc tgcagttctc tccgtggatc ttagttccgc acatcggtta cggtttccac   360
cagtacctgc cgtacccgga cggtatgtct ccgttccagg ctgctatggt tgacggttct   420

```
ggttaccagg ttcaccgtac catgcagttc gaagacggtg cttctctgac cgttaactac    480
cgttacacct acgaaggttc tcacatcaaa ggtgaagctc aggttaaagg taccggtttc    540
ccggctgacg gtccggttat gaccaactct ctgaccgctg ctgactggtg ccgttctaaa    600
aaaacctacc cgaacgacaa aaccatcatc tctaccttca atggtctta caccaccggt    660 aacggtaaac gttaccgttc taccgctcgt accacctaca ccttcgctaa accgatggct    720
gctaactacc tgaaaaacca gccgatgtac gttttccgta aaaccgaact gaaacactct    780
aaaaccgaac tgaacttcaa agaatggcag aaagctttca ccgacgttat gggtatggac    840
gaactgtaca aggcggtgg cagcggcggt ggcagcgctg agggtgacga tcccgcaaaa    900 gcggcccttta actccctgca agcctcagcg accgaatata tcggttatgc gtgggcgatg    960
gttgttgtca ttgtcggcgc aactatcggt atcaagctgt ttaagaaatt caccctcgaaa   1020 gcaagc                                                               1026
```

<210> SEQ ID NO 24
<211> LENGTH: 90
<212> TYPE: DNA
<213> ORGANISM: Artificial Sequence
<220> FEATURE:
<223> OTHER INFORMATION: Synthesized

<400> SEQUENCE: 24

```
gctgagggtg acgatcccgc aaaagcggcc tttaactccc tgcaagcctc agcgaccgaa     60
tatatcggtt atgcgtgggc gatggttgtt                                      90
```

<210> SEQ ID NO 25
<211> LENGTH: 30
<212> TYPE: PRT
<213> ORGANISM: Artificial Sequence
<220> FEATURE:
<223> OTHER INFORMATION: Synthesized

<400> SEQUENCE: 25

```
Ala Glu Gly Asp Asp Pro Ala Lys Ala Ala Phe Asn Ser Leu Gln Ala
1               5                   10                  15

Ser Ala Thr Glu Tyr Ile Gly Tyr Ala Trp Ala Met Val Val
            20                  25                  30
```

<210> SEQ ID NO 26
<211> LENGTH: 314
<212> TYPE: PRT
<213> ORGANISM: Artificial Sequence
<220> FEATURE:
<223> OTHER INFORMATION: Synthesized

<400> SEQUENCE: 26

```
Met Asn Asn Asn Asp Leu Phe Gln Thr Ser Arg Gln Arg Phe Leu Ala
1               5                   10                  15

Gln Leu Gly Gly Leu Thr Val Ala Gly Met Leu Gly Pro Ser Leu Leu
            20                  25                  30

Thr Pro Arg Arg Ala Thr Ala Ala Gly Val Ser Lys Gly Glu Glu Asp
        35                  40                  45

Asn Met Ala Ser Leu Pro Ala Thr His Glu Leu His Ile Phe Gly Ser
    50                  55                  60

Ile Asn Gly Val Asp Phe Asp Met Val Gly Gln Gly Thr Gly Asn Pro
65                  70                  75                  80

Asn Asp Gly Tyr Glu Glu Leu Asn Leu Lys Ser Thr Lys Gly Asp Leu
                85                  90                  95
```

```
Gln Phe Ser Pro Trp Ile Leu Val Pro His Ile Gly Tyr Gly Phe His
            100                 105                 110
Gln Tyr Leu Pro Tyr Pro Asp Gly Met Ser Pro Phe Gln Ala Ala Met
        115                 120                 125
Val Asp Gly Ser Gly Tyr Gln Val His Arg Thr Met Gln Phe Glu Asp
    130                 135                 140
Gly Ala Ser Leu Thr Val Asn Tyr Arg Tyr Thr Tyr Glu Gly Ser His
145                 150                 155                 160
Ile Lys Gly Glu Ala Gln Val Lys Gly Thr Gly Phe Pro Ala Asp Gly
                165                 170                 175
Pro Val Met Thr Asn Ser Leu Thr Ala Ala Asp Trp Cys Arg Ser Lys
            180                 185                 190
Lys Thr Tyr Pro Asn Asp Lys Thr Ile Ile Ser Thr Phe Lys Trp Ser
        195                 200                 205
Tyr Thr Thr Gly Asn Gly Lys Arg Tyr Arg Ser Thr Ala Arg Thr Thr
    210                 215                 220
Tyr Thr Phe Ala Lys Pro Met Ala Ala Asn Tyr Leu Lys Asn Gln Pro
225                 230                 235                 240
Met Tyr Val Phe Arg Lys Thr Glu Leu Lys His Ser Lys Thr Glu Leu
                245                 250                 255
Asn Phe Lys Glu Trp Gln Lys Ala Phe Thr Asp Val Met Gly Met Asp
            260                 265                 270
Glu Leu Tyr Lys Gly Gly Gly Ser Gly Gly Ser Ala Glu Gly Asp
        275                 280                 285
Asp Pro Ala Lys Ala Ala Phe Asn Ser Leu Gln Ala Ser Ala Thr Glu
    290                 295                 300
Tyr Ile Gly Tyr Ala Trp Ala Met Val Val
305                 310

<210> SEQ ID NO 27
<211> LENGTH: 942
<212> TYPE: DNA
<213> ORGANISM: Artificial Sequence
<220> FEATURE:
<223> OTHER INFORMATION: Synthesized

<400> SEQUENCE: 27
atgaacaata acgatctctt tcagacatca cgtcagcgtt ttttggcaca actcggcggc      60
ttaaccgtcg ccgggatgct ggggccgtca ttgttaacgc cgcgacgtgc gactgcggcg     120
ggcgtttcta aaggtgaaga agacaacatg gcttctctgc cggctaccca cgaactgcac     180
atcttcggtt ctatcaacgg tgttgacttc gacatggttg gtcagggtac cggtaacccg     240
aacgacggtt acgaagaact gaacctgaaa tctaccaaag gtgacctgca gttctctccg     300
tggatcttag ttccgcacat cggttacggt ttccaccagt acctgccgta cccggacggt     360
atgtctccgt tccaggctgc tatggttgac ggttctggtt accaggttca ccgtaccatg     420
cagttcgaag acggtgcttc tctgaccgtt aactaccgtt acacctacga aggttctcac     480
atcaaaggtg aagctcaggt taaaggtacc ggtttcccgg ctgacggtcc ggttatgacc     540
aactctctga ccgctgctga ctggtgccgt tctaaaaaaa cctacccgaa cgacaaaacc     600
atcatctcta ccttcaaatg gtcttacacc accggtaacg gtaaacgtta ccgttctacc     660
gctcgtacca cctacacctt cgctaaaccg atggctgcta actacctgaa aaaccagccg     720
atgtacgttt tccgtaaaac cgaactgaaa cactctaaaa ccgaactgaa cttcaaagaa     780
```

```
tggcagaaag ctttcaccga cgttatgggt atggacgaac tgtacaaagg cggtggcagc    840
ggcggtggca gcgctgaggg tgacgatccc gcaaaagcgg cctttaactc cctgcaagcc    900
tcagcgaccg aatatatcgg ttatgcgtgg gcgatggttg tt                        942
```

<210> SEQ ID NO 28
<211> LENGTH: 322
<212> TYPE: PRT
<213> ORGANISM: Artificial Sequence
<220> FEATURE:
<223> OTHER INFORMATION: Synthesized

<400> SEQUENCE: 28

```
Met Asn Asn Asn Asp Leu Phe Gln Thr Ser Arg Gln Arg Phe Leu Ala
1               5                   10                  15

Gln Leu Gly Gly Leu Thr Val Ala Gly Met Leu Gly Pro Ser Leu Leu
            20                  25                  30

Thr Pro Arg Arg Ala Thr Ala Ala Asp Tyr Lys Asp Asp Asp Asp Lys
        35                  40                  45

Gly Val Ser Lys Gly Glu Glu Asp Asn Met Ala Ser Leu Pro Ala Thr
    50                  55                  60

His Glu Leu His Ile Phe Gly Ser Ile Asn Gly Val Asp Phe Asp Met
65                  70                  75                  80

Val Gly Gln Gly Thr Gly Asn Pro Asn Asp Gly Tyr Glu Glu Leu Asn
                85                  90                  95

Leu Lys Ser Thr Lys Gly Asp Leu Gln Phe Ser Pro Trp Ile Leu Val
            100                 105                 110

Pro His Ile Gly Tyr Gly Phe His Gln Tyr Leu Pro Tyr Pro Asp Gly
        115                 120                 125

Met Ser Pro Phe Gln Ala Ala Met Val Asp Gly Ser Gly Tyr Gln Val
    130                 135                 140

His Arg Thr Met Gln Phe Glu Asp Gly Ala Ser Leu Thr Val Asn Tyr
145                 150                 155                 160

Arg Tyr Thr Tyr Glu Gly Ser His Ile Lys Gly Glu Ala Gln Val Lys
                165                 170                 175

Gly Thr Gly Phe Pro Ala Asp Gly Pro Val Met Thr Asn Ser Leu Thr
            180                 185                 190

Ala Ala Asp Trp Cys Arg Ser Lys Lys Thr Tyr Pro Asn Asp Lys Thr
        195                 200                 205

Ile Ile Ser Thr Phe Lys Trp Ser Tyr Thr Thr Gly Asn Gly Lys Arg
    210                 215                 220

Tyr Arg Ser Thr Ala Arg Thr Thr Tyr Thr Phe Ala Lys Pro Met Ala
225                 230                 235                 240

Ala Asn Tyr Leu Lys Asn Gln Pro Met Tyr Val Phe Arg Lys Thr Glu
                245                 250                 255

Leu Lys His Ser Lys Thr Glu Leu Asn Phe Lys Glu Trp Gln Lys Ala
            260                 265                 270

Phe Thr Asp Val Met Gly Met Asp Glu Leu Tyr Lys Gly Gly Gly Ser
        275                 280                 285

Gly Gly Gly Ser Ala Glu Gly Asp Asp Pro Ala Lys Ala Ala Phe Asn
    290                 295                 300

Ser Leu Gln Ala Ser Ala Thr Glu Tyr Ile Gly Tyr Ala Trp Ala Met
305                 310                 315                 320

Val Val
```

```
<210> SEQ ID NO 29
<211> LENGTH: 966
<212> TYPE: DNA
<213> ORGANISM: Artificial Sequence
<220> FEATURE:
<223> OTHER INFORMATION: Synthesized

<400> SEQUENCE: 29
atgaacaata acgatctctt tcagacatca cgtcagcgtt ttttggcaca actcggcggc      60
ttaaccgtcg ccgggatgct ggggccgtca ttgttaacgc cgcgacgtgc gactgcggcg     120
gattacaagg atgacgatga caagggcgtt tctaaaggtg aagaagacaa catggcttct     180
ctgccggcta cccacgaact gcacatcttc ggttctatca cggtgttga cttcgacatg      240
gttggtcagg gtaccggtaa cccgaacgac ggttacgaag aactgaacct gaaatctacc     300
aaaggtgacc tgcagttctc tccgtggatc ttagttccgc acatcggtta cggtttccac     360
cagtacctgc cgtacccgga cggtatgtct ccgttccagg ctgctatggt tgacggttct     420
ggttaccagg ttcaccgtac catgcagttc gaagacggtg cttctctgac cgttaactac     480
cgttacacct acgaaggttc tcacatcaaa ggtgaagctc aggttaaagg taccggtttc     540
ccggctgacg gtccggttat gaccaactct ctgaccgctg ctgactggtg ccgttctaaa     600
aaaacctacc cgaacgacaa accatcatc tctaccttca atggtctta caccaccggt       660
aacggtaaac gttaccgttc tacgctcgt accacctaca ccttcgctaa ccgatggct        720
gctaactacc tgaaaaacca gccgatgtac gttttccgta aaccgaact gaaacactct       780
aaaaccgaac tgaacttcaa agaatggcag aaagctttca ccgacgttat gggtatggac     840
gaactgtaca aggcggtgg cagcggcggt ggcagcgctg agggtgacga tcccgcaaaa      900
gcggccttta actccctgca agcctcagcg accgaatata tcggttatgc gtgggcgatg     960
gttgtt                                                                966

<210> SEQ ID NO 30
<211> LENGTH: 6
<212> TYPE: DNA
<213> ORGANISM: Artificial Sequence
<220> FEATURE:
<223> OTHER INFORMATION: Synthesized

<400> SEQUENCE: 30 aggaga                                                                  6

<210> SEQ ID NO 31
<211> LENGTH: 25
<212> TYPE: DNA
<213> ORGANISM: Artificial Sequence
<220> FEATURE:
<223> OTHER INFORMATION: Synthesized

<400> SEQUENCE: 31
ttaactttaa gaaggagata tacat                                            25

<210> SEQ ID NO 32
<211> LENGTH: 38
<212> TYPE: PRT
<213> ORGANISM: Artificial Sequence
<220> FEATURE:
<223> OTHER INFORMATION: Synthesized

<400> SEQUENCE: 32

Met Asn Asn Asn Asp Leu Phe Gln Ala Ser Arg Arg Arg Phe Leu Ala
1               5                   10                  15
```

```
Gln Leu Gly Gly Leu Thr Val Ala Gly Met Leu Gly Pro Ser Leu Leu
            20                  25                  30

Thr Pro Arg Arg Ala Thr
            35

<210> SEQ ID NO 33
<211> LENGTH: 7
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: Ser or Thr
<220> FEATURE:
<221> NAME/KEY: MISC_FEATURE
<222> LOCATION: (4)..(4)
<223> OTHER INFORMATION: Any amino acid

<400> SEQUENCE: 33

Xaa Arg Arg Xaa Phe Leu Lys
1               5

<210> SEQ ID NO 34
<211> LENGTH: 8
<212> TYPE: PRT
<213> ORGANISM: Artificial Sequence
<220> FEATURE:
<223> OTHER INFORMATION: Synthesized

<400> SEQUENCE: 34

Thr Ser Arg Gln Arg Phe Leu Ala
1               5

<210> SEQ ID NO 35
<211> LENGTH: 38
<212> TYPE: PRT
<213> ORGANISM: Artificial Sequence
<220> FEATURE:
<223> OTHER INFORMATION: Synthesized

<400> SEQUENCE: 35

Met Asn Asn Asn Asp Leu Phe Gln Thr Ser Arg Arg Arg Leu Leu Ala
1               5                   10                  15

Gln Leu Gly Gly Leu Thr Val Ala Gly Met Leu Gly Pro Ser Leu Leu
            20                  25                  30

Thr Pro Arg Arg Ala Thr
            35

<210> SEQ ID NO 36
<211> LENGTH: 8
<212> TYPE: PRT
<213> ORGANISM: Artificial Sequence
<220> FEATURE:
<223> OTHER INFORMATION: Synthesized

<400> SEQUENCE: 36

Thr Ser Arg Arg Arg Leu Leu Ala
1               5

<210> SEQ ID NO 37
<211> LENGTH: 38
<212> TYPE: PRT
<213> ORGANISM: Artificial Sequence
<220> FEATURE:
```

<223> OTHER INFORMATION: Synthesized

<400> SEQUENCE: 37

Met Asn Asn Asn Asp Ile Phe Gln Ala Ser Arg Arg Arg Phe Leu Ala
1               5                   10                  15

Gln Pro Gly Gly Leu Thr Val Ala Gly Met Leu Gly Pro Ser Leu Leu
            20                  25                  30

Thr Pro Arg Arg Ala Thr
        35

<210> SEQ ID NO 38
<211> LENGTH: 13
<212> TYPE: PRT
<213> ORGANISM: Artificial Sequence
<220> FEATURE:
<223> OTHER INFORMATION: Synthesized

<400> SEQUENCE: 38

Ile Phe Gln Ala Ser Arg Arg Arg Phe Leu Ala Gln Pro
1               5                   10

<210> SEQ ID NO 39
<211> LENGTH: 38
<212> TYPE: PRT
<213> ORGANISM: Artificial Sequence
<220> FEATURE:
<223> OTHER INFORMATION: Synthesized

<400> SEQUENCE: 39

Met Asn Asn Asn Glu Leu Phe Gln Ala Ser Arg Arg Arg Phe Leu Ala
1               5                   10                  15

Gln Leu Gly Gly Leu Thr Val Ala Gly Met Leu Gly Pro Ser Leu Leu
            20                  25                  30

Thr Pro Arg Arg Ala Thr
        35

<210> SEQ ID NO 40
<211> LENGTH: 12
<212> TYPE: PRT
<213> ORGANISM: Artificial Sequence
<220> FEATURE:
<223> OTHER INFORMATION: Synthesized

<400> SEQUENCE: 40

Glu Leu Phe Gln Ala Ser Arg Arg Arg Phe Leu Ala
1               5                   10

<210> SEQ ID NO 41
<211> LENGTH: 38
<212> TYPE: PRT
<213> ORGANISM: Artificial Sequence
<220> FEATURE:
<223> OTHER INFORMATION: Synthesized

<400> SEQUENCE: 41

Met Asn Asn Asn Asp Leu Phe Gln Thr Thr Arg Arg Arg Phe Leu Ala
1               5                   10                  15

Gln Leu Gly Gly Leu Thr Val Ala Gly Met Leu Gly Pro Ser Leu Leu
            20                  25                  30

Thr Pro Arg Arg Ala Thr
        35

<210> SEQ ID NO 42

<211> LENGTH: 8
<212> TYPE: PRT
<213> ORGANISM: Artificial Sequence
<220> FEATURE:
<223> OTHER INFORMATION: Synthesized

<400> SEQUENCE: 42

```
Thr Thr Arg Arg Arg Phe Leu Ala
1               5
```

<210> SEQ ID NO 43
<211> LENGTH: 38
<212> TYPE: PRT
<213> ORGANISM: Artificial Sequence
<220> FEATURE:
<223> OTHER INFORMATION: Synthesized

<400> SEQUENCE: 43

```
Met Asn Asn Asn Asp Ser Phe Gln Thr Ser Arg Arg Arg Phe Leu Ala
1               5                   10                  15

Gln Leu Gly Gly Leu Thr Val Ala Gly Met Leu Gly Pro Ser Leu Leu
            20                  25                  30

Thr Pro Arg Arg Ala Thr
        35
```

<210> SEQ ID NO 44
<211> LENGTH: 11
<212> TYPE: PRT
<213> ORGANISM: Artificial Sequence
<220> FEATURE:
<223> OTHER INFORMATION: Synthesized

<400> SEQUENCE: 44

```
Ser Phe Gln Thr Ser Arg Arg Arg Phe Leu Ala
1               5                   10
```

<210> SEQ ID NO 45
<211> LENGTH: 711
<212> TYPE: DNA
<213> ORGANISM: Artificial Sequence
<220> FEATURE:
<223> OTHER INFORMATION: Synthesized

<400> SEQUENCE: 45

| | | | | |
|---|---|---|---|---|
| atggtgagca | agggcgagga | ggataacatg | gcctctctcc | cagcgacaca | tgagttacac | 60 |
| atctttggct | ccatcaacgg | tgtggacttt | gacatggtgg | gtcagggcac | cggcaatcca | 120 |
| aatgatggtt | atgaggagtt | aaacctgaag | tccaccaagg | gtgacctcca | gttctccccc | 180 |
| tggattctgg | tccctcatat | cgggtatggc | ttccatcagt | acctgcccta | ccctgacggg | 240 |
| atgtcgcctt | tccaggccgc | catggtagat | ggctccggat | accaagtcca | tcgcacaatg | 300 |
| cagtttgaag | atggtgcctc | ccttactgtt | aactaccgct | acacctacga | gggaagccac | 360 |
| atcaaaggag | aggcccaggt | gaaggggact | ggtttccctg | ctgacggtcc | tgtgatgacc | 420 |
| aactcgctga | ccgctgcgga | ctggtgcagg | tcgaagaaga | cttaccccaa | cgacaaaacc | 480 |
| atcatcagta | cctttaagtg | gagttacacc | actggaaatg | caagcgcta | ccggagcact | 540 |
| gcgcggacca | cctacacctt | tgccaagcca | atggcggcta | ctatctgaa | gaaccagccg | 600 |
| atgtacgtgt | tccgtaagac | ggagctcaag | cactccaaga | ccgagctcaa | cttcaaggag | 660 |
| tggcaaaagg | cctttaccga | tgtgatgggc | atggacgagc | tgtacaagta | a | 711 |

<210> SEQ ID NO 46

```
<211> LENGTH: 236
<212> TYPE: PRT
<213> ORGANISM: Artificial Sequence
<220> FEATURE:
<223> OTHER INFORMATION: Synthesized

<400> SEQUENCE: 46

Met Val Ser Lys Gly Glu Glu Asp Asn Met Ala Ser Leu Pro Ala Thr
1               5                   10                  15

His Glu Leu His Ile Phe Gly Ser Ile Asn Gly Val Asp Phe Asp Met
            20                  25                  30

Val Gly Gln Gly Thr Gly Asn Pro Asn Asp Gly Tyr Glu Glu Leu Asn
        35                  40                  45

Leu Lys Ser Thr Lys Gly Asp Leu Gln Phe Ser Pro Trp Ile Leu Val
    50                  55                  60

Pro His Ile Gly Tyr Gly Phe His Gln Tyr Leu Pro Tyr Pro Asp Gly
65                  70                  75                  80

Met Ser Pro Phe Gln Ala Ala Met Val Asp Gly Ser Gly Tyr Gln Val
                85                  90                  95

His Arg Thr Met Gln Phe Glu Asp Gly Ala Ser Leu Thr Val Asn Tyr
            100                 105                 110

Arg Tyr Thr Tyr Glu Gly Ser His Ile Lys Gly Glu Ala Gln Val Lys
        115                 120                 125

Gly Thr Gly Phe Pro Ala Asp Gly Pro Val Met Thr Asn Ser Leu Thr
    130                 135                 140

Ala Ala Asp Trp Cys Arg Ser Lys Lys Thr Tyr Pro Asn Asp Lys Thr
145                 150                 155                 160

Ile Ile Ser Thr Phe Lys Trp Ser Tyr Thr Thr Gly Asn Gly Lys Arg
                165                 170                 175

Tyr Arg Ser Thr Ala Arg Thr Thr Tyr Thr Phe Ala Lys Pro Met Ala
            180                 185                 190

Ala Asn Tyr Leu Lys Asn Gln Pro Met Tyr Val Phe Arg Lys Thr Glu
        195                 200                 205

Leu Lys His Ser Lys Thr Glu Leu Asn Phe Lys Glu Trp Gln Lys Ala
    210                 215                 220

Phe Thr Asp Val Met Gly Met Asp Glu Leu Tyr Lys
225                 230                 235

<210> SEQ ID NO 47
<211> LENGTH: 4
<212> TYPE: DNA
<213> ORGANISM: Artificial Sequence
<220> FEATURE:
<223> OTHER INFORMATION: Synthesized

<400> SEQUENCE: 47 gagg                                                                    4

<210> SEQ ID NO 48
<211> LENGTH: 6
<212> TYPE: DNA
<213> ORGANISM: Artificial Sequence
<220> FEATURE:
<223> OTHER INFORMATION: Synthesized

<400> SEQUENCE: 48 aggagg                                                                  6

<210> SEQ ID NO 49
```

```
<211> LENGTH: 7
<212> TYPE: RNA
<213> ORGANISM: Artificial Sequence
<220> FEATURE:
<223> OTHER INFORMATION: Synthesized

<400> SEQUENCE: 49 aggaggu                                                                     7

<210> SEQ ID NO 50
<211> LENGTH: 9
<212> TYPE: DNA
<213> ORGANISM: Artificial Sequence
<220> FEATURE:
<223> OTHER INFORMATION: Synthesized

<400> SEQUENCE: 50 ttaacttta                                                                   9

<210> SEQ ID NO 51
<211> LENGTH: 15
<212> TYPE: DNA
<213> ORGANISM: Artificial Sequence
<220> FEATURE:
<223> OTHER INFORMATION: Synthesized

<400> SEQUENCE: 51
aaggagacag tcata                                                           15

<210> SEQ ID NO 52
<211> LENGTH: 17
<212> TYPE: PRT
<213> ORGANISM: Artificial Sequence
<220> FEATURE:
<223> OTHER INFORMATION: Synthesized

<400> SEQUENCE: 52

Met Ser Gly Leu Asn Asp Ile Phe Glu Ala Gln Lys Ile Glu Trp His
1               5                   10                  15

Glu

<210> SEQ ID NO 53
<211> LENGTH: 8
<212> TYPE: PRT
<213> ORGANISM: Artificial Sequence
<220> FEATURE:
<223> OTHER INFORMATION: Synthesized

<400> SEQUENCE: 53

Trp Ser His Pro Gln Phe Glu Lys
1               5

<210> SEQ ID NO 54
<211> LENGTH: 1032
<212> TYPE: DNA
<213> ORGANISM: Artificial Sequence
<220> FEATURE:
<223> OTHER INFORMATION: Synthesized

<400> SEQUENCE: 54
atgaacaata acgatctctt tcagacatca cgtcagcgtt ttttggcaca actcggcggc         60
ttaaccgtcg ccgggatgct ggggccgtca ttgttaacgc cgcgacgtgc gactgcggcg        120
gattacaagg atgacgatga caagggcgtt tctaaaggtg aagaagacaa catggctttc        180
ctgccggcta cccacgaact gcacatcttc ggttctatca cggtgttga cttcgacatg        240
```

```
gttggtcagg gtaccggtaa cccgaacgac ggttacgaag aactgaacct gaaatctacc    300
aaaggtgacc tgcagttctc tccgtggatc ttagttccgc acatcggtta cggtttccac    360
cagtacctgc cgtacccgga cggtatgtct ccgttccagg ctgctatggt tgacggttct    420
ggttaccagg ttcaccgtac catgcagttc gaagacggtg cttctctgac cgttaactac    480
cgttacacct acgaaggttc tcacatcaaa ggtgaagctc aggttaaagg taccggtttc    540
ccggctgacg gtccggttat gaccaactct ctgaccgctg ctgactggtg ccgttctaaa    600
aaaacctacc cgaacgacaa aaccatcatc tctaccttca aatggtctta caccaccggt    660
aacggtaaac gttaccgttc taccgctcgt accacctaca ccttcgctaa accgatggct    720
gctaactacc tgaaaaacca gccgatgtac gttttccgta aaccgaact gaaacactct    780 aaaaccgaac tgaacttcaa agaatggcag aaagctttca ccgacgttat gggtatggac    840
gaactgtaca aaggcggtgg cagcggcggt ggcagcgctg agggtgacga tcccgcaaaa    900
gcggccttta actccctgca agcctcagcg accgaatata tcggttatgc gtgggcgatg    960
gttgttgtca ttgtcggcgc aactatcggt atcaagctgt ttaagaaatt cacctcgaaa   1020
gcaagctgat aa                                                       1032
```

<210> SEQ ID NO 55
<211> LENGTH: 342
<212> TYPE: PRT
<213> ORGANISM: Artificial Sequence
<220> FEATURE:
<223> OTHER INFORMATION: Synthesized

<400> SEQUENCE: 55

```
Met Asn Asn Asn Asp Leu Phe Gln Thr Ser Arg Gln Arg Phe Leu Ala
1               5                   10                  15

Gln Leu Gly Gly Leu Thr Val Ala Gly Met Leu Gly Pro Ser Leu Leu
            20                  25                  30

Thr Pro Arg Arg Ala Thr Ala Ala Asp Tyr Lys Asp Asp Asp Asp Lys
        35                  40                  45

Gly Val Ser Lys Gly Glu Glu Asp Asn Met Ala Ser Leu Pro Ala Thr
    50                  55                  60

His Glu Leu His Ile Phe Gly Ser Ile Asn Gly Val Asp Phe Asp Met
65                  70                  75                  80

Val Gly Gln Gly Thr Gly Asn Pro Asn Asp Gly Tyr Glu Glu Leu Asn
                85                  90                  95

Leu Lys Ser Thr Lys Gly Asp Leu Gln Phe Ser Pro Trp Ile Leu Val
            100                 105                 110

Pro His Ile Gly Tyr Gly Phe His Gln Tyr Leu Pro Tyr Pro Asp Gly
        115                 120                 125

Met Ser Pro Phe Gln Ala Ala Met Val Asp Gly Ser Gly Tyr Gln Val
    130                 135                 140

His Arg Thr Met Gln Phe Glu Asp Gly Ala Ser Leu Thr Val Asn Tyr
145                 150                 155                 160

Arg Tyr Thr Tyr Glu Gly Ser His Ile Lys Gly Glu Ala Gln Val Lys
                165                 170                 175

Gly Thr Gly Phe Pro Ala Asp Gly Pro Val Met Thr Asn Ser Leu Thr
            180                 185                 190

Ala Ala Asp Trp Cys Arg Ser Lys Lys Thr Tyr Pro Asn Asp Lys Thr
        195                 200                 205

Ile Ile Ser Thr Phe Lys Trp Ser Tyr Thr Thr Gly Asn Gly Lys Arg
```

Tyr Arg Ser Thr Ala Arg Thr Thr Tyr Thr Phe Ala Lys Pro Met Ala
225                 230                 235                 240

Ala Asn Tyr Leu Lys Asn Gln Pro Met Tyr Val Phe Arg Lys Thr Glu
            245                 250                 255

Leu Lys His Ser Lys Thr Glu Leu Asn Phe Lys Glu Trp Gln Lys Ala
            260                 265                 270

Phe Thr Asp Val Met Gly Met Asp Glu Leu Tyr Lys Gly Gly Gly Ser
            275                 280                 285

Gly Gly Gly Ser Ala Glu Gly Asp Asp Pro Ala Lys Ala Ala Phe Asn
            290                 295                 300

Ser Leu Gln Ala Ser Ala Thr Glu Tyr Ile Gly Tyr Ala Trp Ala Met
305                 310                 315                 320

Val Val Val Ile Val Gly Ala Thr Ile Gly Ile Lys Leu Phe Lys Lys
            325                 330                 335

Phe Thr Ser Lys Ala Ser
            340

<210> SEQ ID NO 56
<211> LENGTH: 819
<212> TYPE: DNA
<213> ORGANISM: Artificial Sequence
<220> FEATURE:
<223> OTHER INFORMATION: Synthesized

<400> SEQUENCE: 56
gtttctaaag gtgaagaaga caacatggct tctctgccgg ctacccacga actgcacatc    60
ttcggttcta tcaacggtgt tgacttcgac atggttggtc agggtaccgg taacccgaac   120
gacggttacg aagaactgaa cctgaaatct accaaaggtg acctgcagtt ctctccgtgg   180
atcttagttc gcacatcgg ttacggtttc accagtacc tgccgtaccc ggacggtatg    240
tctccgttcc aggctgctat ggttgacggt tctggttacc aggttcaccg taccatgcag   300
ttcgaagacg gtgcttctct gaccgttaac taccgttaca cctacgaagg ttctcacatc   360
aaaggtgaag ctcaggttaa aggtaccggt ttcccggctg acggtccggt tatgaccaac   420
tctctgaccg ctgctgactg gtgccgttct aaaaaaacct acccgaacga caaaaccatc   480
atctctacct tcaaatggtc ttacaccacc ggtaacggta acgttaccg ttctaccgct    540 cgtaccacct acaccttcgc taaaccgatg gctgctaact acctgaaaaa ccagccgatg   600
tacgttttcc gtaaaaccga actgaaacac tctaaaaccg aactgaactt caaagaatgg   660
cagaaagctt tcaccgacgt tatgggtatg gacgaactgt acaaaggcgg tggcagcggc   720
ggtggcagcg ctgagggtga cgatcccgca aaagcggcct ttaactccct gcaagcctca   780
gcgaccgaat atatcggtta tgcgtgggcg atggttgtt                          819

<210> SEQ ID NO 57
<211> LENGTH: 1312
<212> TYPE: DNA
<213> ORGANISM: Artificial Sequence
<220> FEATURE:
<223> OTHER INFORMATION: Synthesized

<400> SEQUENCE: 57
agtgttttag tgtattcttt cgcctctttc gttttaggtt ggtgccttcg tagtggcatt    60
acgtatttta cccgtttaat ggaaacttcc tcatgataag ctagcaagca aggagacagt   120
cataatgaac aataacgatc tctttcagac atcacgtcag cgttttttgg cacaactcgg   180

```
cggcttaacc gtcgccggga tgctggggcc gtcattgtta acgccgcgac gtgcgactgc    240
ggcggattac aaggatgacg atgacaaggg cgtttctaaa ggtgaagaag acaacatggc    300
ttctctgccg gctacccacg aactgcacat cttcggttct atcaacggtg ttgacttcga    360
catggttggt cagggtaccg gtaacccgaa cgacggttac gaagaactga acctgaaatc    420
taccaaaggt gacctgcagt tctctccgtg gatcttagtt ccgcacatcg gttacggttt    480
ccaccagtac ctgccgtacc cggacggtat gtctccgttc caggctgcta tggttgacgg    540
ttctggttac caggttcacc gtaccatgca gttcgaagac ggtgcttctc tgaccgttaa    600
ctaccgttac acctacgaag gttctcacat caaaggtgaa gctcaggtta aaggtaccgg    660
tttcccggct gacggtccgg ttatgaccaa ctctctgacc gctgctgact ggtgccgttc    720
taaaaaaacc tacccgaacg acaaaaccat catctctacc ttcaaatggt cttacaccac    780
cggtaacggt aaacgttacc gttctaccgc tcgtaccacc tacaccttcg ctaaaccgat    840
ggctgctaac tacctgaaaa accagccgat gtacgttttc cgtaaaaccg aactgaaaca    900
ctctaaaacc gaactgaact tcaaagaatg gcagaaagct ttcaccgacg ttatgggtat    960
ggacgaactg tacaaaggcg gtggcagcgg cggtggcagc gctgagggtg acgatcccgc   1020
aaaagcggcc tttaactccc tgcaagcctc agcgaccgaa tatatcggtt atgcgtgggc   1080
gatggttgtt gtcattgtcg gcgcaactat cggtatcaag ctgtttaaga aattcacctc   1140
gaaagcaagc tgataagcta gcttgaggca tcaataaaac gaaaggctca gtcgaaagac   1200
tgggcctttc attttatctg ttgtttgtcg gttaacgctt gcgtcatcg tccttgtagt   1260 ctttttttag agaatctgcg gctttcgcat cagcttccgg ctttgcatca gc           1312

<210> SEQ ID NO 58
<211> LENGTH: 24
<212> TYPE: DNA
<213> ORGANISM: Artificial Sequence
<220> FEATURE:
<223> OTHER INFORMATION: Synthesized

<400> SEQUENCE: 58
agtgttttag tgtattcttt cgcc                                            24

<210> SEQ ID NO 59
<211> LENGTH: 16
<212> TYPE: DNA
<213> ORGANISM: Artificial Sequence
<220> FEATURE:
<223> OTHER INFORMATION: Synthesized

<400> SEQUENCE: 59
gctgatgcaa agccgg                                                     16

<210> SEQ ID NO 60
<211> LENGTH: 150
<212> TYPE: DNA
<213> ORGANISM: Artificial Sequence
<220> FEATURE:
<223> OTHER INFORMATION: Synthesized

<400> SEQUENCE: 60
gctgagggtg acgatcccgc aaaagcggcc tttaactccc tgcaagcctc agcgaccgaa     60
tatatcggtt atgcgtgggc gatggttgtt gtcattatag gcgccactat cggtatcaag    120
ctgtttaaga aattcacctc gaaagcaagc                                     150
```

```
<210> SEQ ID NO 61
<211> LENGTH: 50
<212> TYPE: PRT
<213> ORGANISM: Artificial Sequence
<220> FEATURE:
<223> OTHER INFORMATION: Synthesized

<400> SEQUENCE: 61

Ala Glu Gly Asp Asp Pro Ala Lys Ala Ala Phe Asn Ser Leu Gln Ala
1               5                   10                  15

Ser Ala Thr Glu Tyr Ile Gly Tyr Ala Trp Ala Met Val Val Val Ile
            20                  25                  30

Ile Gly Ala Thr Ile Gly Ile Lys Leu Phe Lys Lys Phe Thr Ser Lys
        35                  40                  45

Ala Ser
    50
```